US009637723B2

(12) United States Patent
Rafii et al.

(10) Patent No.: US 9,637,723 B2
(45) Date of Patent: May 2, 2017

(54) GENERATION OF FUNCTIONAL AND DURABLE ENDOTHELIAL CELLS FROM HUMAN AMNIOTIC FLUID-DERIVED CELLS

(71) Applicant: Cornell University, Ithaca, NY (US)

(72) Inventors: Shahin Rafii, New York, NY (US); Sina Y. Rabbany, Great Neck, NY (US); Michael Ginsberg, New York, NY (US)

(73) Assignee: CORNELL UNIVERSITY Q, Ithaca, NY (US)

( * ) Notice: Subject to any disclaimer, the term of this patent is extended or adjusted under 35 U.S.C. 154(b) by 0 days.

(21) Appl. No.: 14/404,739

(22) PCT Filed: May 30, 2013

(86) PCT No.: PCT/US2013/043236
§ 371 (c)(1),
(2) Date: Dec. 1, 2014

(87) PCT Pub. No.: WO2013/181326
PCT Pub. Date: Dec. 5, 2013

(65) Prior Publication Data
US 2015/0147299 A1 May 28, 2015

Related U.S. Application Data

(60) Provisional application No. 61/653,185, filed on May 30, 2012, provisional application No. 61/709,431, filed on Oct. 4, 2012.

(51) Int. Cl.
*C12N 5/00* (2006.01)
*C12Q 1/02* (2006.01)
(Continued)

(52) U.S. Cl.
CPC ............. *C12N 5/069* (2013.01); *A61K 35/44* (2013.01); *A61K 48/00* (2013.01);
(Continued)

(58) Field of Classification Search
CPC ............. C12N 5/069; C12N 2501/115; C12N 2501/15; C12N 2501/155;
(Continued)

(56) References Cited

U.S. PATENT DOCUMENTS 5,994,136 A 11/1999 Naldini et al.
6,013,516 A 1/2000 Verma et al.
(Continued)

FOREIGN PATENT DOCUMENTS

WO 03/059940 A1 7/2003
WO 03/059941 A1 7/2003
(Continued)

OTHER PUBLICATIONS

Nolan et al. (Genes & Development, vol. 21, pp. 1546-1558, 2007).*
(Continued)

*Primary Examiner* — Reza Ghafoorian
(74) *Attorney, Agent, or Firm* — Scully, Scott, Murphy & Presser, P.C.

(57) ABSTRACT

This disclosure is directed to methods for reproducibly generating substantial amounts of endothelial cells from amniotic cells. The endothelial cells generated in accordance with the present methodology, as well as therapeutic methods utilizing these cells, are also disclosed.

12 Claims, 26 Drawing Sheets
(23 of 26 Drawing Sheet(s) Filed in Color)

(51) Int. Cl.
  *C12N 5/071* (2010.01)
  *A61K 35/44* (2015.01)
  *A61K 48/00* (2006.01)
(52) U.S. Cl.
  CPC .... *C12N 2501/115* (2013.01); *C12N 2501/15* (2013.01); *C12N 2501/155* (2013.01); *C12N 2501/165* (2013.01); *C12N 2501/60* (2013.01); *C12N 2501/999* (2013.01); *C12N 2506/02* (2013.01); *C12N 2506/025* (2013.01); *C12N 2510/00* (2013.01); *C12N 2510/02* (2013.01)
(58) Field of Classification Search
  CPC ........ C12N 2501/165; C12N 2501/999; C12N 2501/60; C12N 2506/02; C12N 2506/025; C12N 2510/02; C12N 2510/00; A61K 35/44; A61K 48/00
  See application file for complete search history.

(56) References Cited

U.S. PATENT DOCUMENTS

| | | | |
|---|---|---|---|
| 6,465,493 B1 | 10/2002 | Burgess et al. | |
| 7,417,041 B2 | 8/2008 | Blumberg et al. | |
| 2003/0149277 A1 | 8/2003 | Gaster et al. | |
| 2003/0166633 A1 | 9/2003 | Gaster et al. | |
| 2004/0039198 A1 | 2/2004 | Bender et al. | |
| 2004/0063745 A1 | 4/2004 | Gellibert et al. | |
| 2004/0152738 A1 | 8/2004 | Gaster et al. | |
| 2004/0220230 A1 | 11/2004 | Gaster et al. | |
| 2004/0266842 A1 | 12/2004 | Gaster et al. | |
| 2005/0014938 A1 | 1/2005 | Gaster et al. | |
| 2005/0165011 A1 | 7/2005 | Gellibert et al. | |
| 2007/0072901 A1 | 3/2007 | Washio | |
| 2007/0154428 A1 | 7/2007 | Sato et al. | |
| 2012/0009618 A1* | 1/2012 | Yu | G01N 33/5064 435/29 |

FOREIGN PATENT DOCUMENTS

| | | |
|---|---|---|
| WO | 2008/089448 A2 | 7/2008 |
| WO | WO 2011/090684 A2 | 7/2011 |
| WO | WO 2012/006440 A2 | 1/2012 |
| WO | 2012/064834 A2 | 5/2012 |

OTHER PUBLICATIONS

Inman et al., SB-431542 Is a Potent and Specific Inhibitor of Transforming Growth Factor—Superfamily Type I Activin Receptor-Like Kinase (ALK) Receptors ALK4, ALK5, and ALK7, Mol Pharmacol 62:65-74, 2002.*
Arteaga et al., Anti-Transforming Growth Factor (TGF)-,B Antibodies Inhibit Breast Cancer Cell Tumorigenicity and Increase Mouse Spleen Natural Killer Cell Activity, J. Clin. Invest., vol. 92, Dec. 1993, 2569-2576.*
Meadows S.M. et al., "Regulation of Endothelial Cell Developments by ETS Transcription Factors", Seminars in Cell & Developmental Biology 22(9):976-984 (Dec. 1, 2011).
Extended Supplementary European Search Report dated Oct. 5, 2015 received from European Application No. 13797778.1.
Chinese Office Action dated Feb. 1, 2016 received from Chinese Patent Application No. 201380037915.3, together with an English-language translation.
Arnhold, S. et al., "Amniotic-Fluid stem cells: Growth Dynamics and differentiation potential after a CD-117-Based Selection Procedure" Stem Cells Int (2011) pp. 1-12, vol. 715341.
Asano, Y. et al., "Endothelial Fli1 Deficiency Impairs Vascular Homeostasis" Am J Pathol (Apr. 2010) pp. 1983-1998, vol. 176, No. 4.
Asano, Y. et al., "Phosphorylation of Fli1 at Threonine 312 by Protein Kinase C δ Promotes Its Interaction with p300/CREB-Binding Protein-Associated Factor and Subsequent Acetylation in Response to Transforming Growth Factor β" Mol Cell Biol (Apr. 2009) pp. 1882-1894, vol. 29, No. 7.
Benten, D. et al., "Hepatic Targeting of Transplanted Liver Sinusoidal Endothelial Cells in Intact Mice" Hepatology (2005) pp. 140-148, vol. 42, No. 1.
Benavides, O. et al., "Evaluation of Endothelial Cells Differentiated from Amniotic Fluid-Derived Stem Cells" Tissue Eng: Part A (2012) pp. 1123-1131, vol. 18, Nos. 11 and 12.
Birdsey, G.M. et al., "Transcription factor Erg regulates angiogenesis and endothelial apoptosis through VE-cadherin" Blood (Apr. 2008) pp. 3498-3506, vol. 111, No. 7.
Bossolasco, P. et al., "Molecular and phenotypic characterization of human amniotic fluid cells and their differentiation potential" Cell Res (2006) pp. 329-336, vol. 16.
Butler, J.M. et al., "Endothelial Cells are Essential for the Self-Renewal and Repopulation of Notch-Dependent Hematopoietic Stem Cells" Cell Stem Cell (2010) pp. 251-264, vol. 6.
Butler, J.M. et al., "Instructive role of the vascular niche in promoting tumour growth and tissue repair by angiocrine factors" Nat Rev Cancer (Feb. 2010) pp. 138-146, vol. 10, No. 2.
Cox, M., "The FLP protein of the yeast 2-μm plasmid: Expression of a eukaryotic genetic recombination system in *Escherichia coli*" Proc. Natl. Acad. Sci. USA (Jul. 1983) pp. 4223-4227, vol. 80.
Cui, J.-W. et al., "Continuous Fli-1 expression plays as essential role in the proliferation and survival of F-MuLV-induced erythroleukemia and human erythroleukemia" Leukemia (2009) pp. 1311-1319, vol. 23.
De Coppi, P. et al., "Isolation of amniotic stem cell lines with potential for therapy" Nature biotechnology (Jan. 2007) pp. 100-106, vol. 25, No. 1.
De Val, S. et al., "Combinatorial Regulation of Endothelial Gene Expression by Ets and Forkhead Transcription Factors" Cell (Dec. 2008) pp. 1053-1064, vol. 135.
De Val, S. et al., "Transcriptional Control of Endothelial Cell Development" Dev Cell (Feb. 2009) pp. 180-195, vol. 16.
Ding, B. et al., "Endothelial-Derived Angiocrine Signals Induce and Sustain Regenerative Lung Alveolarization" Cell (Oct. 2011) pp. 539-553, vol. 147.
Ding, B. et al., "Inductive angiocrine signals from sinusoidal endothelium are required for liver regeneration" Nature (Nov. 2010) pp. 310-315, vol. 468, No. 7321.
Dryden, N.H. et al., "The Transcription Factor Erg Controls Endothelial Cell Quiescence by Repressing Activity of Nuclear Factor (NF)-κB p65" J Biol Chem (Apr. 2012) pp. 12331-12342, vol. 287, No. 15.
Gosden, C.M., "Amniotic Fluid Cell Types and Culture" British Medical Bulletin (1983) pp. 348-354, vol. 39, No. 4.
Hackett, C.H. et al., "Comparison of Gene-specific DNA methylation Patterns in Equine Induced Pluripotent Stem Cell Lines with Cells Derived from Equine Adult and Fetal Tissue" Stem Cells and Development (2012) pp. 1803-1811, vol. 21, No. 10.
Hamilton, D.L. et al., "Site-specific recombination by the Bacteriophage P1 lox-Cre system, Cre-mediated synapses of Two lox Sites" J. Mol. Biol. (1984) pp. 481-486, vol. 178.
Ho, A. et al., "Synthetic Protein Transduction Domains: Enhances Transduction Potential in Vitro and in Vivo" Cancer Research (Jan. 2001) pp. 474-477, vol. 61, No. 2.
Hoehn, H. et al., "Morphological and biochemical heterogeneity of amniotic fluid" Methods Cell Biol (1982) pp. 11-34, vol. 26.
Ingram, D.A. et al., "Identification of a novel hierarchy of endothelial progenitor cells using human peripheral and umbilical cord blood" Blood ( Nov. 2004) pp. 2752-2760, vol. 104, No. 9.
James, D. et al., "Expansion and Maintenance of human embryonic stell cell-derived endothelial cells by TGFβ inhibition is Id1 dependent" Nat Biotechnol (Feb. 2010) pp. 161-166, vol. 28, No. 2.
Jezierski, A. et al., "Probing Stemness and Neural Commitment in Human Amniotic Fluid Cells" Stem cell reviews (2010) pp. 199-214, vol. 6.
Jin, D.K. et al., "Cytokine-mediated deployment of SDF-1 induces revascularization through recruitment of CXCR4+ hemangiocytes" Nat Med (May 2006) pp. 557-567, vol. 12, No. 5.

(56) References Cited

OTHER PUBLICATIONS

Kataoka, H. et al., "Etv2/ER71 induces vascular mesoderm from Flk1+PDGFRα+ primitive mesoderm" Blood (Dec. 2011) pp. 6975-6986, vol. 118, No. 26.
Kobayashi, H. et al., "Angiocrine factors from Akt-activated endothelial cells balance self-renewal and differentiation of haematopoietic stem cells" Nature cell biology (Nov. 2010) pp. 1046-1056, vol. 12, No. 11.
König, J. et al., "Amnion-Derived Mesenchymal Stromal Cells Show Angiogenic Propertied but Resist Differentiation into Mature Endothelial Cells" Stem cells and development (2012) pp. 1309-1320, vol. 21, No. 8.
Lee, D. et al., "ER71 Acts Downstream of BMP, Notch, and Wnt Signaling in Blood and Vessel Progenitor Specification" Cell stem cell (May 2008) pp. 497-507, vol. 2.
Lelievre, E. et al., "The Ets family contains transcriptional activators and repressors involved in angiogenesis" The International Journal of Biochemistry & Cell Biology (2001) pp. 391-407, vol. 33.
Liu, F. et al., "Genome-Wide Analysis of the Zebrafish ETS Family Identifies Three Genes Required for Hemangioblast Differentiation or Angiogensis" Circ Res (Nov. 2008) pp. 1147-1154, vol. 103.
Liu, F. et al., "Fli1 Acts as the top of the Transcriptional Network Driving Blood and Endothelial Development" Current Bio. (Aug. 2008) pp. 1234-1240, vol. 18.
Lyden, D. et al., "Impaired recruitment of bone-marrow-derived endothelial and hematopoietic precursor cells blocks tumor angiogenesis and growth" Nat Med (Nov. 2001) pp. 1194-1201, vol. 7, No. 11.
Mandriota, S.J. et al., "Transforming Growth Factor b1 Down-regulates Vascular Endothelial Growth Factor Receptor 2/flk-1 Expression in Vascular Endothelial Cells" J Biol Chem (1996) pp. 11500-11505, vol. 271, No. 19.
Martens, J., "Acute myeloid leukemia: A central role for the ETS factor ERG" Int J Biochem Cell Biol (2011) pp. 1413-1416, vol. 43.
McLaughlin, F. et al., "Combined genomic and antisense analysis reveals that the transcription factor Erg is implicated in endothelial cell differentiation" Blood (Dec. 2001) pp. 3332-3339, vol. 98, No. 12.
Medici, D. et al., "Conversion of vascular endothelial cells into multipotent stem-like cells" Nat Med (Dec. 2010) pp. 1400-1406, vol. 16, No. 12.
Naldini, L. et al., "In Vivo Gene Delivery and Stable Transduction of Nondiving Cells by a Lentiviral Vector" Science (Apr. 1996) pp. 263-267, vol. 272.
Pham, V.N. et al., "Combinatorial function of ETS transcription factors in the developing vasculature" Dev Biol (2007) pp. 772-783, vol. 303.
Prusa, A.-R. et al., "Amniotic fluid cells and human stem cell research—a new connection" Med Sci Monit (2002) pp. RA253-RA257, vol. 8, No. 11.
Prusa, A.-R. et al., "Oct-4-expressing cells in human amniotic fluid: a new source for stem cell research?" Hum Reprod (2003) pp. 1489-1493, vol. 18, No. 7.
Rafii, S. et al., "Isolation and Characterization of Human Bone Marrow Microvascular Endothelial Cells: Hematopoietic Progenitor Cell Adhesion" Blood (Jul. 1994) pp. 10-19, vol. 84, No. 1.
Rafii, S. et al., "Human Bone Marrow Microvascular Endothelial Cells Support Long-Term Proliferation and Differentiation of Myeloid and Megakaryocyctic Progenitors" Blood (Nov. 1995) pp. 3353-3363, vol. 86, No. 9.
Rafii, S. et al., "Therapeutic stem and progenitor cell transplantation for organ vascularization and regeneration" Nat Med (Jun. 2003) pp. 702-712, vol. 9, No. 6.

Rafii, S. et al., "Vascular and Haematopoietic Stem Cells: Novel Targets for Anti-Angiogenesis Therapy" Nat Rev Cancer (Nov. 2002) pp. 826-835, vol. 2.
Reinisch, A. et al., "Humanized large-scale expanded endothelial colony-forming cells function in vitro and in vivo" Blood (Jun. 2009) pp. 6716-6725, vol. 113, No. 26.
Rothbard, J.B. et al., "Conjugation of arginine oligomers to cyclosporine A facilitates topical delivery and inhibition of inflammation" Nature Med. (Nov. 2000) pp. 1253-1257, vol. 6, No. 11.
Sato, Y., "Role of ETS Family Transcription Factors in Vascular Development and Angiogenesis" Cell Struct Funct (2001) pp. 19-24, vol. 26.
Sauer, B. et al., "Cre-stimulated recombination at loxP-containing DNA sequences into the mammalian genome" Nucleic Acids Res. (1989) pp. 147-161, vol. 17, No. 1.
Sauer, B. et al., "Site-specific DNA recombination in mammalian cells by the Cre recombinase of bacteriophage P1" Proc. Natl. Acad. Sci. USA (Jul. 1988) pp. 5166-5170, vol. 85.
Simon, M.C. et al., "The role of oxygen availability in embryonic development and stem cell function" Nature reviews Molecular cell biology (Apr. 2008) pp. 285-296, vol. 9.
Sternberg, N. et al., "Bacteriophage P1 cre Gene and its regulatory Region: Evidence for Multiple Promoters and for Regulation by DNA Methylation" J. Mol. Biol. (1986) pp. 197-212, vol. 187.
Sumanas, S. et al., "Interplay among Etsrp/ER71, Scl, and Alk8 signaling controls endothelial and myeloid cell formation" Blood (May 2008) pp. 4500-4510, vol. 111, No. 9.
Trapnell, C. et al., "TopHat: discovering splice junctions with RNA-Seq" Bioinformatics (2009) pp. 1105-1111, vol. 25, No. 9.
Trapnell, C. et al., "Transcipt assembly and quantification by RNA-Seq reveals unannotated transcripts and isoform switching during cell differentiation" Nat Biotechnol (May 2010) pp. 511-515, vol. 28, No. 5.
Yamamoto, A. et al., "Current prospects for mRNA gene delivery" Eur. J. Phar. Biophar (2009) pp. 484-489, vol. 71.
Yingling, J.M. et al., "Development of TGF-β signaling inhibitors for cancer therapy" Nature Reviews (Drug Discovery) (Dec. 2004) pp. 1011-1022, vol. 3.
Yoder, M.C. et al., "Redefining endothelial progenitor cells via clonal analysis and hematopoietic stem/progenitor cell principals" Blood (Mar. 2007) pp. 1801-1809, vol. 109, No. 5.
Yuan, L. et al., "ETS-related gene (ERG) controls endothelial cell permeability via transcriptional regulation of the claudin 5 (CLDN5) gene" J Bio Chem (Feb. 2012) pp. 6582-6591, 287, No. 9.
Yuan, L. et al., "Antiinflammatory effects of the ETS factor ERG in endothelial cells are mediated through transcriptional repression of the Interleukin-8 gene" Circ Res (May 2009) pp. 1049-1057, vol. 104.
Zeisberg, E.M. et al., "Endothelial-to-mesenchymal transition contributes to cardiac fibrosis" Nat Med (Aug. 2007) pp. 952-961, vol. 13, No. 8.
Zhang, L. et al., "The Fli-1 proto-oncogene, involved in erythroleukemia and Ewing's sarcoma, encodes a transcriptional activator with DAN-binding specificities distinct from other Ets family members" Oncogene (1993) pp. 1621-1630, vol. 8.
Zhang, P. et al., "Endothelial differentiation of amniotic fluid-derived stem cells: synergism of biochemical and shear force stimuli" Stem cells and development (2009) pp. 1299-1308, vol. 18, No. 9.
International Search Report dated Sep. 19, 2013 issued in International Application No. PCT/US2013/043236.

\* cited by examiner

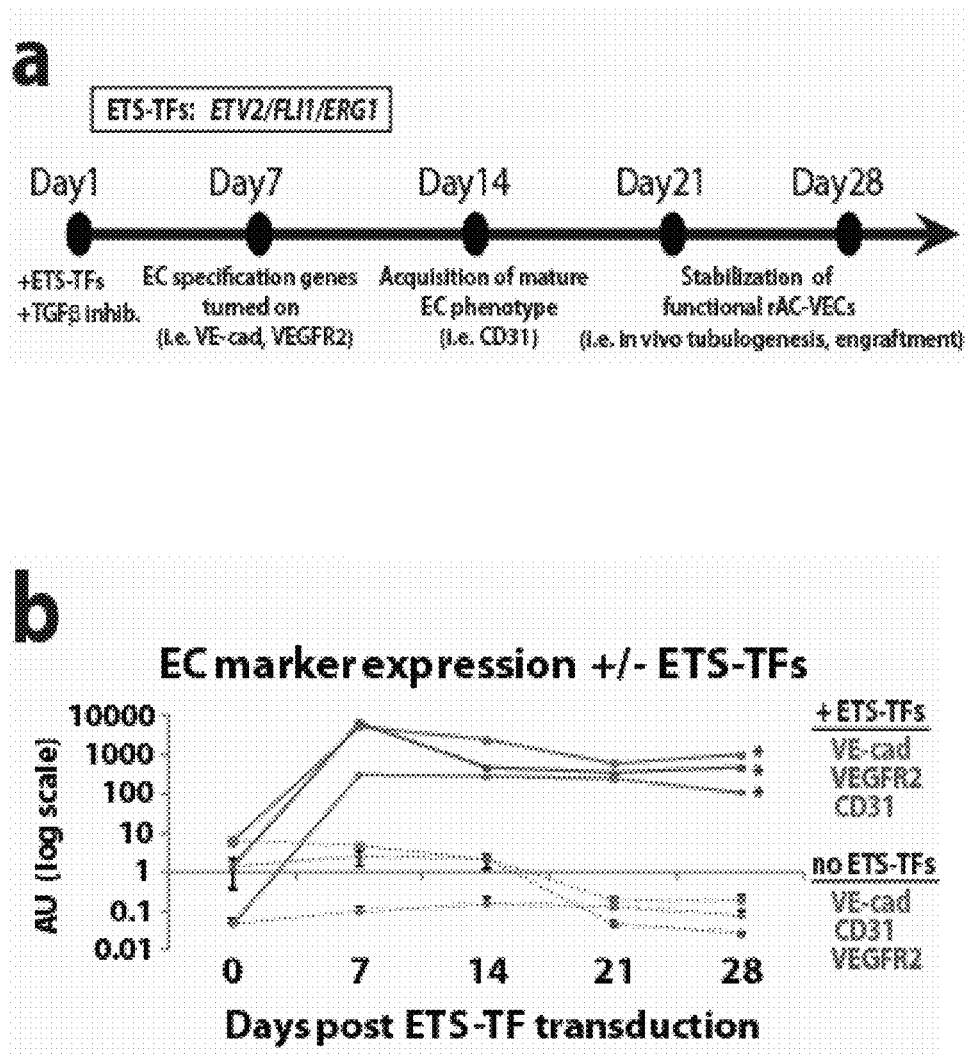
Figures 1a-b

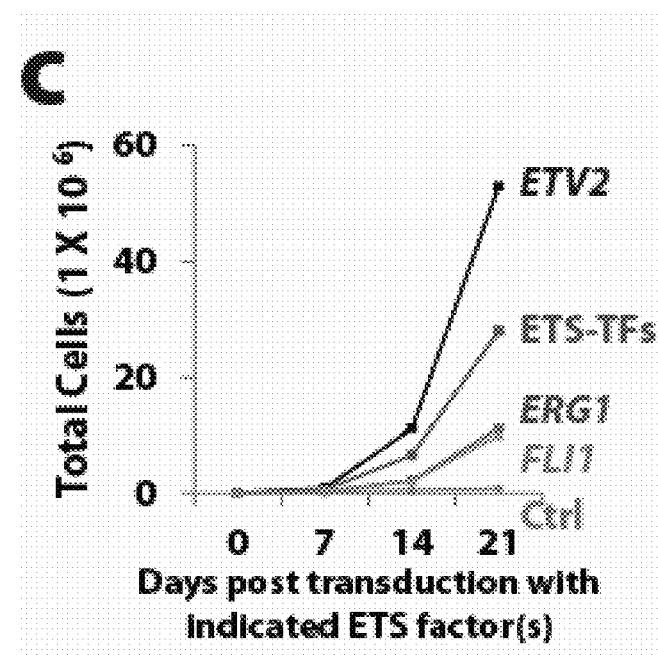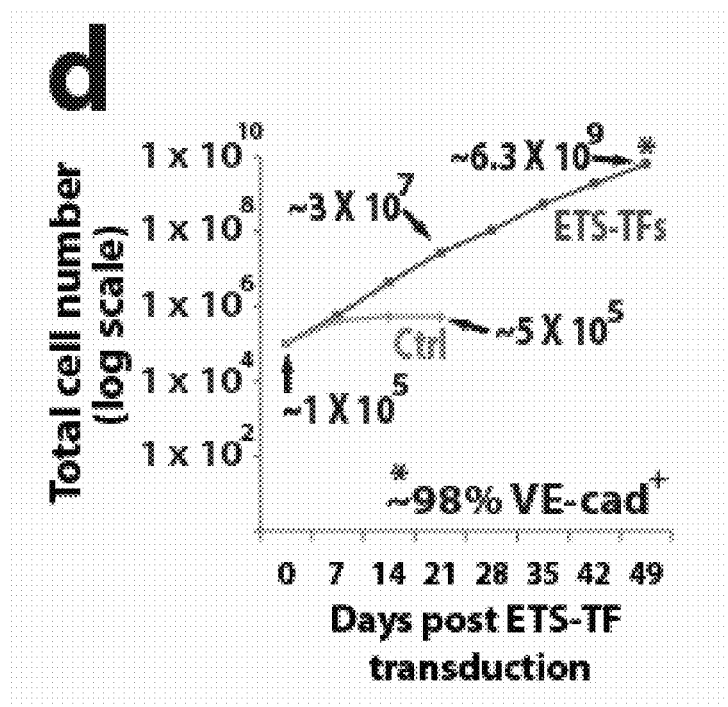
Figures 1c-d

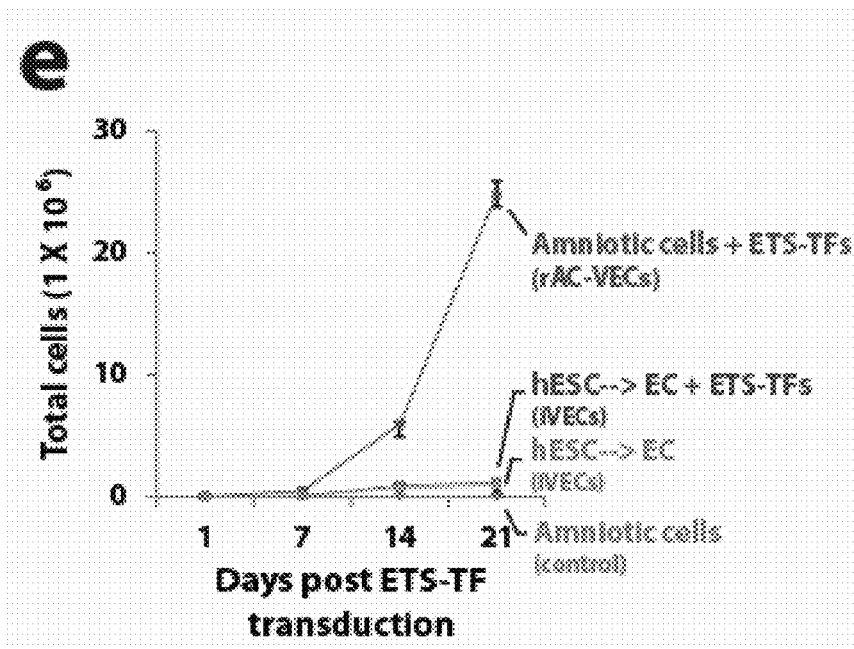
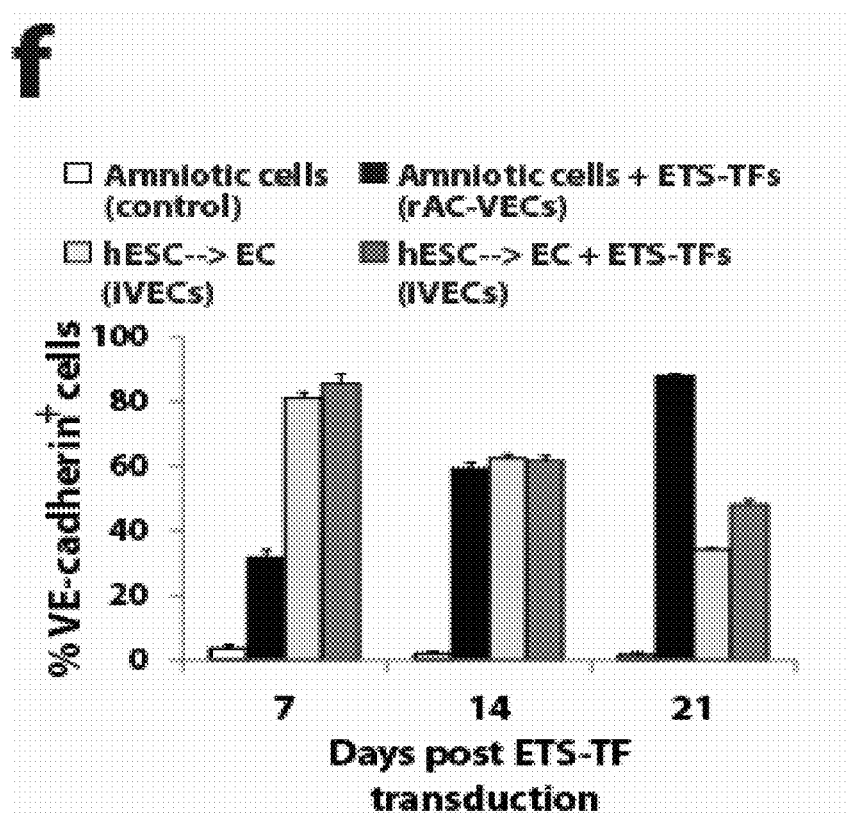
Figures 1e-f

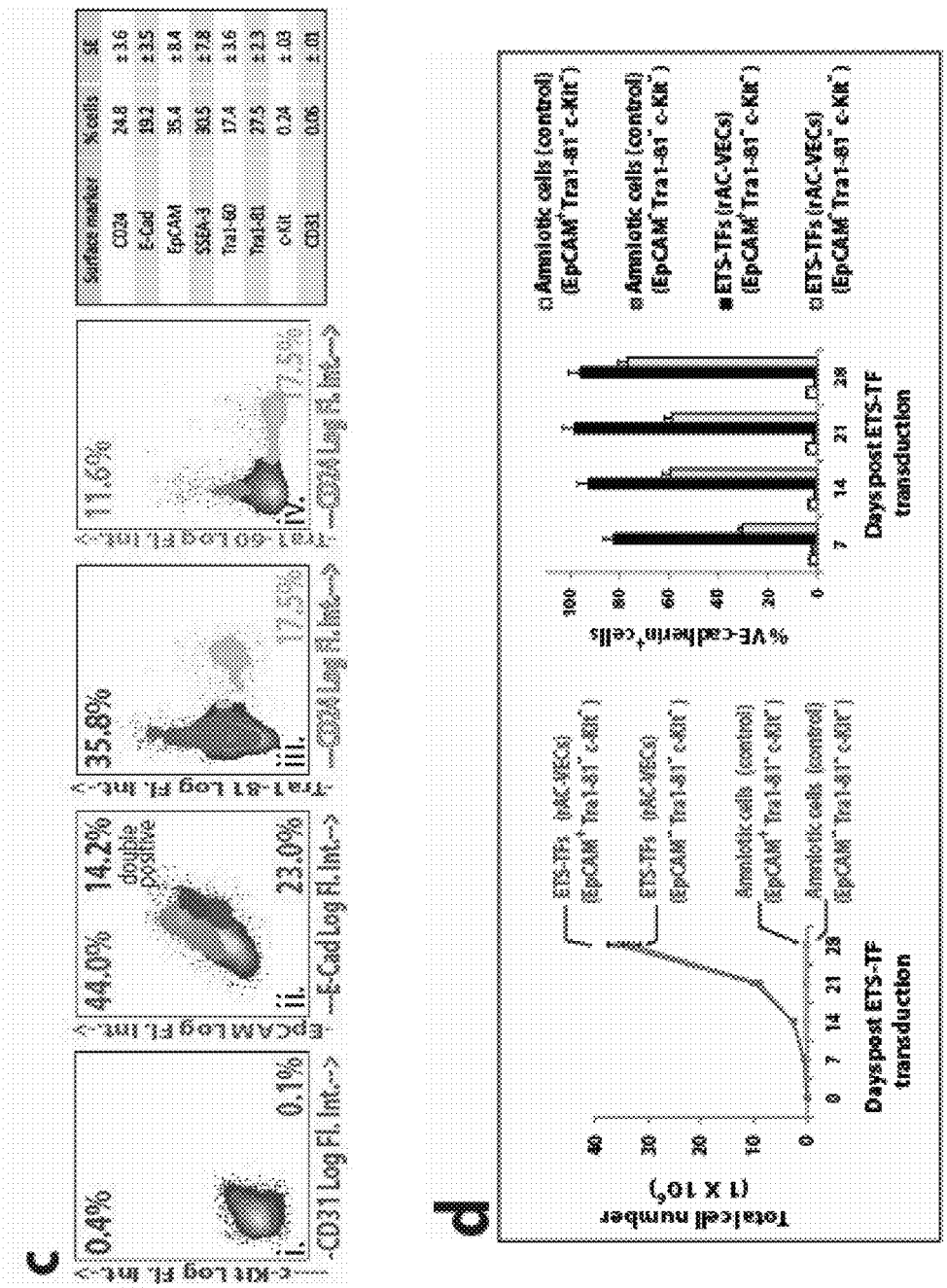
Figures 2c-d

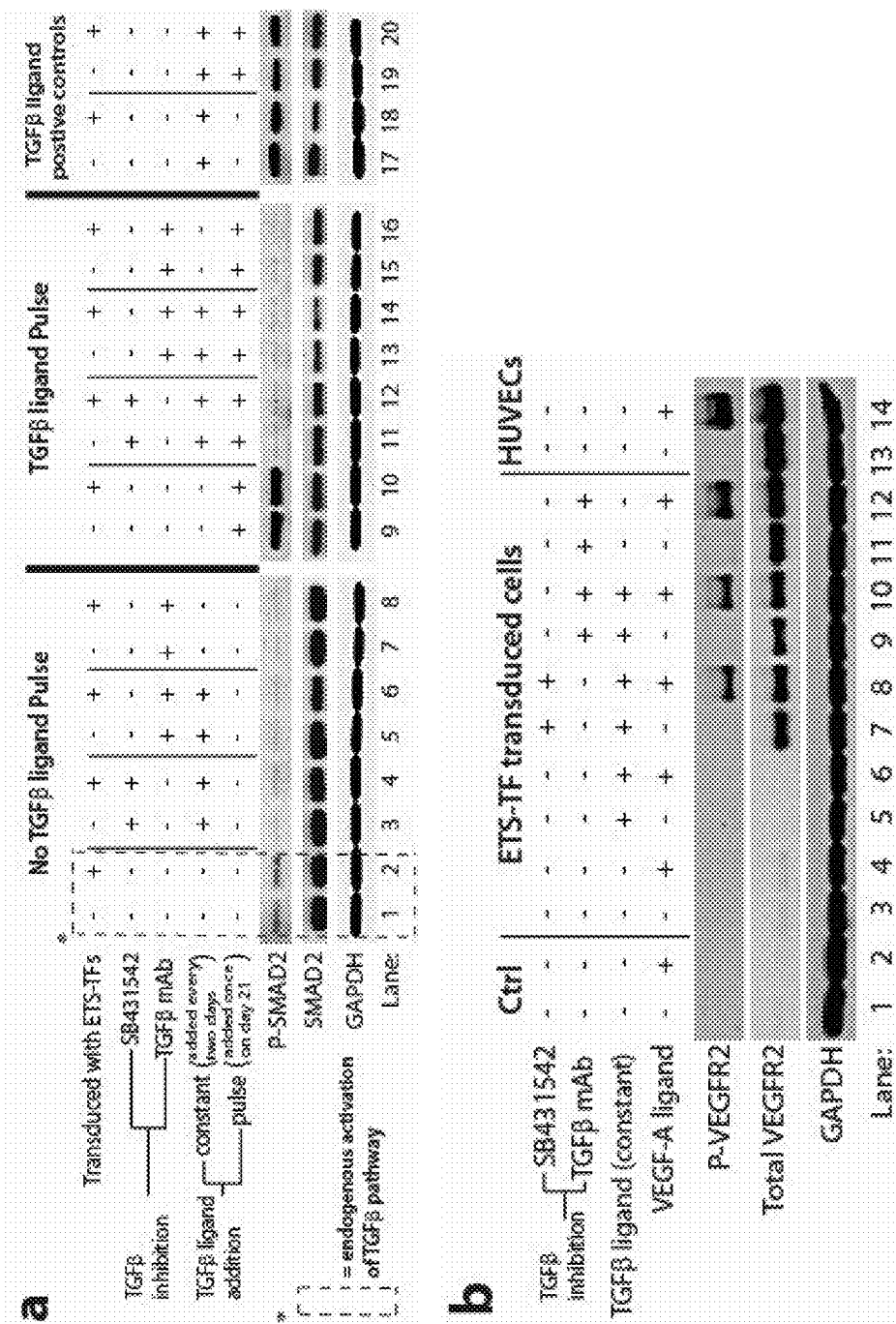
Figures 5a-b

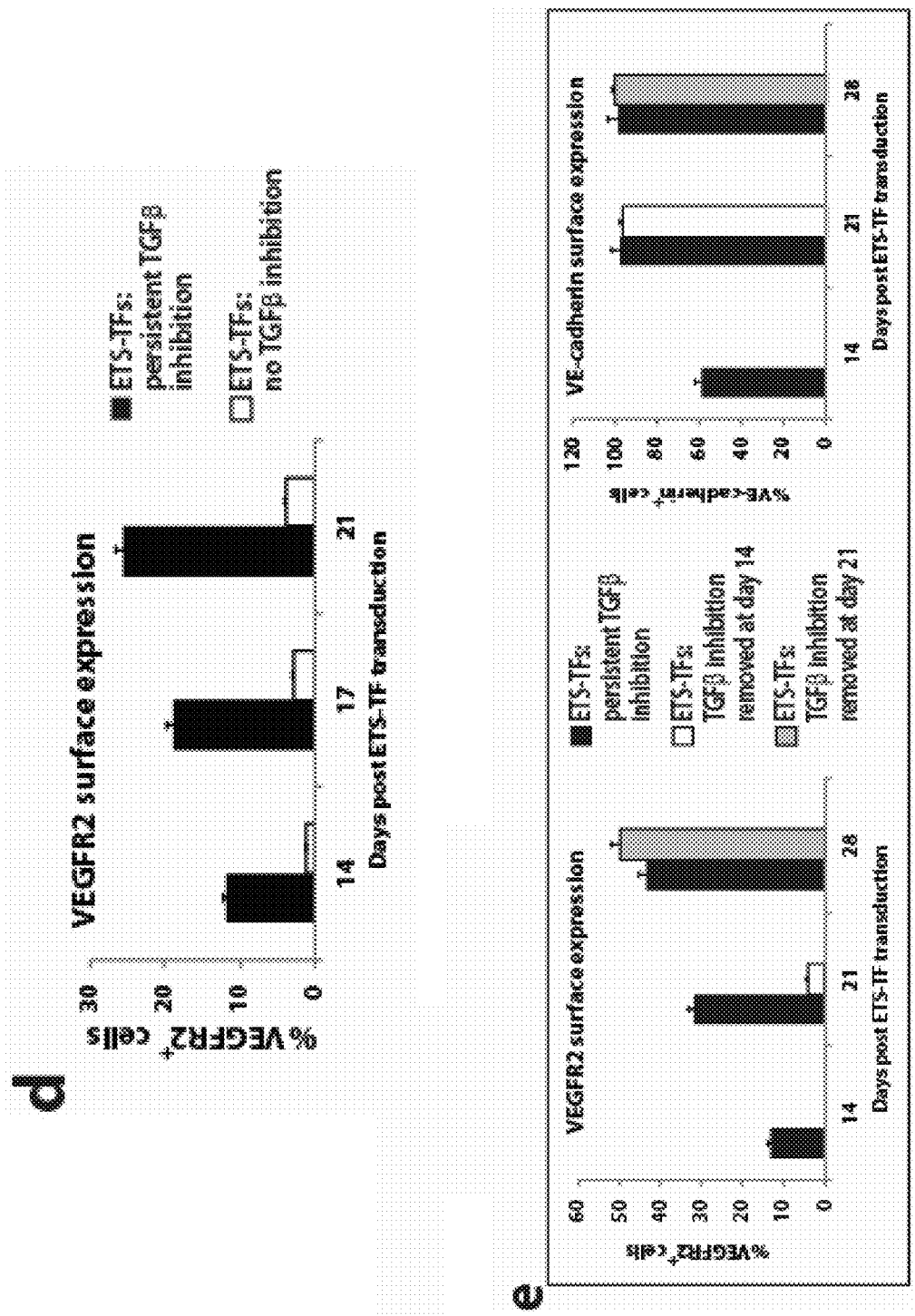
Figures 5d-e

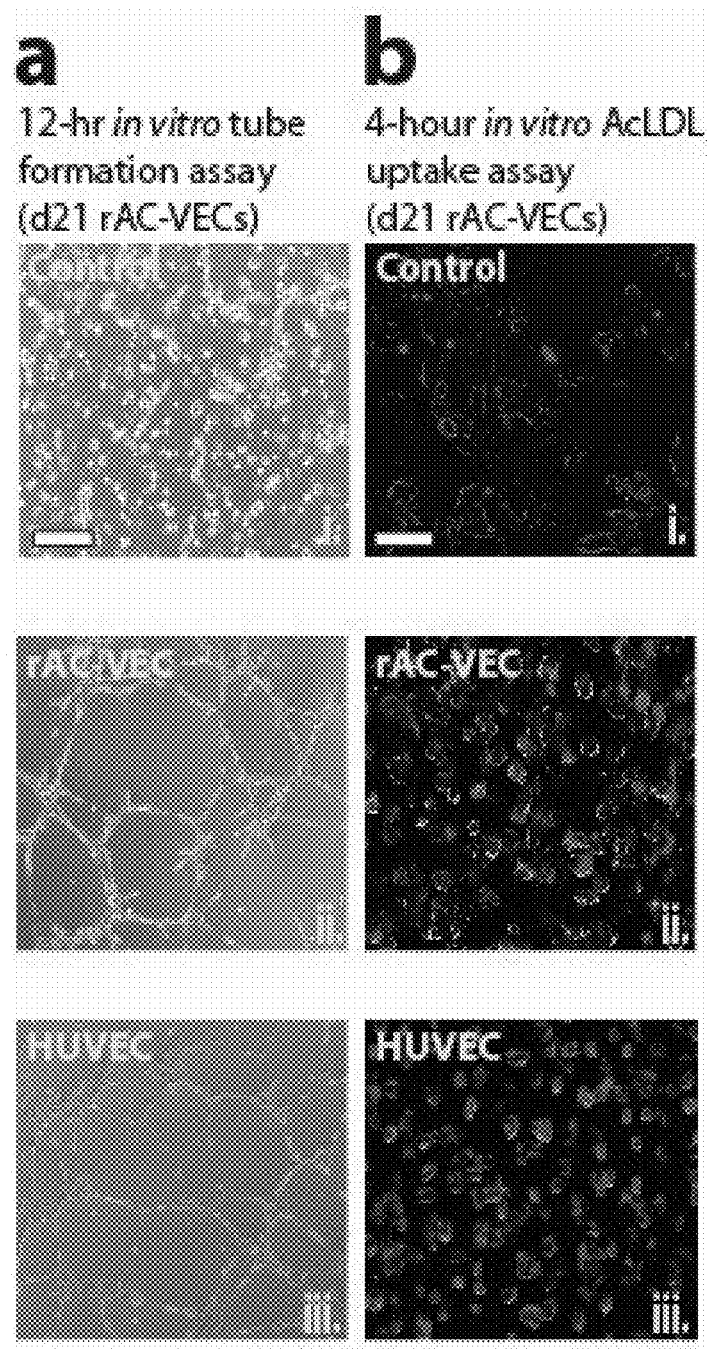
Figures 6a-b

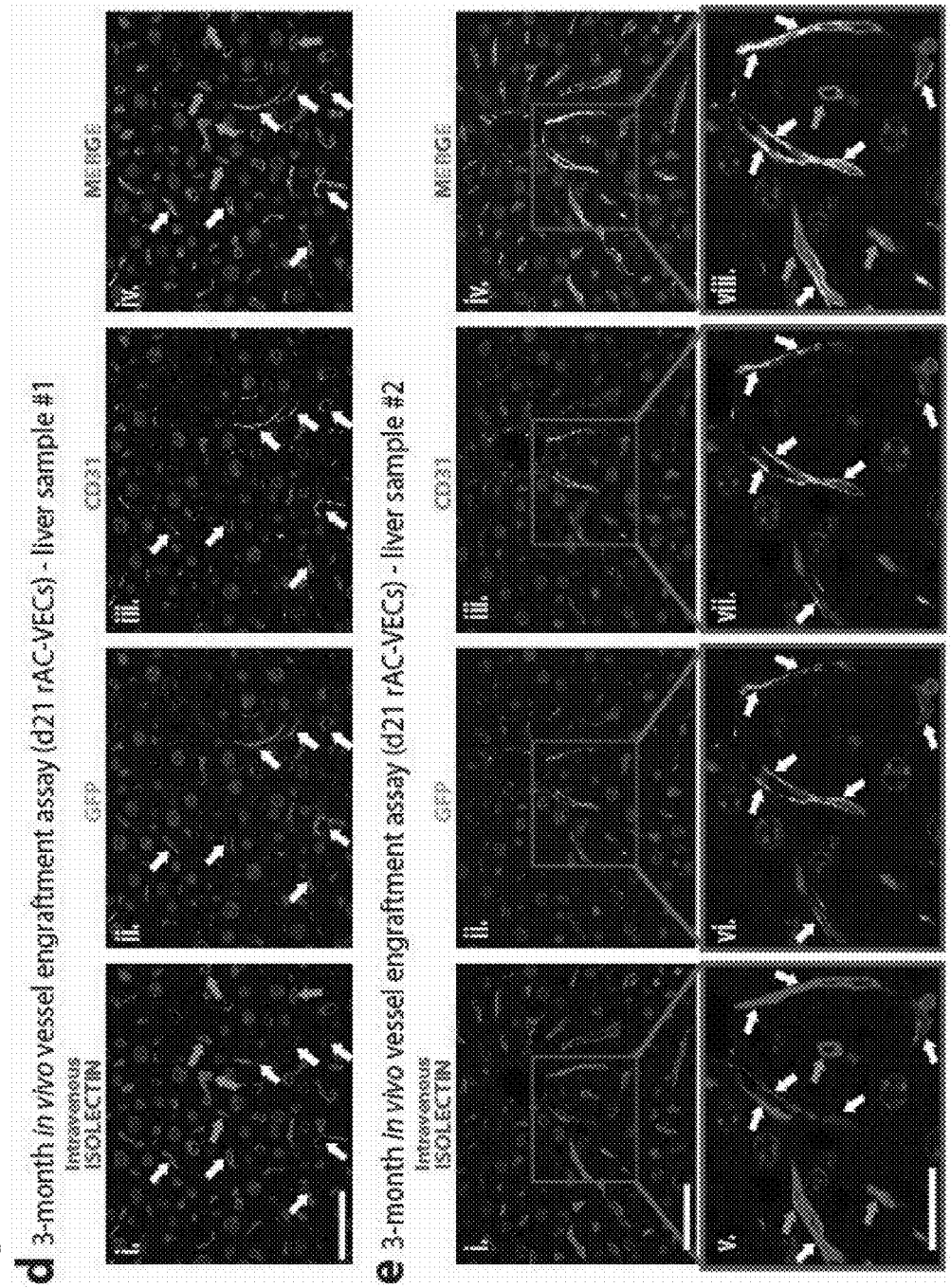

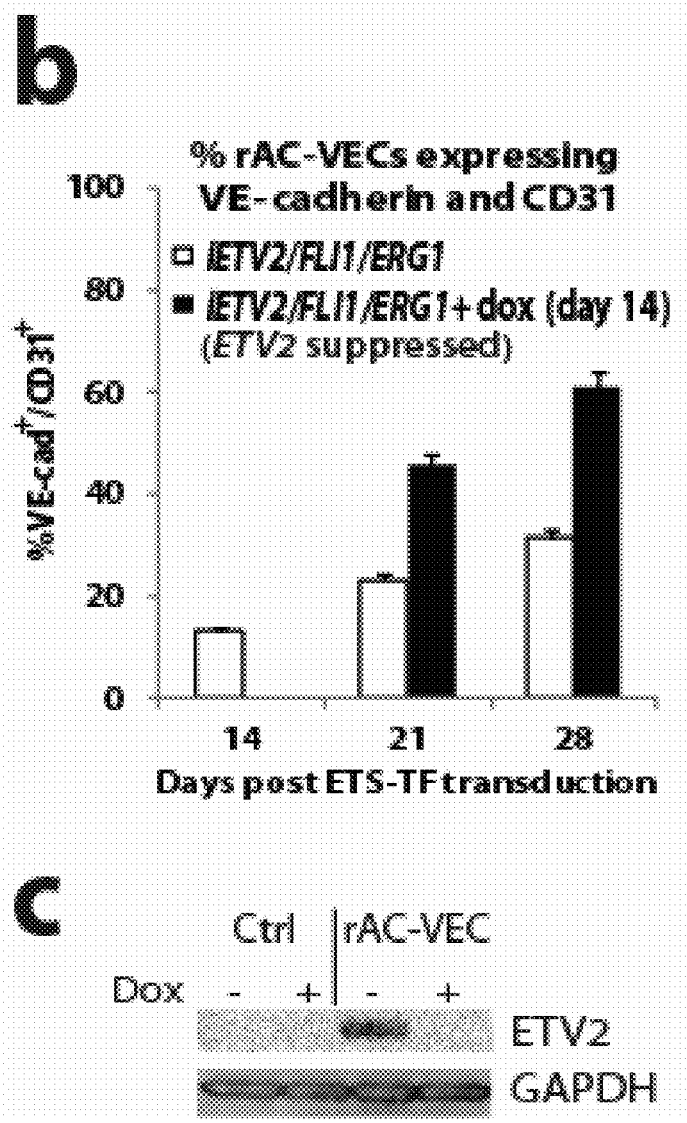
Figures 7b-c

GENERATION OF FUNCTIONAL AND DURABLE ENDOTHELIAL CELLS FROM HUMAN AMNIOTIC FLUID-DERIVED CELLS

CROSS REFERENCE TO RELATED APPLICATIONS

This application claims the benefit of priority from U.S. Provisional Application No. 61/653,185, filed May 30, 2012, and U.S. Provisional Application No. 61/709,431, filed Oct. 4, 2012, the entire contents of both of which are incorporated herein by reference.

STATEMENT REGARDING FEDERALLY SPONSORED RESEARCH OR DEVELOPMENT

This invention was made with Government Support under R01HL097797, awarded by the National Heart Lung and Blood Institute. The Government has certain rights in this invention.

INCORPOARTED BY REFERENCE OF SEQUENCE LISTING

The Sequence Listing in an ASCII text file, named 28828_5905_10_US_SequenceListing.txt of 8 KB, created on Dec. 1, 2014, and submitted to the U.S. Patent and Trademark Office via EFS-Web, is incorporated herein by reference.

FIELD OF THE DISCLOSURE

This invention relates to methods for generating functional and durable endothelial cells. In particular, this invention relates to generation of substantial amounts of bona fide endothelial cells from amniotic cells (ACs) by reprogramming ACs through enforced expression of ETS-TFs in conjunction with suppression of the TGFβ signaling pathway.

BACKGROUND ART

The generation and expansion of human endothelial cells (ECs) from readily obtainable nonvascular cell sources has great therapeutic potential for revascularization of ischemic and injured organs. However, the cultivation and expansion of stable ECs to clinically relevant scales, while maintaining their angiogenic signature, has not been achieved. Human adult-derived ECs have limited expansion potential and senesce after a few passages. Similarly, ECs derived from human embryonic stem cells (hESCs) and induced pluripotent stem cells (iPSC) have limited proliferative capacity and are phenotypically unstable, often drifting into other non-vascular lineages upon serial passaging (JAMES et al., Nat Biotechnol, 28: 161-166 (2010)). Human ECs derived from endothelial progenitor cells (EPCs) (LYDEN et al., Nat Med, 7, 1194-1201 (2001); RAFII et al., Nat Med 9: 702-712 (2003); RAFII et al., Nat Rev Cancer, 2: 826-835 (2002); JIN et al., Nat Med, 12: 557-567 (2006)) and their progeny, endothelial colony forming cells (ECFCs) have shown significant proliferative potential (INGRAM et al., Blood, 104: 2752-2760 (2004); YODER et al., Blood, 109: 1801-1809 (2007)) when grown in pooled platelet-rich plasma (REINISCH et al., Blood, 113: 6716-6725 (2009)). However, whether EPCs and ECFCs could maintain their vascular stability to enable propagation of these cells to clinical scale remains unknown. The short-comings of adult- and hESC-based strategies are likely attributable to an insufficient appreciation of the transcription factors and microenvironmental cues as well as culture conditions that are necessary for establishing and maintaining EC identity.

Several members of the E-twenty six (ETS)-family of transcription factors (TFs), including ETV2 (LEE et al., Cell stem cell, 2: 497-507 (2008); SUMANAS et al., Blood, 111: 4500-4510 (2008)), FLI1 (LIU et al., Current Bio. 18: 1234-1240 (2008)), and ERG (MCLAUGHLIN et al., Blood, 98: 3332-3339 (2001)) have been implicated in regulating vascular development and angiogenesis (DE VAL et al., Dev Cell, 16: 180-195 (2009); SATO et al., Cell Struct Funct, 26: 19-24 (2001)). These TFs directly regulate the expression of genes associated with EC development and function. Adult ECs constitutively express several ETS factors, such as FLI1, ERG (isoforms 1 and 2), ETS1, ETS2, Elf1, Elk1, VEZF and ETV6, while ETV2 is transiently expressed during embryonic development and is absent in adult ECs (KATAOKA et al., Blood, 118: 6975-6986 (2011); LELIEVRE et al., The International Journal Of Biochemistry & Cell Biology, 33: 391-407 (2001)). Although many of these TFs play key roles in vascular specification (LIU et al., Circ Res, 103: 1147-1154 (2008); PHAM et al., Dev Biol, 303: 772-783 (2007)), it is unknown whether these EC-specific TFs can also switch on endothelial genes in non-vascular cells.

Human amniotic fluid-derived cells (ACs) represent a potential source of non-vascular cells that could be amenable to reprogramming into authentic ECs. Freshly isolated ACs that are obtained from individuals with broad genetic and ethnic backgrounds, are routinely cultured from the amniotic fluid of mid-gestation human fetus for diagnostic purposes. They display high proliferative potential, can be HLA-typed, cryopreserved, and publically banked for clinical use. ACs can give rise to various cell types, including epithelial cells, mesenchymal cells and neural cells (DE COPPI et al., Nature biotechnology, 25: 100-106 (2007); Prusa and Hengstschlager, Med Sci Monit, RA253-7 (2002)). A rare subset of c-Kit$^+$ (CD117$^+$) ACs, which comprises 0.2 to 2% of the AC population, represents multipotent amniotic fluid stem cells (AFS) (ARNHOLD et al., Stem Cells Int 2011, 715341 (2011); DE COPPI et al., Nature biotechnology, 25: 100-106 (2007)) that can give rise to various cell types, including epithelial cells, mesenchymal cells and neural cells. While some of these c-Kit$^+$ cells are believed to express the pluripotent Oct-4 gene (DE COPPI et al., Nature biotechnology, 25: 100-106 (2007); PRUSA et al., Hum Reprod, 18: 1489-1493 (2003)), it is unclear whether these cells are truly pluripotent or are primarily multipotent cells. Indeed, the majority of ACs are believed to be lineage-committed cells. Three subclasses of lineage-committed ACs have been identified: Epithelioid (E-type), amniotic fluid (AF-type) and fibroblastic (F-type) (BOSSOLASCO et al., Cell Res, 16: 329-336 (2006)). E-type ACs are speculated to originate from fetal skin, while F-type cells are derived from connective tissue (Gosden, 1983; Hoehn and Salk, 1982).

Whether ACs can give rise to vascular cells has been the subject of investigation. Incubation of naïve human ACs or pre-selected c-Kit$^+$ ACs in angiogenic culture conditions has led to the generation and outgrowth EC-like cells that express a few EC-specific markers, including VE-Cadherin, VEGFR2 and CD31 and can remodel into tubule like-structures (ENAVIDES et al., Tissue Eng Part A, (2012); DE COPPI et al., Nature biotechnology, 25: 100-106 (2007); KONIG et al., Stem cells and development, 21: 1309-1320

(2012); HANG et al., *Stem cells and development,* 18: 1299-1308 (2009)). However, these EC-like cells have low proliferative potential, do not express the complete repertoire of mature EC genes, nor has it been verified that their original AC signature is erased. As such, these cells cannot be considered as authentic vascular endothelial cells.

SUMMARY OF THE DISCLOSURE

It has been discovered in accordance with this invention that enforced expression of ETS-TFs in conjunction with suppression of the TGFβ signaling pathway in amniotic cells (ACs) reprograms ACs into a proliferative population of stable vascular ECs called rAC-VECs ("amniotic cells reprogrammed into vascular endothelial cells") that have the capacity to form perfused vasculature and engraft into liver sinusoidal endothelium in vivo. Accordingly, this invention provides methods for reproducibly generating substantial amounts of endothelial cells from amniotic cells. The endothelial cells generated in accordance with the present methodology, as well as therapeutic methods utilizing these cells, are also provided.

In one aspect, this invention is directed to a method of generating endothelial cells from ACs by culturing ACs under conditions where transcription factors ETV2, FLI1 and ERG (such as ERG1 or ERG2) are expressed in the amniotic cells in the presence of a TGFβ signaling inhibitor.

In one embodiment, the ACs are cultured under conditions wherein the expression of ETV2 in the amniotic cells is transient, and the expression of FLI and ERG is constitutive. The expression of the transcription factors can be achieved based on transduction of the cells with vectors carrying nucleic acids encoding transcription factors ETV2, FLI1 and ERG, on delivering naked DNA or mRNAs encoding the transcription factors into ACs, or based on delivering polypeptide forms of these transcription factors into ACs.

In some embodiments, the TGFβ signaling inhibitor is an inhibitor specific for the type I TGFβ receptors, which can be a polypeptide comprising a soluble form of a type I TGFβ receptor, an antibody directed to a type I TGFβ receptor or ligand, or a small molecule compound.

In a specific embodiment, ACs are cultured with a transient expression of ETV2 in the amniotic cells for the first 13-15 days, in the presence of a TGFβ signaling inhibitor for the first 20-21 days, and constitutive expression of FLI1 and ERG for 21 days.

In another aspect, the invention is directed to a substantially pure population of amniotic cell-derived ECs, wherein said ECs are characterized by expression of surface markers, VE-cadherin, CD31 and VEGFR2. In one embodiment, the substantially pure population of amniotic cell-derived ECs is characterized by the presence of exogenously introduced nucleic acid encoding FLI1 in the ECs.

In a further aspect, this invention provides compositions formulated by admixing a substantially pure population of ECs generated herein and at least one pharmaceutically acceptable carrier or diluents.

In an additional aspect, the invention provides a method for repairing injured tissue in a subject by administering to the subject a composition containing a substantially pure population of ECs generated herein to promote vascularization in said tissue.

In still another aspect, this invention provides a method for treating a tumor in a subject by administering to the subject the composition containing a substantially pure population of ECs generated herein, wherein the ECs are engineered to deliver an anti-tumor agent, and upon administration, the ECs form vessels into said tumor.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

Figure 1G:
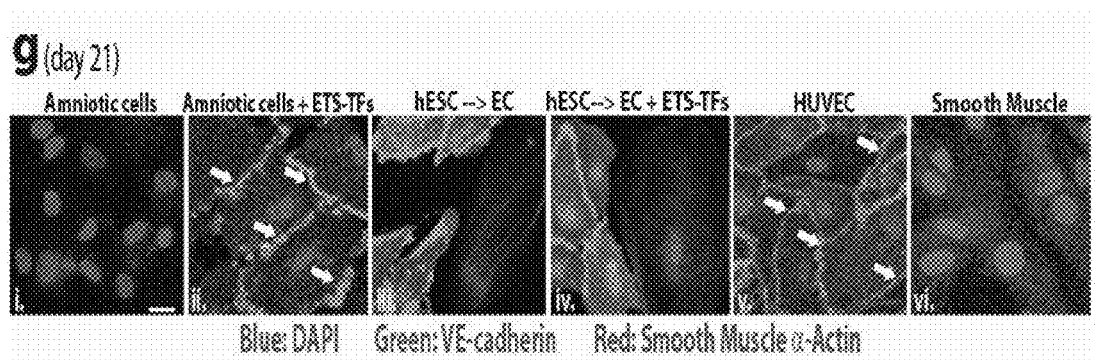
FIG. 1: Amniotic fluid-derived cells (ACs) transduced with ETS-TFs and TGFβ inhibition display a vascular phenotype that is stable and have greater proliferative potential than endothelial cells (ECs) derived from human embryonic stem cells (hESCs). a) Schematic of Vascular Endothelial Cell (rAC-VEC) reprogramming platform. ETS transcription factor (ETS-TF) transduced amniotic cells (ACs) were cultured in the presence of TGFβ inhibition (SB431542—5 µM) and assayed for expression of EC markers at weekly intervals. b) mRNA levels of EC markers (VE-cadherin, CD31, and VEGFR2) were measured over several weeks in ACs transduced with or without lentiviral vectors encoding ETV2, ERG1, and FLI1 in the presence of TGFβ inhibition. ["+"=cells transduced with ETV2, ERG1, and FLI1 lentivirus; "−"=cells transduced with equivalent doses of empty-vector lentivirus. All subsequent control ('ctrl') samples in this report were transduced with empty-vector virus unless otherwise noted]. Error bars: standard error of triplicates (VE-cadherin, VEGFR2, and CD31: *$p<0.01$ compared to control ACs for day 7-day 28). c) Cellular expansion was measured over three weeks following lentiviral transduction of ACs with (or without) ETS-TFs (ETV2, FLI1 and/or ERG1) in the presence of TGFβ inhibition (n=3, $p<0.05$ for all conditions). d) Cellular expansion was measured over seven weeks following lentiviral transduction of ACs with (or without) ETS-TFs (ETV2/FLI1/ERG1) in the presence of TGFβ inhibition (n=4 independent experiments). Fluorescence-activated cell sorting (FACS) performed at week 7 reveals over 95% of these cells express VE-cadherin. e) Cellular expansion was measured over three weeks following lentiviral transduction of ACs and hESC-derived VE-cadherin$^+$CD31$^+$VEGFR2$^+$ECs with (or without) ETV2/FLI1/ERG1 factors (ETS-TFs) in the presence of TGFβ inhibition. Error bars: standard error of triplicates (n=3, $p<0.05$). f) FACS reveals surface expression of VE-cadherin at seven-day intervals following lentiviral transduction by ETS-TFs. Error bars: standard error of triplicates. g) Immunofluorescence micrographs stained with antibodies to VE-cadherin and Smooth Muscle α-Actin are shown for ACs transduced with ETS-TFs (rAC-VECs) and hESC-derived VE-cadherin$^+$CD31$^+$VEGFR2$^+$ ECs transduced with ETS-TFs for 21 days in the presence of TGFβ inhibition. Human umbilical vascular endothelial cells (HUVECs) and smooth muscle cells serve as controls. VE-cadherin (green stain), Smooth Muscle α-Actin (red stain), DAPI (blue stain), white arrows indicate junctional staining of VE-cadherin. Scale bar—25 µm.

Cell morphology of control ACs (i.), ETV2/FLI1/ERG1 transduced ACs (ii.-v.) and HUVECs (vi.) was noted for indicated treatments with TGFβ ligands, TGFβ ligand mAb, and/or TGFβ small molecule inhibitor. Scale bar—100 μm. d) FACS reveals surface expression of VEGFR2 in ACs transduced with ETV2/FLI1/ERG1 over 21 days in the presence (black bars) or absence (clear/white bars) of persistent TGFβ inhibition. e) FACS reveals surface expression of VEGFR2 (left graph) and VE-cadherin (right graph) in ACs transduced with ETV2/FLI1/ERG1 over 28 days. Red bars: cells subjected to persistent TGFβ inhibition—EC markers were assayed for at day 14, day 21, and day 28. White bars: cells subjected to TGFβ inhibition for 14 days—EC markers were assayed for at day 21. Gray bars: cells subjected to TGFβ inhibition for 21 days—EC markers were assayed for at day 28. Error bars: standard error of triplicates.

FIG. 6: rAC-VECs establish functionally perfused vessels in vitro and in vivo. a) In vitro tube formation assay of control ACs, day 21 rAC-VECs, and HUVECs cultured in Matrigel/Endothelial Growth Media+TGFβ inhibition (SB431542) for twelve hours. Phase-contrast microscopy images of different groups are shown. Scale bar—100 μm. b) In vitro acetylated LDL (Ac-LDL) uptake assay of control ACs, day 21 rAC-VECs, and HUVECs. Cells were treated with labeled Ac-LDL (DiI label) for four hours, washed, and imaged. Scale bar—100 μm. c) In vivo tube formation assay of GFP-labeled control ACs (i., v., ix.), GFP-labeled day 42 rAC-VECs (ii., vi., x.), and GFP-labeled day 42 rAC-VECs in which TGFβ inhibition was removed at day 21 (Sample A—iii., vii., xi.; Sample B—iv., viii., xii.). Control cells and rAC-VECs were loaded separately into Matrigel plugs and implanted subcutaneously into NOD-SCIDIL2Rγ$^{-/-}$ (NSG) mice. Two weeks after implantation, mice were injected intravenously with Alexa568-Isolectin-B4 that binds to perfused vasculature to identify functional blood vessels. Ten minutes after injection, plugs were removed and sectioned. Immunofluorescence micrographs show control ACs and rAC-VECs in green (GFP), intravital labeling of perfused vasculature in red (Isolectin), and nuclear counterstain (DAPI) in blue. Scale bar—50 μm. White arrows indicate the co-localization of GFP- and isolectin-marked (anastomosed) vessels. Orange arrows indicate only isolectin-marked host mouse vessels. d and e) In vivo engraftment of day 21 rAC-VECs (GFP-labeled) into liver sinusoidal vessels of two mice. After performing 70% partial hepatectomy on NSG mice, approximately 5×10$^5$ GFP-labeled day 21 rAC-VECs were transplanted via intrasplenic route, which will drain into portal circulation and incorporate into liver vasculature. Three months following transplantation, the mice were injected with Alexa568-Isolectin-B4 to detect perfused vessels, and each liver was removed and cryosectioned. Immunofluorescence micrographs show control rAC-VECs in green (GFP), intravital labeling of perfused vasculature in red (Isolectin), human CD31 staining in cyan, and nuclear counterstain (DAPI) in blue. Liver sample #1 (d) was imaged at low magnification (i.-iv.: scale bar—50 μm). Liver sample #2 (e) was imaged at low (i.-iv.: scale bar—50 μm) and high magnification (v.-viii.: scale bar—25 White arrows indicate the co-localization of GFP-, CD31- and isolectin-marked (anastomosed) vessels. Orange arrows indicate only isolectin-marked host mouse vessels.

FIG. 7: Transient ETV2 and constitutive FLI1 and ERG1 expression, concomitant with TGFβ inhibition, generate long-lasting rAC-VECs without loss of vascular identity. a) FACS reveals surface expression of VE-cadherin and CD31 in ACs transduced with iETV2/FLI1/ERG1 for 14 (i.), 21 (ii.-iii.), and 28 (iv.-v.) days in the presence of TGFβ inhibition (SB431542). ('iETV2': inducible ETV2 lentivirus that is suppressed via treatment with Doxycycline). A subset of these cells (iii. and v.) was treated with Doxycycline at day 14 for suppression of ETV2 protein. b) Percentage of VE-cadherin$^+$CD31$^+$ cells is shown, as determined by FACS. Clear bars: no Doxycycline treatment. Black bars: Doxycycline treatment at day 14. c) iETV2 suppression by Doxycycline was confirmed by Western blot analysis. GAPDH served as a control. d). In vivo tube formation assay of GFP-labeled day 42 rAC-VECs in which iETV2 expression was suppressed at day 14. rAC-VECs were loaded into Matrigel plugs and implanted subcutaneously into NOD-SCIDIL2Rγ$^{-/-}$ (NSG) mice. Two weeks after implantation, mice were injected intravenously with Alexa568-Isolectin-B4 that binds to perfused vasculature to identify functional blood vessels. Ten minutes after injection, plugs were removed and sectioned. Immunofluorescence micrographs show rAC-VECs in green (GFP), intravital labeling of perfused vasculature in red (Isolectin), human CD31 staining in cyan, and nuclear counterstain (DAPI) in blue. Sample A was imaged at low magnification (i.-iv.: scale bar—100 μm). Sample B was imaged at high magnification (v.-viii.: scale bar—50 μm). White arrows indicate the co-localization of GFP-, CD31- and isolectin-marked (anastomosed) vessels. Orange arrows indicate only isolectin-marked host mouse vessels. e) Modular ETS-TF mediated reprogramming of ACs into abundant mature rAC-VECs. Despite implementing 'ideal endothelial cell conditions', untransduced ACs do not reprogram into rAC-VECs, nor do they proliferate (bottom panel). In the absence of TGFβ inhibition, ETS-TF transduced ACs show VE-cadherin surface expression, but fail to produce other essential EC-markers, including VEGFR2, resulting in the generation of 'VEGF-A non-responsive' endothelial-like precursors (lower pathways). Transient inhibition of TGFβ signaling for approximately 3 weeks upregulates and functionalizes VEGFR2, allowing for VEGF-A dependent signaling events to proceed (middle and upper pathways). Even though ETV2 promotes proliferation and EC-specification of ACs, when used as a singular ETS factor it does not turn on mature EC-markers, including CD31, leading to the accumulation of immature endothelial progenitor cells (middle pathway). Co-expression of FLI1/ERG1 with ETV2 along with TGFβ inhibition activates CD31 expression; however constitutive ETV2 ultimately down-regulates this mature EC-marker, resulting in the production of unstable vascular endothelium (upper pathway—low). Upon suppression of ETV2 at day 14, expression of CD31 is sustained, facilitating the generation of mature rAC-VECs (upper pathway—top). Thus, modular TGFβ inhibition and ETV2 expression along with constitutive FLI1/ERG1 co-expression provide a novel platform for reprogramming lineage-committed ACs into long-lasting functional rAC-VECs.

DETAILED DESCRIPTION

The inventors have demonstrated that enforced expression of ETS-TFs in conjunction with suppression of the TGFβ signaling pathway in amniotic cells (ACs) reprograms ACs into a proliferative population of stable rAC-VECs ("amniotic cells reprogrammed into vascular endothelial cells") that have the capacity to form perfused vasculature and engraft into liver sinusoidal endothelium in vivo. In exemplary embodiments, it is disclosed herein that constitutive expression of FLI1/ERG1 in combination with transient expression of ETV2 and TGFβ pathway inhibition in ACs not only turned on and locked in the expression of the majority of EC specific genes, but also suppressed expression of non-vascular genes. Attenuation of TGFβ signaling allows for functionalization of the VEGFR2 signaling pathway, which results in expansion of large numbers of rAC-VECs without loss of EC identity. The rAC-VECs generated herein manifest a complete angiogenic repertoire similar to adult ECs, as shown by genome-wide transcriptional profile analyses. The rAC-VECs generated herein also are able to maintain their vascular identity upon serial passaging, and to establish functional patent long-lasting vessels in immunocompromised mice. Accordingly, this invention provides methods for reproducible generation of substantial amounts of functional and stable endothelial cells from amniotic cells, the endothelial cells generated, and therapeutic use of the generated endothelial cells.

I. Amniotic Cells ("ACs")

As used herein, the term "amniotic cells" (or "ACs") refers to cells extracted from amniotic fluid, and hence also referred to herein as "amniotic fluid cells".

Although ACs are preferably isolated from human amniotic fluid, they can be isolated from amniotic fluid of other mammalian species as well. Examples of mammalian species suitable for use to collect amniotic fluid include but are not limited humans, primates, dogs, cats, goats, elephants, cattle, horses, pigs, mice, rabbits, and the like. The endothelial cells developed from ACs of a given species can be applied therapeutically to a subject of the same species.

For purposes of this invention, ACs can be extracted from amniotic fluid collected from a pregnant female during any stage of gestation. In some embodiments, amniotic fluid is collected during mid-gestation. In certain embodiments, amniotic fluid is collected during week 10-25 of a woman's pregnancy. In other embodiments, amniotic fluid is collected during the second trimester, i.e., week 14-26, of a pregnant woman. In specific embodiments, amniotic fluid is collected during week 16-21 of a woman's pregnancy.

ACs can be extracted from amniotic fluid by conventional means, for example, centrifugation. The cell pellet can be resuspended in an appropriate medium for immediate use in a reprogramming regimen disclosed herein, or resuspended in a culture medium (e.g., commercially available "Amniotic Media", exemplified herein below) and cultured for a period of time prior to reprogramming. Alternatively, the extracted ACs can be cryopreserved (and e.g., "banked") for use in the future using conventional techniques. For example, ACs, which are ready for cryopreservation, can be retrieved from culture (e.g., flasks, plates, etc.), e.g., using Accutase (EBioscience #00-4555-56), and then spun down. The cell pellet can then be resuspended in an appropriate media for cryopreservation (e.g., media consisting of 90% FBS (Omega Scientific #FB-11) and 10% DMSO (Cellgro #25-950-COC) and transferred to a cryo-tube. The cells can be stored at −80° C. for at least 3 days (initial freeze), and then transferred to liquid nitrogen (long-term freeze).

ACs are typically heterogeneous in terms of the cellular constituents, and include both multipotent cells (e.g., c-Kit$^+$ ACs) and mature ACs (c-Kit$^-$ ACs). Mature ACs include both lineage-committed and non-committed cells. The reprogramming approach disclosed herein is effective in generating rAC-VECs from extracted ACs which include both multipotent and mature cells. The reprogramming approach disclosed herein is also effective in generating rAC-VECs from mature c-Kit$^-$ ACs, including from both lineage-committed EpCam$^+$Tra1-81$^-$ c-Kit$^-$ epithelioid and EpCam$^-$Tra1-81$^-$c-Kit$^-$ non-epithelioid (mesenchymal/fibroblastic) ACs. In other words, one can reprogram extracted heterogeneous ACs directly, or reprogram a more mature subpopulation of ACs, although it is not necessary to process extracted ACs in order to isolate a more mature subpopulation for purposes of generating rAC-VECs.

II. Reprogramming ACs into rAC-VECs

As disclosed herein, ACs can be reprogrammed into a proliferative population of stable rAC-VECs ("amniotic cells reprogrammed into vascular endothelial cells"). The reprogramming involves enforced expression of transcription factors from the ETS family (ETS-TFs) in ACs in conjunction with suppression of the TGFβ signaling pathway.

II.1 Expression of ETS-TFs in ACs

In accordance with this invention, the ETS-TFs involved in the reprogramming include ETV2 (human ETV2 also known as ER71 or Estrp), FLI1, and ERG. Particular useful isoforms of ERG include ERG1 and ERG2. while other isoforms such as ERG3 and ERG4 may be suitable as well. These ETS-TFs have been described in the art (LEE et al., *Cell stem cell*, 2: 497-507 (2008); SUMANAS et al., *Blood*, 111: 4500-4510 (2008)); LIU et al., *Current Bio*. 18: 1234-1240 (2008); MCLAUGHLIN et al., *Blood*, 98: 3332-3339 (2001)), and their nucleic acid and protein sequences are also available from GenBank (ETV2: NCBI Accession No. NM_014209.2, GI: 153791177; ERG1: Accession No. NM_182918.3; GI: 209954798; ERG4: Accession No. NM_001136155.1; GI: 209954807).

It is disclosed herein that ETV2 is central for the induction of an EC fate, whereas ERG and FLI promote EC maturity. For example, ETV2 alone can turn on the expression of the vascular markers, VE-cadherin and VEGFR2, but not CD31. In contrast, ERG1 or FLI1 can activate CD31 expression, but not some other key EC markers that are turned on by ETV2.

Accordingly, the present approach of reprogramming of ACs involves enforced expression of a combination of ETV2, FLI1 and ERG in ACs. In some embodiments, the reprogramming involves enforced expression of a combination of ETV2, FLI1 and ERG1.

To achieve expression of a transcription factor in ACs, a nucleic acid encoding the transcription factor can be delivered into ACs using various vectors, which include integrative vectors which integrate into host cells genome by either random integration or targeted integration via homologous recombination, and episomal vectors that are maintained extra-chromosomally. In addition to delivery by vectors, a nucleic acid encoding a transcription factor can also be delivered to ACs in the form of mRNAs, as described in Yamamoto et al. (*Eur. J. Phar. Biophar* 71: 484-89 (2009).

Examples of delivery vectors include but are not limited to, plasmids, cosmids, viruses (bacteriophage, animal viruses, and plant viruses), and artificial chromosomes (e.g., YACs). Viral vectors include e.g., retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, and Rous sarcoma virus vectors.

In specific embodiments, a nucleic acid encoding a desirable transcription factor is delivered via a lentiviral vector. Lentiviral vectors are well known in the art (see, for example, U.S. Pat. Nos. 6,013,516 and 5,994,136) and can provide strong and sustained expression for several months.

Those skilled in the art can clone a nucleic acid encoding a transcription factor into a suitable vector using available molecular biology techniques. The vectors can include additional sequences appropriate, such as a 5' regulatory sequence (e.g., a promoter, an enhancer, or a combination thereof), a 3' transcription termination sequence, one or more origins of replication, or a selection marker. The promoter in the vector can be one naturally associated with the transcription factor, and can also be a heterologous promoter that achieves effective expression of the transcription factor in ACs. Examples of promoters suitable for use herein include, but not limited to, SV40 early or late promoters, cytomegalovirus (CMV) immediate early promoters, Rous Sarcoma Virus (RSV) early promoters, beta actin promoter, GADPH promoter, metallothionein promoter; cyclic AMP response element promoters (cre), serum response element promoter (sre), phorbol ester promoter (TPA) and response element promoters (tre).

Introduction of a nucleic acid encoding a transcription factor, such as DNA or RNA, in the form of a vector or virus, into ACs, can be achieved using various suitable methods. Such methods include, but are not limited to, liposome-mediate transfection, electroporation, calcium phosphate precipitation, DEAE-Detxan followed by polyethylene glycol, sonication loading, microprojectile bombardment, and any combination of any of the above well known techniques.

In addition to nucleic acid delivery, in some embodiments, transcription factors are provided to ACs via direct delivery of polypeptides, also referred to as protein transduction. In protein transduction, a desirable transcription factor is fused to a protein transduction domain (or "PTD") which can cross a cell membrane and delivers the fusion protein into ACs. Examples of PTDs are described in Ho et al., Cancer Research 61(2):474-7 (2001) (HIV Tat), WO03/059940 (human SIM-2), WO03/059941 (Mph), Rothbard et al. (*Nature Med.* 6(11): 1253-7 (2000), among others.

II.2 Controlled Expression of ETV2

It has been discovered by the inventors that controlled expression of ETV2 relative to FLU and ERG is important for generating mature and proliferative rAC-VECs. For example, clonal analysis reveals that stoichiometric ratios of ETV2 relative to FLI1 and ERG1 are important for generation of mature and proliferative rAC-VECs. In specific examples, both FLU and ERG1 are expressed in ideal rAC-VEC clones that express mature EC markers such as CD31, and ETV2 expression appears to be inversely proportional to CD31. Additionally, suppression of ETV2 expression after initial transient ETV2expression actually increases the percentage of mature ECs. Accordingly, the reprogramming approach can be fine-tuned such that the expression of ETV2 is controlled so as to obtain a more homogeneous population of mature ECs.

In some embodiments, the reprogramming of ACs includes a clone selection step after a period of enforced expression of the combination of ETV2. FLI1 and ERG in ACs, in order to identify clones that express at least one mature EC marker (e.g., CD31) as a result of proper stoichiometric ratios of ETV2 relative to FLI1 and ERG in the clone. For example, at about day 21 after ACs have been transduced with viral vectors encoding ETV2. FLI1 and ERG1, ACs are screened to identify clones that express not only early EC markers (e.g., VE-cadherin and VEGFR2), but also mature EC markers (e.g., CD31). Although day 21 may be a point in time when rAC-VECs are believed to have achieved maximal maturity and therefore may generate ideal clones with high efficiency, clonal expansion of rAC-VECs that have been in culture for as little as 16 days, or preferably 17 or 18 days or longer, or 19 or 20 days or longer, is also considered to be adequate to generate ideal clones.

In other embodiments, the reprogramming of ACs involves utilizing vectors and/or 5' regulatory sequences of different expression profiles (e.g., duration and strengths) to deliver and express ETV2 and FLI1/ERG, respectively, in order to achieve proper stoichiometric ratios of ETV2 relative to FLI1 and ERG in recipient ACs. For example, lentiviral vectors that direct sustained strong expression can be used for FLI1 and ERG1, and adenoviral vectors that direct relatively transient expression can be used for ETV2. Naked DNAs encoding the transcriptional factors may also be appropriate.

In still other embodiments, the reprogramming of ACs involves transient expression of ETV2, along with constitutive expression of FLI1 and ERG. In specific embodiments, transient expression of ETV2 refers to expression of ETV2 for about 10 to 18 days, 12-16 days, 13-15 days, or about 14 days. Generally speaking, a minimum of 10 days is considered to be sufficient time for ETV2 to specify amniotic cells towards an endothelial cell fate. One can assess VEGFR2 and VE-cadherin protein expression to confirm that rAC-VECs are being generated. Furthermore, as ETV2 is shown herein to negatively regulate CD31 (PECAM) expression in rAC-VECs, one can also assay for CD31 subsequent to the shutdown of ETV2. rAC-VECs positive for all three EC protein markers (VEGFR2, VE-cadherin and CD31) after ETV2 shutdown and removal of TGFβ inhibition are committed rAC-VECs.

Transient expression can be achieved by various means, including but not limited to, the use of inducible or conditional expression system (including inducible promoters), a recombinase system, and nucleic acid agents that antagonizes the production or activity of ETV2 mRNA.

In one exemplary embodiment, transient expression is achieved with the Lenti-X™ Tet-Off inducible expression system, which is commercially available from CLONETECH. Briefly, this system utilizes two lentiviral vectors: a regulator vector that stably expresses the Tet-Off transcriptional activator, and a response vector (pLVX-Tight-Pure) that controls the expression of ETV2 gene, Lentiviral particles are produced from each of the vectors and are used in co-transducing ACs. Expression of the Tet-OFF transcriptional activator from the regulator vector turns on the transcription of ETV2 from the response vector in the absence of doxycyclin. Subsequent suppression of ETV2 expression is achieved via doxycyclin treatment.

In another exemplary embodiment, transient expression of ETV2 is achieved through the use of a recombinase based system, such as Cre/Lox or FLP/FRT. The FLP protein catalyzes site-specific recombination events, and the FLP gene has been cloned from *S. cerevisiae* (Cox (1993) *Proc. Natl. Acad. Sci. U.S.A.* 80:4223-4227, incorporated herein by reference). The recombination site recognized by the FLP protein is referred to as FRT, which contains two inverted 13-base pair (bp) repeats surrounding an asymmetric 8-bp spacer: The FLP protein cleaves the site at the junctions of the repeats and the spacer. The ETV2 coding sequence can be placed in a delivery vector between two FRT sites in direct repeat orientation. After the introduction of such a vector into ACs and a period of ETV2 expression, supply of the FLP recombinase into the cells can lead to deletion of the DNA sequences between the FRT repeats and one of the FRT repeats, leaving a "scar" in the remaining FRT sequence making it illegible for further recombination by FLP. Similarly, the bacteriophage recombinase Cre catalyzes site-specific recombination between two lox sites, leading to the deletion of the sequence between the recombination sites, and with properly selected lox sequences, creation of a "scar" sequence as well. For more details of Cre recombinase, see, Hamilton et al., *J. Mol. Biol.* 178:481-486 (1984), Sternberg et al. *J. Mol. Biol.* 187:197-212 (1986), Sauer et al., *Proc. Natl. Acad. Sci.* (U.S.A.) 85.:5166-5170 (1988), and Sauer et al., *Nucleic Acids Res.* 17:147-161 (1989), all of which are incorporated herein by reference.

In other embodiments, transient expression of ETV2 is achieved by utilizing nucleic acid molecules that effectively suppress or silence the production or function of ETV2 mRNA. These include antisense RNA, siRNA, and miRNA (or "microRNA"), all of which can be designed based on the gene sequence of ETV2 and introduced into ACs.

Transient expression of ETV2 can also be achieved with naked DNA encoding ETV2 delivered into the cells.

II.3 Inhibition of TGF β Signaling

The present reprogramming approach includes inhibition of TGFβ signaling in conjunction with enforced expression of ETS-TFs. Inhibition of TGFβ signaling, at least for a short term, functionalizes VEGFR2 signaling and augments specification of ACs to rAC-VECs. By "short term" it is meant a period of at least two weeks since the commencement of reprogramming; in specific embodiments, a period of at least 18-19 days; and in other embodiments, at least 20-21 days, e.g., 20-24 days, or about 21 days. The timing of TGFβ inhibition is easily controlled for by addition of either a broad TGFβ inhibitor molecule or an antibody directed against TGFβ ligands to the culture media. VEGFR2 and VE-cadherin protein expression at the cell surface (measurable by FACS) are the two main cellular features one can examine to identify rAC-VEC generation. Once rAC-VEC fate has been established (e.g., at about 21 days), TGFβ inhibition is no longer necessary.

Inhibition of TGFβ signaling can be achieved by adding a TGFβ signaling inhibitor to the cell culture of ACs. TGFβ superfamily signaling is mediated by two classes of receptors, the type I or activin like kinase (ALK) receptors, and type II receptors. Type I receptors include ALK4 (type I receptor for activin or inhibin), ALK5 (type I receptor for TGFβ) and ALK7 (type I receptor for nodal).

In certain embodiments, TGFβ signaling inhibitors used herein are selective inhibitors of type I receptors, i.e., inhibitors having differential (i.e., selectivity) for type I receptors relative to type II receptors. Selectivity can be measured in standard assays as an $IC_{50}$ ratio of inhibition in each assay. The inhibitor can be a specific inhibitor of one type I receptor (i.e., one of ALK4, ALK5 or ALK7), or an inhibitor that inhibits signaling of several type I receptors (e.g., all of ALK4, ALK5 and ALK7).

In a specific embodiment, the inhibitor inhibits at least ALK5-mediated signaling. ALK5, upon activation, phosphorylates the cytoplasmic proteins smad2 and smad3. The phosphorylated smad proteins translocate into the nucleus and activate certain gene expression. Inhibitors of ALK5-mediated signaling can be compounds that inhibit the kinase activity of ALK5 and block phosphorylation of smad proteins. See, e.g., review by Yingling et al., *Nature Reviews* (*Drug Discovery*) 3: 1011-1022 (2004).

The inhibitors can be polypeptides, such as soluble forms of TGFβ receptors (e.g., polypeptides composed of the extracellular segment of a receptor), particularly soluble forms of type I receptors, or antibodies directed to a TGFβ receptor particularly a type I receptor or its ligand, e.g., a monoclonal antibody directed to a TGFβ ligand commercially available from R&D: #MAB1835.

The inhibitors can be small molecule compounds as well. By "small molecule compounds" it is meant small organic compounds, generally having a molecule weight of less than 1200, 1000 or 800 daltons. Small molecule inhibitors of TGFβ signaling have been well-documented in the art, including pyridyl substituted triarylimidazoles disclosed in U.S. Pat. No. 6,465,493 and US 20030149277 A1, pyridyl substituted imidazoles disclosed in US 20030166633 A1 and US 20040220230 A1, pyridyl substituted triazoles disclosed in US 20040152738 A1, thiazolyl substituted triazoles disclosed in US 20040266842 A1, 2-amino-4-(pyridin-2-yl)-thiazole derivatives disclosed in US 20040063745 A1, 2-pyridyl substituted diarylimidazoles disclosed in US 20040039198 A1, phenyl substituted triazoles disclosed in US 20050014938 A1, benzoxazine and benzoxazinone substituted triazoles in US 20050165011 A1 isoquinoline derivatives disclosed in US 20070072901 A1, thiazolylimidazole derivatives disclosed in US 20070154428 A1, heteroaromatic compounds substituted with at least one 2-pyridyl moiety disclosed in U.S. Pat. No. 7,417,041, as well as those reviewed by Yingling et al., *Nature Reviews* (*Drug Discovery*) 3: 1011-1022 (2004), the contents of all of these publications are incorporated herein by reference. Small molecule inhibitors are also available through various commercial sources. For example, compounds listed in the following table are available through Tocris Bioscience (Missouri, USA), and are suitable inhibitors for use in the present methods. Additional small molecule inhibitors are available through EMD4Bisciences (New Jersey, USA).

| Compound | Chemical Name/Function |
| --- | --- |
| A 83-01 | 3-(6-Methyl-2-pyridinyl)-N-phenyl-4-(4-quinolinyl)-1H-pyrazole-1-carbothioamide |
| | (Selective inhibitor of ALK5, ALK4 and ALK7) |
| D 4476 | 4-[4-(2,3-Dihydro-1,4-benzodioxin-6-yl)-5-(2-pyridinyl)-1H-imidazol-2-yl]benzamide |
| | (Selective CK1 inhibitor. Also inhibits ALK5) |
| LY 364947 | 4-[3-(2-Pyridinyl)-1H-pyrazol-4-yl]-quinoline |
| | (Selective inhibitor of ALK5) |
| SB 431542 | 4-[4-(1,3-benzodioxol-5-yl)-5-(2-pyridinyl)-1H-imidazol-2-yl]benzamide |
| | (selective inhibitor of ALK5, ALK4 and ALK7) |
| SB 525334 | 6-[2-(1,1-Dimethylethyl)-5-(6-methyl-2-pyridinyl)-1H-imidazol-4-yl]quinoxaline |
| | (Selective inhibitor of ALK5) |
| SD 208 | 2-(5-Chloro-2-fluorophenyl)-4-[(4-pyridyl)amino]pteridine |
| | (Potent ATP-competitive ALK5) |
| SJN 2511 | 2-(3-(6-Methylpyridine-2-yl)-1H-pyrazol-4-yl)-1,5-naphthyridine |
| | (Selective inhibitor of ALK5) |

In one embodiment, the compound, SB-431542, is used as a TGFβ signaling inhibitor. This compound is added to the culture media at a concentration ranging from about 1 µM to about 15 µM, or about 2 µM to about 10 µM. In a specific embodiment, this compound is added to the media at about 5 µM. Appropriate concentrations for other small molecule inhibitors may depend on the structure or functional mechanism of a particular inhibitor and may be in the micromolar range, which can be determined by those skilled in the art (e.g., based on IC50 values determined in appropriate in vitro assays).

II.4 Cell Culture

ACs, whether freshly extracted from amniotic fluid or thawed from a cryopreserved stock, can be maintained in culture, e.g., for 3-4 weeks, prior to reprogramming. Suitable medium for culturing ACs include high glucose Dulbecco's Modified Eagle's Medium (DMEM), DMEM/F-15, Liebovitz L-15, RPMI 1640, Iscove's modified Dubelcco's media (IMDM), and Opti-MEM SFM (Invitrogen Inc.).

After ACs are processed (e.g., transduction) for transcriptional reprogramming, the cells can be cultured in media amenable to endothelial cell growth, in the presence TGFβ inhibitor. Suitable media includes Endothelial Growth Media (EM), composed of Medium 199 (Thermo Scientific: #FB-01), 15% Fetal Bovine Serum (Omega Scientific), 20 µg/ml endothelial cell supplement (Biomedical Technologies: #BT-203), 1×Pen/Strep, 20 units/ml Heparin (Sigma: # H3149-100KU).

The cells are cultured under conditions where enforced expression of ETV2, FLI1 and ERG and simultaneous suppression of TGFβ are achieved. In specific embodiments, ACs are cultured with expression of ETV2, FLI1 and ERG1 in the presence of a TGFβ inhibitor for 12-16 days, or about 14 days, at which point, the ETV2 expression is turned off, whereas enforced expression of FLI1 and ERG1 continues in the presence of the TGFβ inhibitor until the point when the cells have been cultured for a total of 18-24 days, or about 21 days, in the presence of the TGFβ inhibitor. The TGFβ inhibitor is no longer needed in the culture from this point on, and the cells are switched over to media without the inhibitor and cultured with continued expression of FLU and ERG1 further, e.g., several days to several weeks or longer as needed.

III. Amniotic Cells Reprogrammed into Vascular Endothelial Cells ("rAC-VECs")

The term "amniotic cells reprogrammed into vascular endothelial cells" or "rAC-VECs" is used to refer to vascular endothelial cells generated from ACs using the reprogramming scheme disclosed herein, distinguished from the adult vascular endothelial cells isolated from a mammalian subject, such as human umbilical vein endothelial cells (HUVECs) and adult liver sinusoidal ECs ("LSECs"), despite the fact that rAC-VECs and adult ECs share similar morphological features, cell surface phenotypes, and transcription profiles. For example, rAC-VECs, like HUVECs, are about 10 µm length, and of a "fried-egg" or cobblestone shape. Cell surface markers characteristic of rAC-VECs include at least VE-cadherin+, VEGFR2+, and CD31+, and also optionally, EC-Selective Adhesion Molecule (ESAM) and Junctional Adhesion Molecule A (JAM-A), all of which are expressed on adult ECs. The transcriptional profile of rAC-VECs is characterized by expression of VE-cadherin, VEGFR2, CD31+, expression of angiocrine factors including BMPs, Notch-ligands, IGFs, CSFs, Kit-ligand, semaphorins, and EGFL7; lack of expression of non-EC genes such as smooth muscle actin, musclin, calponin-1, and natriuretic peptide B; and negative for hemapoietic markers including CD45, CD 15, Pu.1, TPO-receptor, Flt3 receptor or Lhx2.

Emergence of rAC-VECs in the ACs culture can be determined based on growth characteristics, morphological features, cell surface phenotypes, transcription profiles, or a combination of any of these characteristics. It is shown herein that transduction of ACs with ETV2/FLI1/ERG1 not only resulted in complete induction of a vascular signature, it also turned off non-vascular programs in ACs. rAC-VECs are highly proliferative and stable, capable of undoing $6 \times 10^4$-fold expansion in 50 days, while maintaining their full angiogenic repertoire. If desirable, rAC-VECs can be isolated from the cell culture using antibodies specific for EC surface markers, such as VE-cadherin, CD31 or VEGFR2, attached to magnetic beads or fluorophores for use in Magnetic or Fluorescence Activated Cell Sorting (MACS or FACS).

Thus, this invention also provides a substantially pure population of stable rAC-VECs. By "substantially pure" it is meant that rAC-VECs account for at least 75%, 80%, 85%, 90%, 95%, 98%, 99% or greater percentage of the cells in the cell population. By "stable" it is meant that rAC-VECs can be cultured for extended period of time, e.g., at least 5 passages, at least 10 passages, at least 15 passages or longer, without losing the characteristics of rAC-VECs.

The rAC-VECs can be used directly in therapeutic applications or cryopreserved for future use using conventional cryopreservation methods.

IV. Pharmaceutical Compositions and Therapeutic Methods

The reprogramming approach disclosed herein permits reproducible production of large numbers of functional and stable rAC-VECs, which are bankable, and can be HLA-typed, and therefore will be useful for therapeutic vascularization of injured tissues.

Accordingly, in a further aspect, this disclosure provides a composition containing rAC-VECs. The composition can include one or more pharmaceutically acceptable carriers and diluents. The composition can also include components that facilitate engraftment.

In still a further aspect, this disclosure is directed to therapeutic uses of the endothelial cells provided herein. For example, the instant endothelial cells can be used in cell therapy for the repair of ischemic tissues, formation of blood vessels and heart valves, engineering of artificial vessels, repair of damaged vessels, and inducing the formation of blood vessels in engineered tissues (e.g., prior to transplantation). Additionally, the instant endothelial cells can be further modified to deliver agents to target and treat tumors.

In specific embodiments, this disclosure provides a method of repair or replacement for tissue in need of vascular cells or vascularization. This method involves administering to a human subject in need of such treatment, a composition containing the isolated rAC-VECs to promote vascularization in such tissue.

The tissue in need of vascular cells or vascularization can be a cardiac tissue, liver tissue, pancreatic tissue, renal tissue, muscle tissue, neural tissue, bone tissue, among others, which can be a tissue damaged and characterized by excess cell death, a tissue at risk for damage, or an artificially engineered tissue.

Promoting angiogenesis in a tissue can be beneficial to individuals who have or are at risk to develop a condition including an ischemic condition, e.g., myocardial infarction, congestive heart failure, and peripheral vascular obstructive disease, stroke, reperfusion injury, limb ischemia; neuropathy (e.g., peripheral neuropathy, or diabetic neuropathy), organ failure (e.g., liver failure, kidney failure, and the like), diabetes, rheumatoid arthritis, and osteoporosis.

The rAC-VECs of this invention or a composition containing such cells can be administered in a manner that results in delivery or migration to or near the tissue in need of repair or vascularization. In some embodiments, the cells are systemically administered and circulate to the tissue in need thereof; or alternatively, locally administered, e.g., delivered directly (by injection, implantation or any suitable means) into the tissue or nearby tissue which is in need of these cells. In other embodiments, the cells are integrated into an artificially engineered tissue prior to implantation.

In another embodiment, this disclosure provides a method of targeting certain agents to tumors in a subject by administering to the subject the endothelial cells that have been engineered for delivery of such agents. Because tumors frequently stimulate the in-growth of new blood vessels into the tumor (stimulate tumor angiogenesis), endothelial cells delivered to a subject can contribute to the new tumor vasculature. Thus, the cells can be used to deliver agents directly to a tumor site. Examples of agents that can be targeted to tumors using endothelial cells include, but are not limited to, cytotoxic drugs, other toxins, radionuclides, and gene expression products. For example, endothelial cells can be engineered such that they also express a protein having anti-tumor activity, or such that they secrete, release, or are coated with a toxic agent such as a chemotherapeutic agent or radionuclide. For example, radionuclide drugs or chemotherapeutic drugs can be conjugated to an antibody that binds to the surface of the endothelial cells and thereby used to deliver the radionuclides or chemotherapeutic drugs to a tumor.

The present description is further illustrated by the following examples, which should not be construed as limiting in any way. The contents of all cited references (including literature references, issued patents, and published patent applications as cited throughout this application) are hereby expressly incorporated by reference.

EXAMPLE 1

Materials and Methods

Cell Culture

Human embryonic stem cells (hESCs) used in this study were primarily RUES 1 hESCs (provided by Dr. Ali Brivanlou, Rockefeller University). The permission for use of these cell lines were obtained after comprehensive review by the Cornell-Rockefeller-Sloan Kettering Institute ESCRO committee. The funding for execution of these studies was secured from approved non-federal funding resources. Human ESC culture medium (KOSR) consisted of Advanced DMEM/F12 (Invitrogen: #12634-028) supplemented with 20% Knockout Serum Replacement (Invitrogen: #10828-028), 1×non-essential amino acids (Gibco: #11140050), 1×L-Glutamine (Invitrogen: #25030-081), 1×Pen/Strep (Invitrogen: #15240-062), 1×β-Mercaptoethanol (Gibco: #21985023), and 4ng/ml FGF-2 (Invitrogen). Human ESCs were maintained on Matrigel™ using hESC medium conditioned by mouse embryonic fibroblasts (MEF, Chemicon) at 37° C. and 5% $CO_2$.

Amniotic cells (ACs) were obtained from the Cytogenetic Laboratory Department of Pathology at Weill Cornell Medical College. The approval for using discarded ACs (i.e. "pre-cultured ACs" were grown for 3-4 weeks in the Cytogenetic Laboratory in Amino-Max plus Supplement prior to our use) was obtained from the institutional review board at Weill Cornell Medical College. ACs were cultured at 37° C. and 5% $CO_2$ in Amniotic Media (AM): Amnio-Max (GIBCO: #17001-074)+Supplement (GIBCO: #12556-023) with 1×Pen/Strep for three to four weeks before being processed for transcriptional reprogramming. For reprogramming experiments, ACs were cultured in Endothelial Growth Media (EM): Medium 199 (Thermo Scientific: #FB-01), 15% Fetal Bovine Serum (Omega Scientific), 20 μg/ml endothelial cell supplement (Biomedical Technologies: #BT-203), 1×Pen/Strep, 20 units/ml Heparin (Sigma: # H3149-100KU), and where indicated, 5 μM TGFβ inhibitor (SB431542) or TGFβ ligand neutralizing mAb (R&D). Medium 199 Earle's Liquid Media contains an array of inorganic salts, amino acids, and vitamins, all of which can be found on the product data sheet on the ThermoScientific website. Endothelial cell supplement (aka Endothelial Mitogen—ECGS) is a partially purified preparation from bovine hypothalamus, used to improve growth of in vitro cultured vascular endothelial cells.

Liver sinusoidal endothelial cells (LSECs, ScienCell) were cultured in EM with 20% Fetal Bovine Serum. Human umbilical vein endothelial cells (HUVECs) were obtained as previously described (RAFII et al., Blood, 86: 3353-3363 (1995); RAFII et al., Blood, 84: 10-19 (1994)) and cultured in EM with 20% Fetal Bovine Serum. For ACs undergoing reprogramming, plates were coated with 1 μg/ml Fibronectin (Sigma: # F0895-5MG) and cells were grown at 37°, at 5% $CO_2$ and 5% $O_2$.

Cytokine/Small Molecule Treatment

The small molecule SB431542 (Tocris: #SB431542) was used at final concentration of 5 μM. For inducible expression/repression of ETV2 (FIG. 7), Doxycycline (Clonetech: #631311) was used at a final concentration of 2 μg/ml. For TGFβ experiments (FIG. 5), TGFβ ligands 131 (R&D: #8915) and 133 (R&D: #8425) were used at a final concentration of 10 ng/ml for indicated times. TGFβ ligand neutralizing monoclonal antibody (TGFβ mAb—R&D: #MAB1835) was used at a final concentration of 10 μl/ml. For VEGFR2 phosphorylation experiments (FIG. 5), cells were treated for 5 minutes with 50 ng/ml VEGF-A (Peprotech). For acetylated-LDL uptake assays (FIG. 6), DiI-labeled Ac-LDL (Biomedical Technical Inc.: #BT-902) was used at a final concentration of 10 μg/ml.

Lentiviral Vectors and Transduction Strategy cDNAs encoding ETV2, ERG1, and FLI1 were individually cloned into the pCCL-PGK lentivirus vector. A triple Flag-tag was subcloned into the ETV2 construct at the amino terminus, via Quick-Change Site Directed Mutagenesis Kit (Stratagene: #200521). For conditional expression/suppression experiments, Flag-tag ETV2 was re-subcloned into the pLVX-Tight-Puro vector (Clontech: #632163) and was co-transduced with pLVX-Tet-Off vector. Suppression of Flag-tag ETV2 was achieved via doxycycline (2 μg/ml) treatment. A scrambled shRNA construct was cloned into the pLKO vector for use as a control. Lentiviruses were generated by cotransfecting 15 μg of our gene of interest lentiviral vector, 3 μg of pENV/VSV-G, 514 of pRRE, and 2.5 μg of pRSV-REV in 293T cells (passage 8-10; subconfluent, 100 mm dish) by the calcium precipitation method. Supernatants were collected 40 and 64 h after transfection as previously described (NALDINI et al., Science, 272: 263-267 (1996)). Viral supernatants were concentrated by Lenti-X concentrator (Clontech: #631232) and viral titers were determined by using the Lenti-X p24 Rapid Titer kit (Clontech: #632200). Unless otherwise noted, a multiplicity of infection (MOI) of 5 was used to transduce ACs, as well as undifferentiated RUES 1 and WMC-2 hESCs.

Flow Cytometry

Flow cytometry (FACS) was performed on a Becton Dickenson LSRII SORP, and flow sorting performed on an Aria II SORP. Antibodies used were directed against human VEGFR2 (R&D: FAB357P), CD31 (eBiosciences: #11-0319-42), VE-cadherin (eBiosciences: #17-1449-42), c-Kit (BD: #339206), EpCam (BD: #347198), E-Cadherin (BD: #612130), Tra1-60 (BD: #560071), Tra1-81 (BD: #560793), CD24 (eBiosciences: #14-0247-82) and SSEA3 (BD: #560237). All voltages and compensation was performed with CompBeads (BD Pharmingen), and gating was performed on fluorophore minus one (FMO) controls.

Quantitative PCR

Total RNA was prepared from cultured cells using the RNeasy extraction kit (Qiagen: #74106) and reverse transcribed using QuantiTect Reverse Transcription Kit (Qiagen: #205313) according to the manufacturer's instructions. Relative quantitative PCR was performed on a 7500 Fast Real Time PCR System (Applied Biosystems) using SYBR Green PCR mix (Applied Biosystems). Cycle conditions were: one cycle at 50° C. for 2 min followed by 1 cycle at 95° C. for 10 minutes followed by 40 cycles at 95° C. for 15s and 60° C. for 1 minute. Primers were checked for amplification in the linear range and primer dissociation and verified. Threshold cycles of primer probes were normalized to the housekeeping gene β-Actin and translated to relative values. (See Table 1 for primer sequences.)

In Vitro Matrigel™ Tubulogenesis and In Vivo Angiogenesis Assays

To test the capacity of rAC-VECs to undergo tubulogenesis in vivo, ACs infected with ETS-TFs were transduced with GFP-lentivirus, and were mixed with Matrigel (BD: #354234), 100 ng/ml of VEGF-A, and 50 ng/ml of FGF-2, and subcutaneously implanted at the flanks of NOD.Cg-Prkde$^{scid}$I12 rg$^{tm1Wjl}$/SzJ (NSG) mice (Jackson Laboratories, Bar Harbor, Me.). To test the capacity of rAC-VECs to functionally incorporate into regenerating liver sinusoidal vasculature, GFP-labeled rAC-VECs were intrasplenically injected into NSG mice 2 days after they were subjected to 70% partial hepatectomy, as previously described (Ding et al., 2010). Two weeks (Matrigel plugs) or three months (intrasplenic) after rAC-VEC injection, the mice were injected intravenously with Isolectin-B4 conjugated with Alexa568 (Invitrogen: #I21412) (2 mg/kg), and sacrificed 10 minutes later. The Matrigel plug or liver were then fixed in 4% paraformaldehyde, followed by 48 hour saturation in 30% sucrose. 20 μm cryosections were made and counterstained with Hoechst 33342. Incorporation of GFP-labeled rAC-VECs was identified, and the functional engraftment into the host vasculature was revealed by costaining with Isolectin-B4 fluorescence. Anti-human CD31 (BD) staining was also performed to distinguish rAC-VECs from host mouse ECs. Fluorescent signal was analyzed by confocal microscopy (710 META Zeiss). The area of GFP-positive field was quantified by ImageJ, and the number of isolectin-positive functional vessels was determined by counting cells present in three fields of view taken at random. For in vitro assays, 200 μl Matrigel was coated onto 12-well TC plates, and 200,000 rAC-VECs were seeded on Matrigel, and tubulogenesis was determined as previously described (KOBAYASHI et al., *Nature cell biology*, 12: 1046-1056 (2010)).

Immunofluorescence/Western Blot Analysis

Samples were stained as previously described (James et al., 2010). Briefly, samples were permeabilized in PBST and blocked in 5% donkey serum. Samples were incubated for 1 hr with conjugated-antibodies in blocking solution, washed, and counterstained for nucleic acids by DAPI or ToPro3 (Invitrogen) for imaging by confocal microscopy. Primary antibodies used for immunostaining were VE-cadherin (R&D: #AF938), CD31 (eBiosciences: #11-0319-42), VEGFR1 (R&D: #AF321), VEGFR2 (R&D: #FAB357P), ESAM (R&D: #AF2688), JAM-A (R&D: AF1103), EpCam (BD: #347198), Smooth Muscle Actin (R&D: # MAB 1420) and Oct4 (R&D: #AF1759). All antibodies used were directed to human antigens. All imaging was performed using either a Zeiss 510 or confocal microscope. Western Blot analysis was performed as previously described (Kobayashi et al., 2010). Antibodies used in western blot assays: Flag (Sigma: # F1804-5MG-1:1000), VEGFR2 (Cell Signaling: #2479S-1:2000), pVEGFR2 (Cell Signaling: #4991-1:300), SMAD2 (Cell Signaling: #3102S-1:1000), pSMAD2 (Cell Signaling: #3108S-1:300), GAPDH (Cell Signaling: #2118L-1:5000), ERG (BioCare Medical: #CM421C-1:1000), and FLI1 (Epitomics: #3645-1-1:3000).

RNA-Seq Library Construction, Sequencing, and Analysis

Total RNA was prepared from cultured cells using the Qiagen RNeasy extraction kit and the quality was checked on an Agilent Technologies 2100 Bioanalyzer. 1 μg of high quality total RNA was used as input to convert the mRNA into a library of template molecules for subsequent cluster generation and sequencing using the reagents provided in the Illumina TruSeq RNA sample Preparation Kit (San Diego, Calif.). Following purification of the poly-A containing mRNA molecules using poly-T oligo-attached magnetic beads, the mRNA was fragmented into small pieces using divalent cations under elevated temperature. The cleaved RNA fragments were copied into first strand cDNA using reverse transcriptase and random primers. This was followed by second strand cDNA synthesis using DNA Polymerase I and RNase H. These cDNA fragments then went through an end repair process, the addition of a single 'A' base, and then ligation of the adapters. The products were then purified and enriched with PCR to create the final cDNA library. After quantifying and checking the size and purity of the product, multiplexed DNA libraries were normalized to 10 nM and then two sample libraries were pooled together in equal volumes. 7 pM of each pooled DNA library templates was amplified on Illumina cBot instrument involving immobilization and 3' extension, bridge amplification, linearization and hybridization, then sequenced on one lane of the Illumina HiSeq2000 sequencer using the pair end module and generating 2×58 bp-long reads. After QC using the Illumina pipeline, reads were mapped to the human genome (hg18) using TopHat (TRAPNELL et al., *Bioinformatics*, 25: 1105-1111 (2009)) with default parameters. RefSeq (June 2010) transcript levels (FPKMs) were then quantified using CuffLinks (TRAPNELL et al., *Nat Biotechnol*, 28: 511-515 (2010)), with upper-quartile normalization and sequence-specific bias correction. For heatmap generation, the maximum FPKM of each transcript across the samples shown was determined; FPKMs were then divided by this number to produce scaled expression values. Heatmaps were then plotted using a green-to-red color scale. Multidimensional scaling (MDS) was performed using the cmdscale function available in the R statistical software. Hierarchical clustering was performed using the average linkage approach, using the hclust R function. For both MDS and hierarchical clustering, one minus the Pearson correlation was used as dissimilarity measure between genome-wide transcriptome profiles.

DNA Profiling on Agilent 1M CGH Array

Genomic DNA was extracted from samples using a DNeasy recovery kit (Qiagen: #69506). DNA integrity was checked on a 1% agarose gel. 3 pg of DNA was then digested and labeled by random priming using Bioprime kit (Invitrogen) and Cy3 or Cy5-dUTP. Labeled DNA was hybridized to Agilent 1M CGH arrays for 40 hours at 60° C. After washing according to manufacturer's instructions, the slides were scanned in an Agilent DNA microarray scanner and images quantified using Feature Extraction 10.7 (Agilent).

EXAMPLE 2

Upregulation of ETV2, FLI1 and ERG1 Augments Differentiation of Human Embryonic Stem Cells (HESCs) into ECs To identify the ETS-TFs that are essential for the vasculogenic specification of ECs, the inventors used an established model of hESC differentiation into embryonic ECs (JAMES et al., *Nat Biotechnol*, 28: 161-166 (2010)). Using microarray profiling, the inventors found that ETV2, FLI1 and ERG were key ETS-TFs that were expressed during differentiation of hESCs into ECs. The ERG1 isoform showed a consistent expression in prototypical ECs compared to the ERG2 isoform, so ERG1 was used in protocols for generation of ECs from hESCs.

hESCs were incubated with BMP2 and VEGF-A for 10 days to generate VEGFR2$^+$VE-cadherin$^-$ cells, which are vascular precursors of early embryonic ECs. Subsequently, VEGFR2$^+$CD31$^-$ VE-cadherin$^-$ cells were isolated and transduced with lentiviral vectors expressing cDNA for ETV2, FLI1, and ERG1 (ETV2/FLI1/ERG1) or control virus. After expansion of cells with VEGF-A, FGF-2, and the TGFβ inhibitor SB431542, a modest increase was observed in VEGFR2$^+$CD31$^+$VE-cadherin$^+$ ECs among ETS-TF transduced cells compared to control cells. However, both ETS-TF transduced and untransduced VEGFR2$^+$CD31$^+$VE-cadherin$^+$ ECs failed to proliferate beyond 3 weeks and eventually transdifferentiated into non-EC cell types such as smooth muscle cells. Therefore, despite enforced expression of ETS-TFs, hESC-derived ECs were unable to sustain their proliferative potential and EC identity.

EXAMPLE 3

Amniotic Cells Reprogrammed into Vascular Endothelial Cells (rAC-VECS) Manifest Greater Proliferative Capacity and Vascular Stability than Ecs Derived from Ets-Transduced Hescs As hESC-derived embryonic ECs have limited expansion potential and upon passaging 'drift' into non-vascular cells, the inventors searched for a source of readily accessible human cells that could be reprogrammed into vascular cells. Attempts to reprogram adult human fibroblasts and mesenchymal cells were unsuccessful (data not shown). After screening a large number of human fetal and adult tissues, the inventors observed that mid-gestation amniotic cell (AC)-derived mesenchymal and epithelial cells were amenable to reprogramming into vascular endothelial cells (rAC-VECs) with unexpectedly high efficiency. To this end, ACs ('pre-cultured ACs'—see Methods) were transduced with lentiviral ETS-TFs (ETV2, FLI1, ERG1) singularly and in combination to determine whether these cells could be reprogrammed into rAC-VECs (FIG. 1a). As TGFβ inhibition is critical in preventing EC to mesenchymal transition (Endo-MT) of embryonic ECs derived from hESCs (JAMES et al., *Nat Biotechnol*, 28: 161-166 (2010)), ACs were also cultured in the presence of a TGFβ receptor inhibitor, SB431542, or neutralizing monoclonal antibodies (mAbs) to TGFβ ligands.

Transduction of ACs with lentiviruses encoding ETV2, FLI1 or ERG1 led to measurable levels of corresponding mRNA and protein expression for several months. Expression levels of the vascular markers VE-cadherin, VEGFR2, and CD31 were assessed to evaluate reprogramming efficiency of transduced ACs. ETV2 alone switched on the expression of the vascular markers, VE-cadherin and VEGFR2, but did not activate CD31. In contrast, ERG1 or FLI1 activated CD31 expression, but failed to induce other key EC markers that were turned on by ETV2. Thus, ETV2 is central for the induction of an EC fate whereas ERG1 and FLI1 promote EC maturity. Notably, ACs transduced simultaneously with all three ETS-TFs displayed strong induction of each EC marker within 7 days and lasting for beyond one month thereafter (FIG. 1b), suggesting that a combination of these factors is necessary to activate the full-compliment of genes associated with EC identity and maturity. Expression of ETS-TFs also promotes expansion of transduced ACs, as transduction with ETV2 alone conferred the highest growth rate, while FLI1 or ERG1 transduced cells proliferated poorly (FIG. 1c). Enforced expression with all three ETS-TFs bestowed rAC-VECs with robust proliferation. Starting with $10^5$ ACs transduced with ETV2, FLI1 and ERG1 (ETV2/FLI1/ERG1), nearly 30 million cells grew out by week 3, and increased to over 6 billion cells by week 7 (FIG. 1d). Notably, VE-cadherin surface expression was retained in over 98% of ETV2/FLI1/ERG1 transduced ACs throughout this time period.

Following transduction with ETS-TFs and TGFβ inhibition, ACs expanded to numbers nearly 30-fold higher than ETS-TF transduced or untransduced hESC--->ECs (FIG. 1e). Furthermore, a noticeable decrease in VE-cadherin$^+$ cells is seen over successive passages of ETS-TF transduced or untransduced hESC-derived ECs compared to ACs transduced with ETS-TFs (FIG. 10. This 'drift' away from an EC phenotype within the hESC-derived EC population was verified by staining with Smooth Muscle α-Actin (SMA) antibody (FIG. 1g—boxes iii., iv., and vi.). ACs transduced with ETS factors are negative for this non-EC marker (FIG. 1g—box ii.); rather, they exhibit the typical VE-cadherin expression pattern found on other adult EC types, such as human umbilical vein endothelial cells (HUVECs: FIG. 1g—box v.) and liver sinusoidal ECs. Thus, ACs are endowed with a unique epigenetic constitution that is more amenable to transcriptional reprogramming into stable ECs than hESCs.

EXAMPLE 4

ACs are Devoid of EC Precursor Cells

Figure 2A:
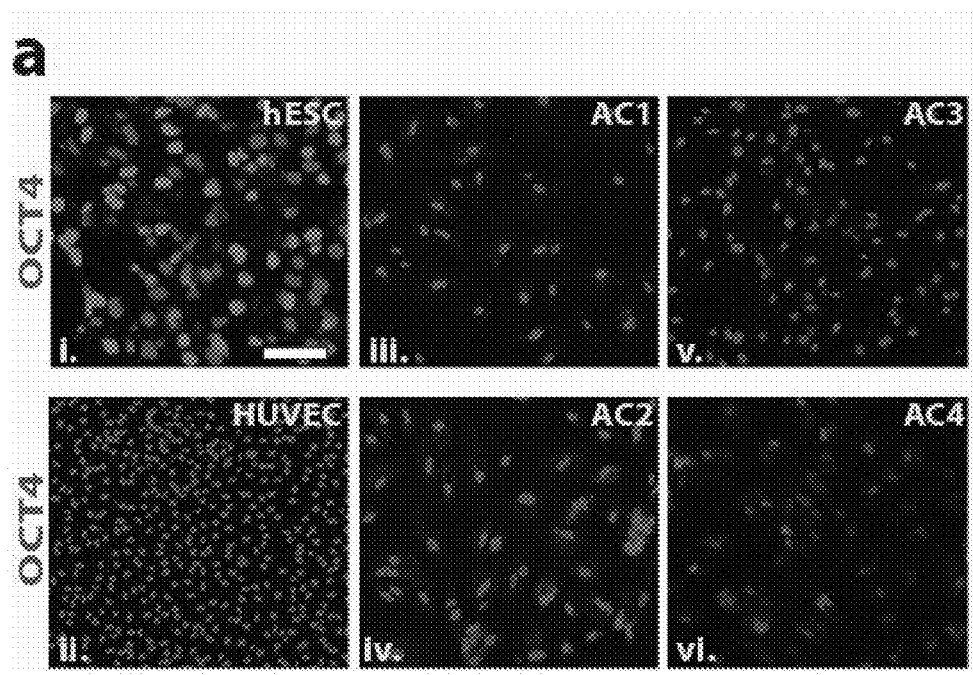
FIG. 2: The majority of lineage committed Tra1-81$^-$c-Kit$^-$ mature epithelioid and mesenchymal/fibroblastic ACs are reprogrammable into rAC-VECs. a) Human ESCs (hESCs) (i.), HUVECs (ii.), and four independent AC samples (AC1 to AC4) (iii.-vi.) were stained for OCT4 protein (pink). Scale bar—100 µm. b) Relative levels of OCT4 mRNA (upper graph) and SOX2 mRNA (lower graph) were measured in hESCs, HUVECs, and three independent AC samples (AC1, AC5, AC6). For hESC data, red bars represent y-axis scale on left side of graph. For AC and HUVEC data, blue bars represent y-axis scale on right side of graph. Error bars: standard error of triplicates (OCT4 and SOX2: *p<0.002 compared to ACs and to HUVECs). c) FACS of ACs indicate presence of both lineage-committed and uncommitted cell types in the AC population. One representative cell-line is depicted (i.-iv.). Specific markers tested are indicated on 'x' and 'y' axes, with corresponding levels described as percentage of total cell population. Chart (right panel) displays mean values for percentage of cells expressing designated markers across fifteen independent AC samples (SE: Standard Error). d) (top graph) Cellular expansion was measured over four weeks following lentiviral transduction of EpCAM⁺Tra1-81⁻c-Kit⁻ and EpCAM⁻Tra1-81⁻c-Kit⁻ ACs with ETS-TFs (ETV2/FLI1/ERG1) in the presence of TGFβ inhibition (SB431542). (bottom graph) FACS reveals surface expression of VE-cadherin for EpCAM⁺Tra1-81⁻c-Kit⁻ and EpCAM⁻Tra1-81⁻c-Kit⁻ ACs transduced with ETS-TFs for 28 days in the presence of TGFβ inhibition (n=3, P<0.05). e) Immunofluorescence micrographs are shown for EpCAM⁺Tra1-81⁻c-Kit⁻ ACs transduced with ETS-TFs for 28 days in the presence of TGFβ inhibition. EpCAM (red stain), VE-cadherin (green stain), DAPI (blue stain). Scale bar—25 µm.
Figure 2B:
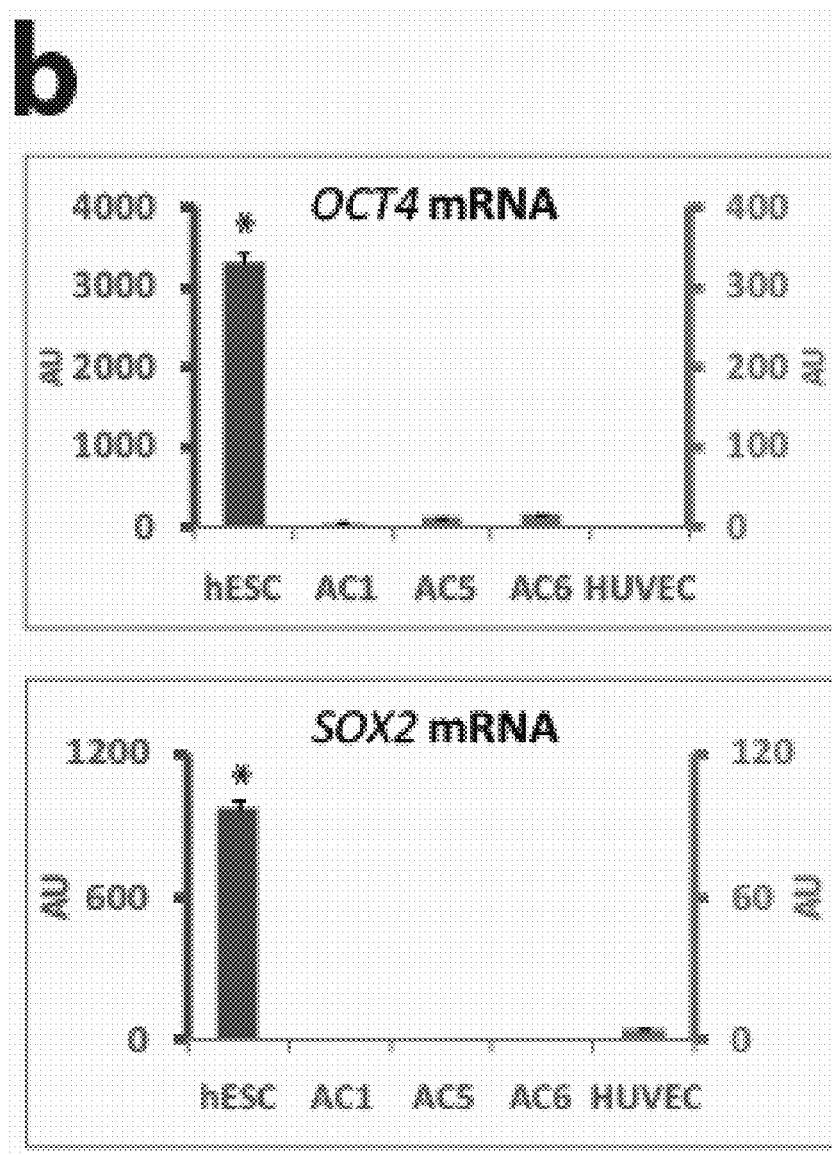

To assess whether AC-derived rAC-VECs grew out from a pre-existing EC precursor cell, the inventors tested whether rAC-VECs could be generated by culturing ACs in conditions sufficient for EC expansion in the absence of ETS-TFs. ACs were grown in optimal EC growth media (EM) containing VEFG-A, FGF-2, EGF, and IGF, in the presence and absence of the TGFβ inhibitor, SB431542 under normoxic conditions (SIMON et al., *Nature reviews Molecular cell biology*, 9: 285-296 (2008)). By day 14, VE-cadherin and CD31 expression was still absent in these untransduced ACs. Further treatment of ACs for 21 days and beyond in culture conditions that foster EC proliferation resulted in cell-death (data not shown). Thus, rAC-VECs are not the product of a pre-existing EC progenitor. Subsets of ACs, such as c-Kit$^+$cells, which constitute approximately 0.2 to 2% of the AC population, have been shown to be multipotent (DE COPPI et al., *Nature biotechnology*, 25: 100-106 (2007)). To exclude the possibility that rAC-VECs are borne out solely from a multipotent sub-population of ACs, the inventors assessed the presence of the pluripotency marker OCT4 in ACs. The overwhelming majority of the AC population was negative for OCT4 protein (FIG. 2a), confirming similar results from other groups (JEZIERSKI et al., *Stem cell reviews*, 6: 199-214 (2010)). Nearly undetectable mRNA expression levels for OCT4 (FIG. 2b—top panel) and SOX2 (FIG. 2b—bottom panel) as well as NANOG (data not shown) further suggest that few ACs, except possibly small subsets of c-Kit$^+$ cells, are multipotent. Thus, the great majority of the ACs are devoid of EC precursor or multipotent cells that could spontaneously differentiate into abundant authentic vascular cells without transduction with ETS-TFs.

EXAMPLE 5

Lineage-Committed Epithelioid and Mesenchymal/Fibroblastic ACs are Conducive to Reprogramming into rAC-VECs ACs are composed of both lineage-committed cells, phenotypically marked as E-Cadherin$^+$ (E-Cad, CD324), EpCAM$^+$ (CD326), and CD24$^+$ cells, as well as undifferentiated cells expressing c-Kit, Tra1-60, Tra1-81, SSEA-3 and SSEA-4 (FIG. 2c). Notably, c-Kit$^+$ make up<1% of ACs (DE COPPI et al., Nature biotechnology, 25: 100-106 (2007)), while CD31$^+$ cells were absent.

Figure 2E:
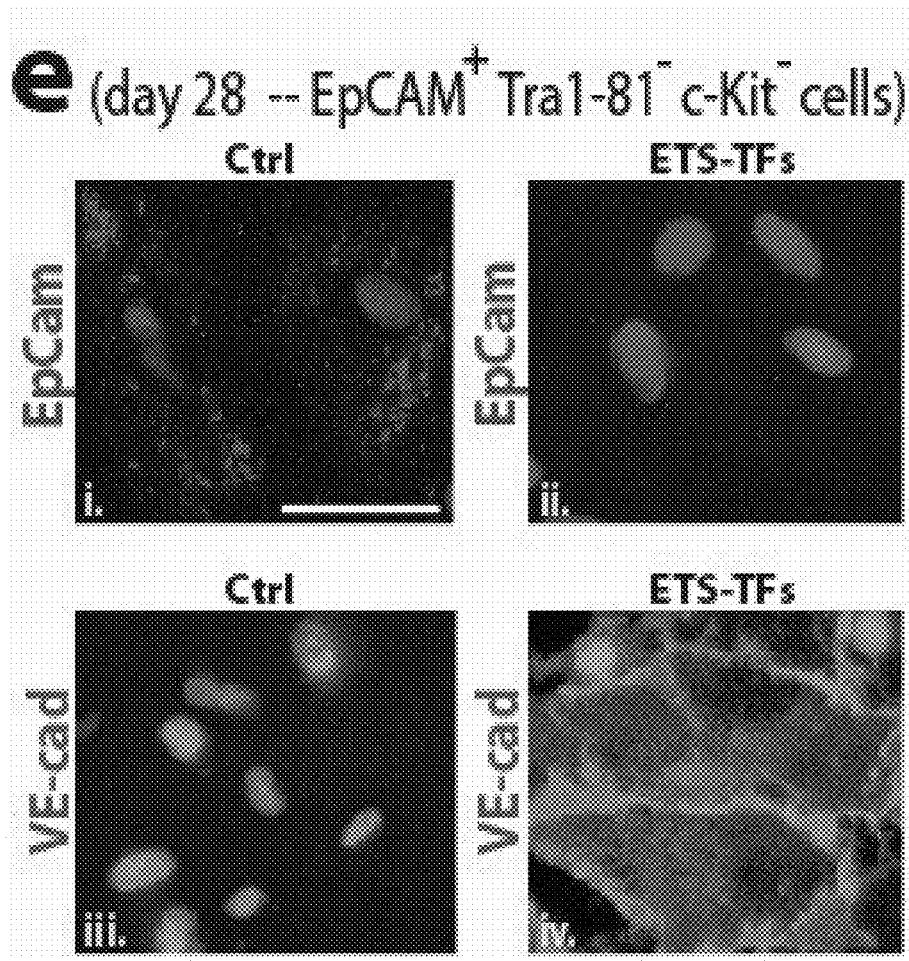

As the number of c-Kit$^+$ cells is prohibitively small, the inventors hypothesized that non-multipotent lineage-committed ACs are the primary source for generating rAC-VECs. After depleting c-Kit$^+$cells from the AC pool, EpCAM$^+$Tra1-81$^-$ c-Kit$^-$ cells and EpCAM$^-$ Tra1-81$^-$ c-Kit$^-$ cells were purified, transduced with ETS-TFs and propagated in the presence of TGFβ inhibition. Both ETS-TF transduced subpopulations proliferated well over 4 weeks of culture (FIG. 2d—top graph). Furthermore, a significant increase of VE-cadherin$^+$cells among the ETS-TF transduced EpCAM$^+$Tra1-81$^-$ c-Kit$^-$ and EpCAM$^-$ Tra1-81$^-$ cKit$^-$ subpopulations was observed (FIG. 2d—bottom graph). Immunocytostaining for EpCAM and VE-cadherin protein confirms the transition from an epithelioid-type AC to an rAC-VEC as a result of ETS-TF transduction and TGFβ inhibition (FIG. 2e). Therefore, it is the lineage-committed ACs that are amenable to reprogramming into rAC-VECs.

EXAMPLE 6

ETS-TFs Activate Expression of a Vascular Signature in ACs

Figure 3A:
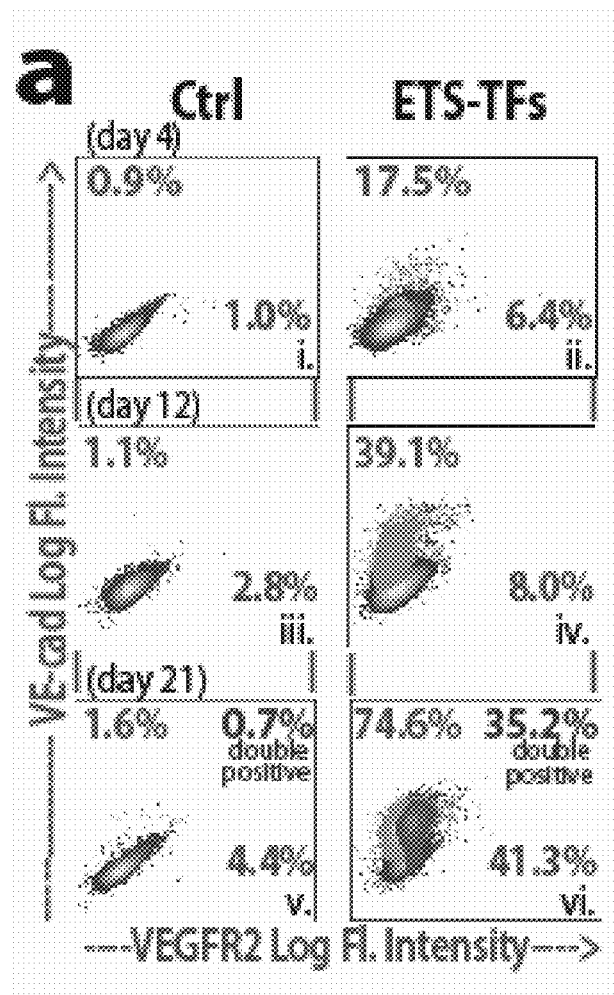
FIG. 3: ETS-TF transduced ACs (rAC-VECs) activate expression of EC-specific genes, and rAC-VECs undergoing clonal expansion delineate optimal stoichiometric ratios of ETV2, ERG1, and FLI1 for generation of mature proliferative rAC-VECs. FACS analysis reveals VE-cadherin (VE-cad) and VEGFR2 surface expression on the emerging rAC-VECs at 4 days (a: ii.), 12 days (a: iii.-iv.), 21 days (a: v.-vi.), and 28 days (b: i.-ii.) following transduction with indicated ETS-TFs (ETV2/FLI1/ERG1) in the presence of TGFβ inhibition (SB431542). HUVECs used as a positive control (b: iii.). The morphology (b: iv.-vi.) and size (b: vii.-ix.) of the emerging rAC-VECs approximated those of ECs, such as HUVECs. Scale bar—50 µm. c) Schematic of single-cell clonal expansion protocol: ACs were transduced with ETS-TFs in the presence of TGFβ inhibition, and cultured for three weeks. At day 21, VE-cadherin⁺VEGFR2⁺CD31⁺ cells were isolated with monoclonal antibodies (mAb) to VE-cadherin, VEGFR2, and CD31. Automated single-cell plating of VE-cadherin⁺VEGFR2⁺CD31⁺ cells was performed into a 96-well format for clonal expansion for several weeks. On average, 20 to 25% of the individual plated cells formed colonies. d) Representative example of clonal single cell expansion over three weeks following VE-cadherin⁺VEGFR2⁺CD31⁺ isolation (day 21 through day 42). Scale bar—100 µm. e) FACS analysis of specific rAC-VEC Clone-1, Clone-2, and Clone-3 (boxes ii.-iv.) reveals VE-cadherin (VE-cad), VEGFR2 and CD31 surface expression at day 42 of clonal expansion protocol (i.e. 3 weeks post VE-cadherin⁺VEGFR2⁺CD31⁺ isolation). Cellular expansion of rAC-VEC clones was measured from time of single-cell plating ('day 21' of clonal expansion protocol) over subsequent 5 weeks (box v.). Expression levels for ETS-TFs (ETV2, FM, and ERG1) of rAC-VEC clones at day 42 of clonal expansion protocol are shown (boxes vi.-viii.).
Figure 3B:
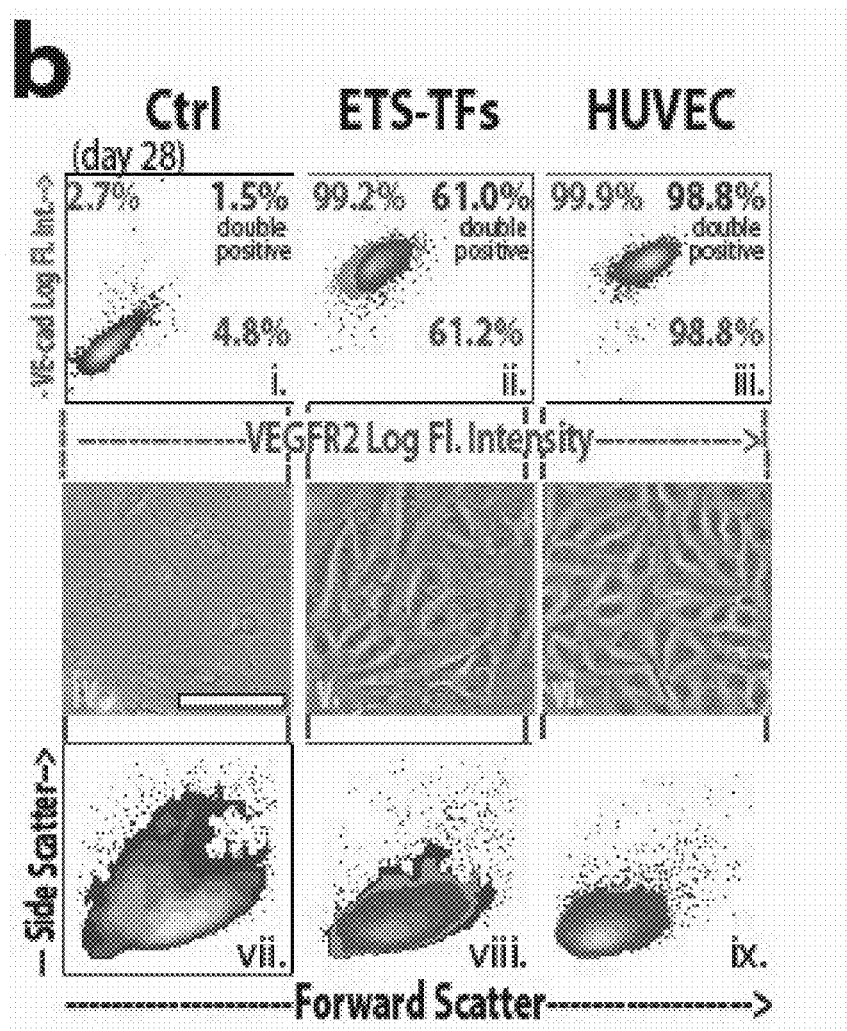

To assess the extent to which rAC-VECs acquire a vascular signature, the inventors measured VE-cadherin and VEGFR2 surface expression on emerging rAC-VECs (FIG. 3a). Four days after transducing TGF-β inhibited ACs with ETS-TFs, VE-cadherin$^+$ cells and to a lesser extent VEGFR2$^+$cells have been generated (FIG. 3a—box ii.). The percentage of cells expressing these markers increased significantly over several weeks (FIG. 3a—boxes iv. and vi.), such that after 4 weeks of reprogramming, the entire population (~99%) of transduced ACs were VE-cadherin$^+$ (FIG. 3b—box ii.) of which nearly two-thirds also show VEGFR2 expression. In addition, these switched cells were now morphologically similar to HUVECs (FIG. 3b—boxes iv.-ix.). Since the reprogramming approach utilized lentiviral-dependent integration of cDNA into the host genome, the inventors performed Comparative Genomic Hybridization (CGH) analysis to assess the genomic integrity of day 28 rAC-VECs. This analysis revealed no genomic abnormalities, demonstrating that proliferating rAC-VECs are genetically stable.

EXAMPLE 7

Figure 3C:
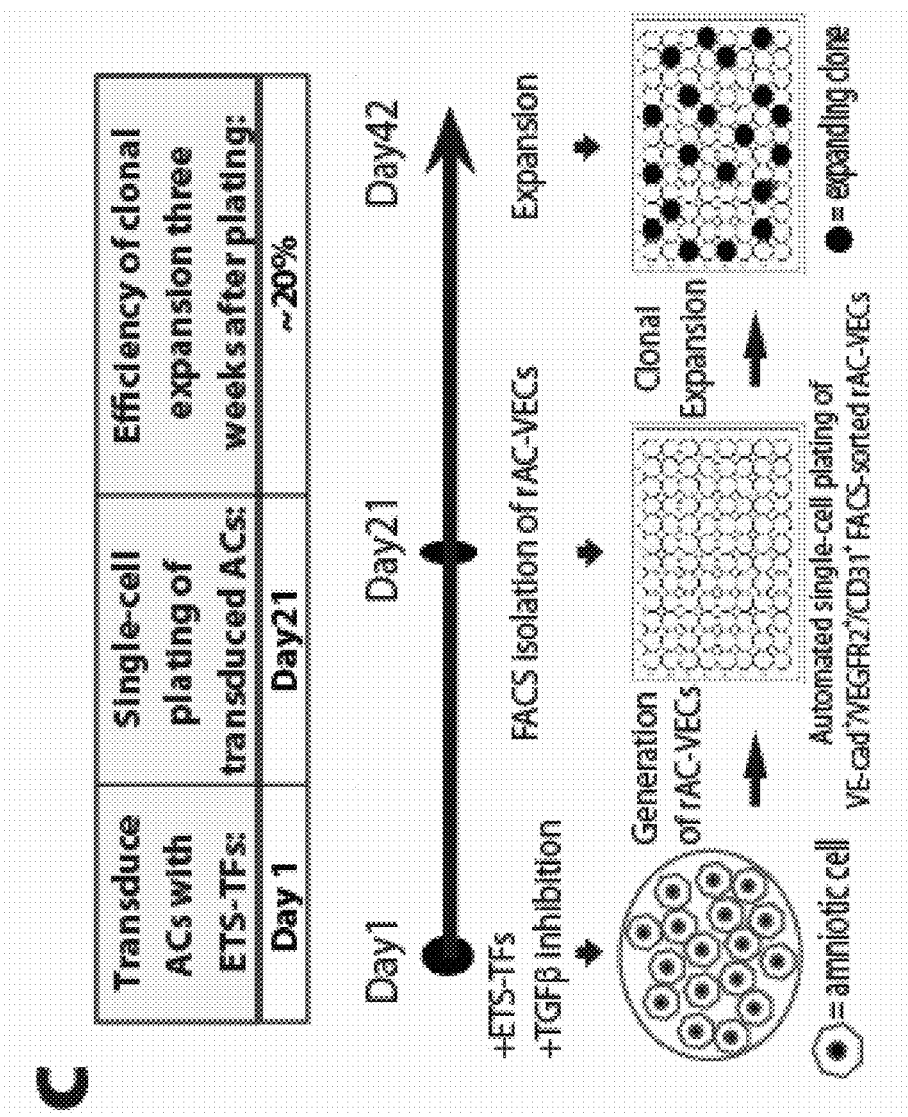
Figure 3D:
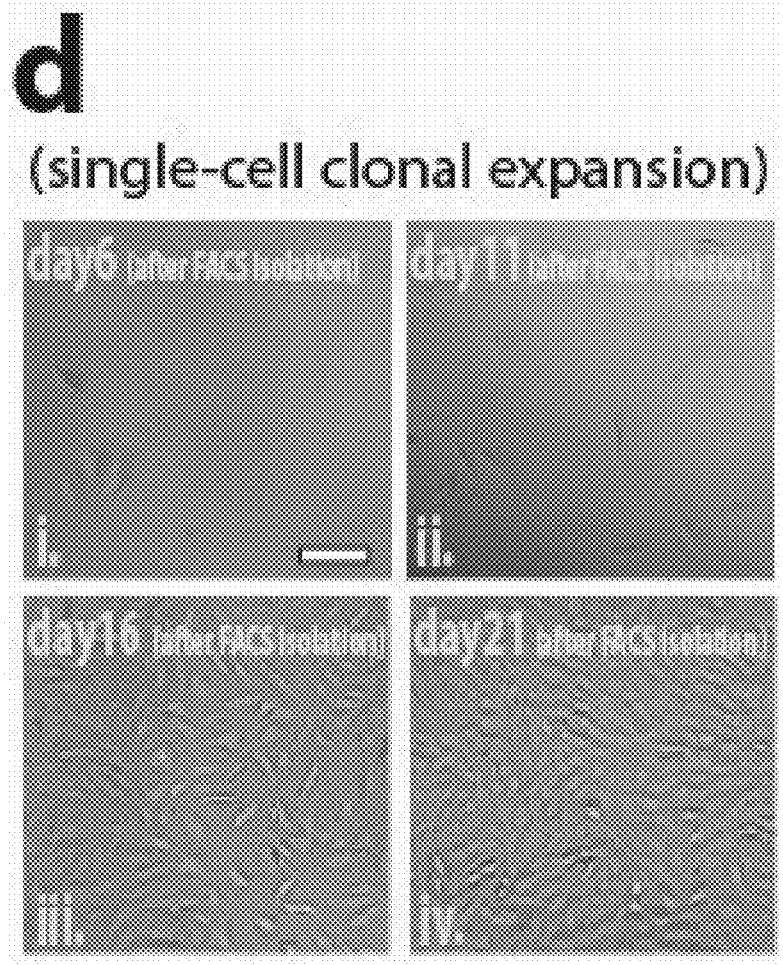
Figure 3E:
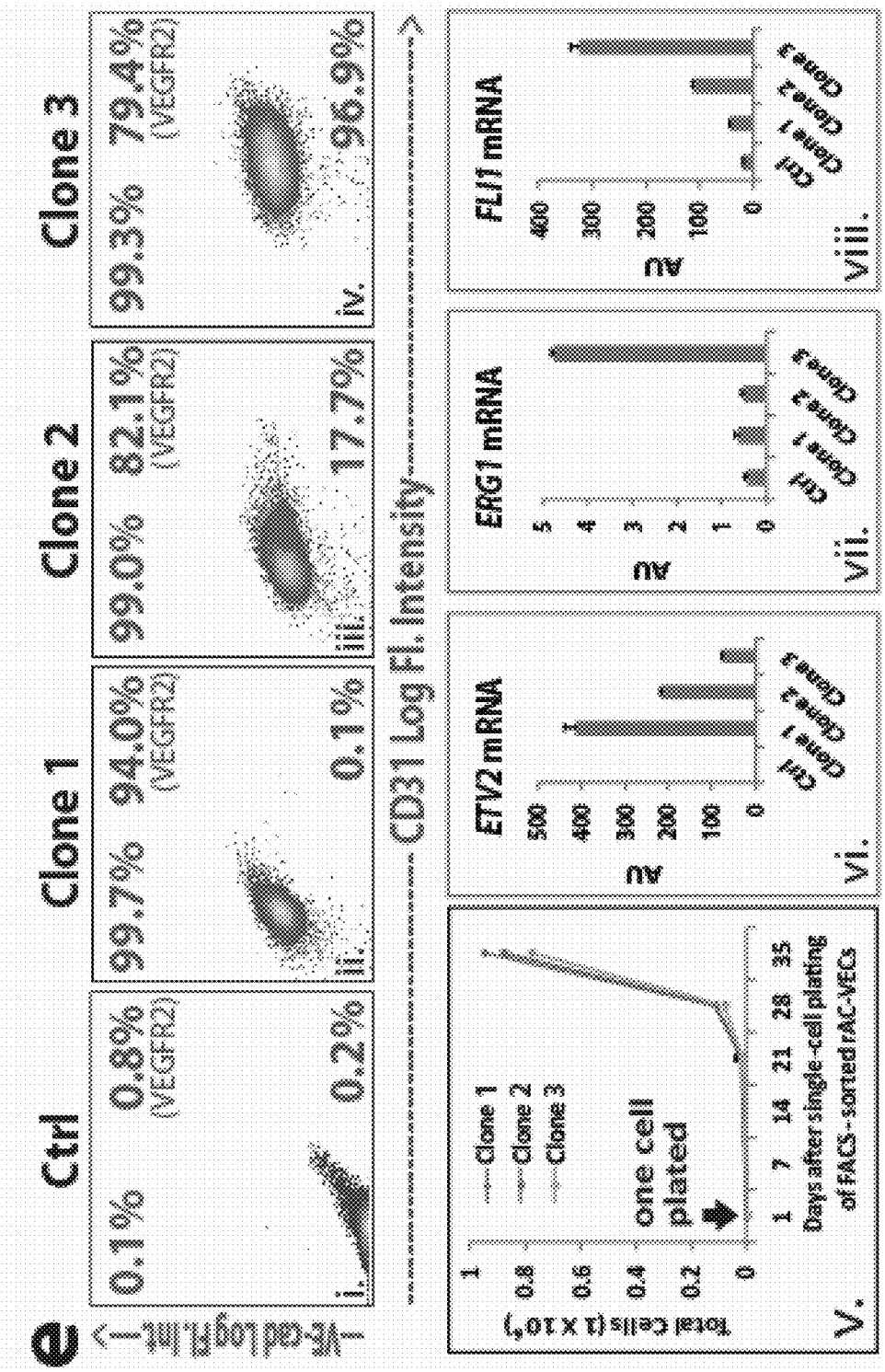

Optimal Stoichiometry of ETS-TF Expression is Necessary to Generate Mature rAC-VECs Although the majority of d21 rAC-VECs were VE-cadherin$^+$, it was unclear whether these cells were composed of clonal or heterogeneous populations of mature and immature rAC-VECs. In order to generate a homogenous population of mature rAC-VECs expressing a complete EC program, the inventors performed clonal analyses at the onset of the reprogramming process. rAC-VECs were generated from ACs by transduction with ETV2/ERG1/FLI1 and TGFβ inhibition and were cultured for 21 days. Single cells were then isolated which expressed VE-cadherin, VEGFR2 and CD31 (VE-cad$^+$VEGFR2$^+$CD31$^+$) and plated at a density of one cell per well in 96-well plates for clonal expansion (FIG. 3c). Within 21 days, 20-25% of single-cell clones showed expansion potential (FIG. 3d), with individual clones yielding progeny with non-identical phenotypes (FIG. 3e—boxes i.-iv.). While Clone-1, Clone-2, and Clone-3 were all nearly 99% VE-cadherin+, CD31 expression varied greatly. Notably, Clone-3 cells expressed CD31, whereas Clone-1 yielded no CD31$^+$cells and Clone-2 produced both CD31+ (18%) and CD31$^-$ cells. Regardless of CD31 expression, all three clones were able to expand beyond 4 weeks (FIG. 3e—box v.).

As these differences in EC marker induction among various clones could be due to stoichiometry of ETS-TF expression, mRNA levels of ETV2, ERG1, and FLI1 mRNA were assessed (FIG. 3e—boxes vi.-viii. and summary). Both ERG1 and FLI1 were expressed in Clone-3, suggesting these factors are important for inducing CD31 expression. Furthermore, ETV2 expression was inversely proportional to CD31, indicating that ETV2 negatively regulates CD31. Thus, Clone-3 appeared to have the appropriate combination of ETS-TF expression to turn onVE-cadherin, VEGFR2 and CD31. Therefore, the reprogramming platform described thus far generated a population of rAC-VECs whose heterogeneity was attributable to varied expression levels of ETS-TFs.

Figure 4A:
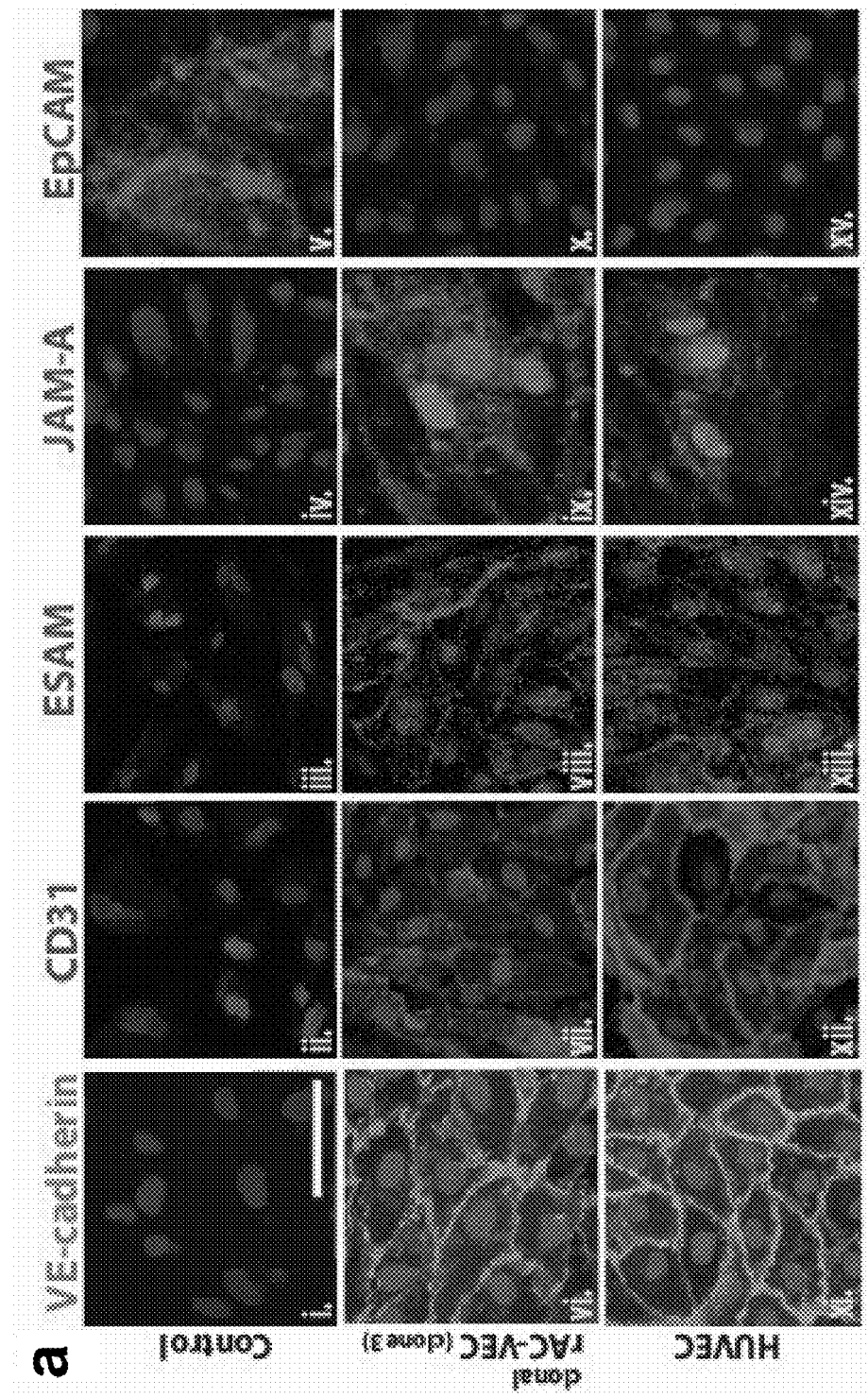
FIG. 4: ETS-TF transduction results in reprogrammed ACs that display a global change in gene expression that matches the transcriptome of mature ECs, while simultaneously demonstrating erasure of its original AC identity. a) Immunofluorescence micrographs are shown for control (ctrl) ACs, clonal rAC-VECs (Clone-3-day 42) and HUVECs. VE-cadherin (green stain: i., vi., xi.), CD31 (red stain: ii., vii., xii.), ESAM (red stain: iii., viii., xiii.), JAM-A (red stain: iv., ix., xiv.), EpCAM (red stain: v., x., xv.). DAPI (blue stain). Scale bar—50 µm. b) RNA-seq was performed on ACs transduced with ETS-TFs for approximately 2 months ('rAC-VEC') in the presence of TGFβ inhibition (SB431542). Additionally, two rAC-VEC clones ('rAC-VEC Clone-3' and 'rAC-VEC Clone-4') cultured for approximately 2 months in the presence of TGFβ inhibition underwent RNA-seq analysis. rAC-VEC Clone-4 has a similar ETS-TF expression profile to that of rAC-VEC Clone-3 (data not shown). These rAC-VEC samples were compared to human umbilical cord-blood derived CD34⁺ cells ('CD34⁺'), human bone marrow stromal cells ('BMS'), naïve human ACs ('Amni ctrl'), human lung small airway epithelial cells, HUVECs ('HUVEC') and LSECs ('LSEC'). A heat-map of relative transcription levels is shown, depicting 1) vascular expressed genes turned on in rAC-VECs, 2) non-vascular expressed genes silenced in rAC-VECs, and 3) the pattern of the expression of TGFβ family gene in rAC-VECs, relative to the aforementioned cell types. c) Three dimensional MDS plots (3D MDS): for this analysis, the inventors calculated all pairwise distances between the global transcriptome-wide RNA-seq profiles of the samples shown here. Distances were defined as one minus the Pearson correlation between two profiles. The inventors then used multidimensional scaling (MDS) to identify the set of points in 3D space such that the distances between the points are approximately equal to the true distances between samples. This analysis shows a tight colocalization of rAC-VECs (clonal and non-clonal derived) with HUVECs and LSECs, thus indicating that their genome-wide expression profiles are highly similar. On the other hand, other non-vascular cell types such as BMS, epithelial cells, and CD34⁺ hematopoietic cells are located farther away and show no similarities to rAC-VECs. Two different angles of view were shown for the same 3D-MDS analysis in order to better capture the 3D relationships between the different samples studied in this figure. Importantly, this analysis was not biased towards any gene set or processes: all >30,000 RefSeq transcripts whose expression was quantified by RNA-seq were used to calculate distances between samples.

To evaluate whether rAC-VEC clones manifest a similar angiogenic profile as mature vascular committed ECs, the inventors performed immunostaining with a series of antibodies directed against mature EC markers. In addition to VE-cadherin and CD31, Clone-3 also stained positive for EC-Selective Adhesion Molecule (ESAM) and Junctional Adhesion Molecule-A (JAM-A) (FIG. 4a). The disappearance of EpCam in rAC-VECs (FIG. 4a) indicates that the original non-vascular signature of these cells was being stripped away. Thus, the differential expression levels of ETS-TFs were critical in generating rAC-VECs capable of maintaining their EC identity as they mature.

EXAMPLE 8

Clonally derived rAC-VECs display a transcriptome profile similar to mature ECs

Figure 4B:
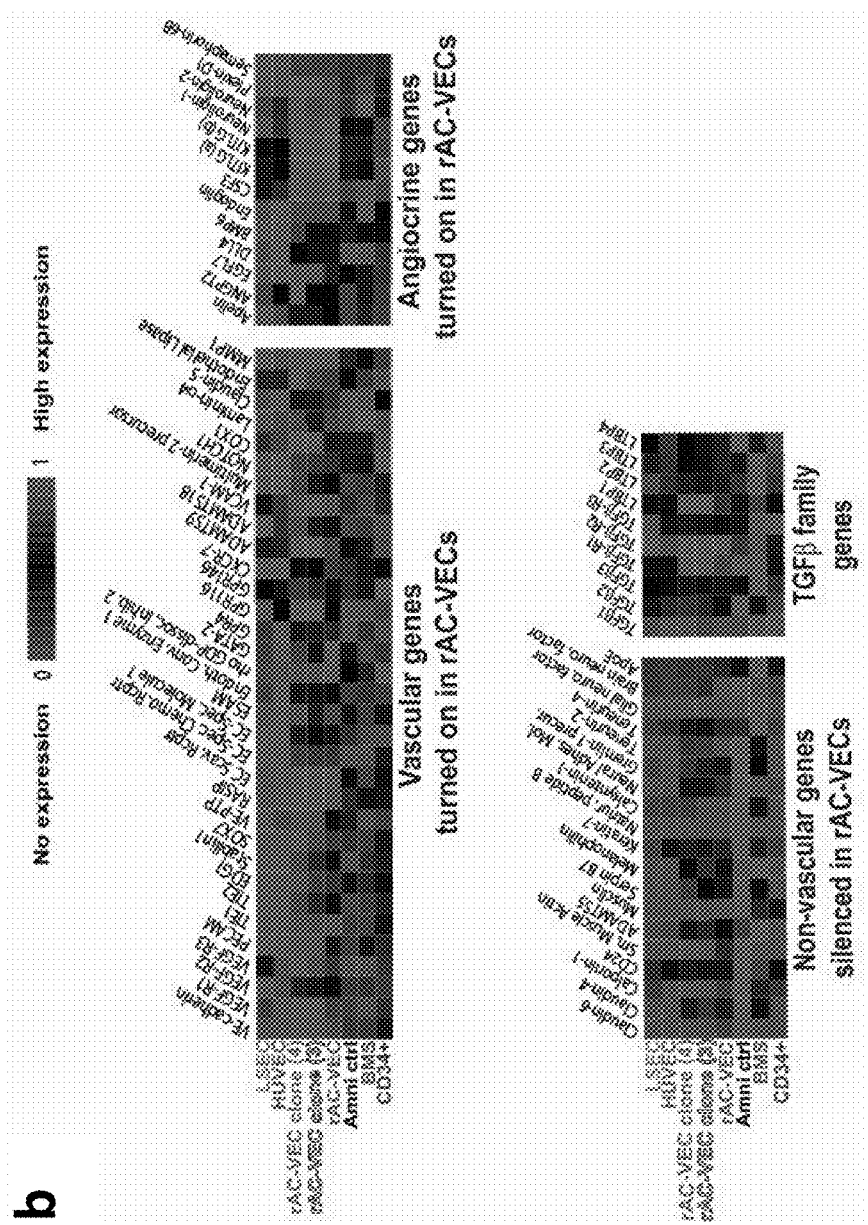

To assess whether rAC-VECs expressed the entire repertoire of EC-specific genes, while simultaneously demonstrating erasure in expression of non-vascular genes, the inventors performed transcriptome sequencing (RNA-seq) on rAC-VECs derived from ACs (both clonal and non-clonal). These genome-wide analyses of rAC-VECs were then compared to the transcriptomes of prototypical mature ECs, such as human umbilical vein ECs ('HUVEC') and adult liver sinusoidal ECs ('LSECs'), as well as non-endothelial cell-types, including CD34$^+$ hematopoietic cells ('CD34$^+$'), bone marrow stromal cells ('BMS'), lung-derived small airway epithelial cells (Hackett et al., 2012) and naïve control ACs ('Amni ctrl'). A significant number of vascular genes were upregulated in non-clonal ('rAC-VEC') and clonal ('rAC-VEC clone-3' and 'rAC-VEC clone-4') derived rAC-VECs compared to naïve ACs (FIG. 4b). Furthermore, the expression levels of these induced EC genes were comparable to those seen in in vitro cultured HUVECs and LSECs, substantiating the notion that rAC-VECs have attained a complete EC-identity. Angiocrine factors that regulate EC-driven organ regeneration (BUTLER et al., Cell Stem Cell, 6: 251-264 (2010b); DING et al., Nature, 468: 310-315 (2010); DING et al., Cell, 147: 539-553 (2011); KOBAYASHI et al., Nature cell biology, 12: 1046-1056 (2010)) and tumor growth (BUTLER et al., Nat Rev Cancer, 10: 138-146 (2010a)), including BMPs, Notch-ligands, IGFs, CSFs, Kit-ligand, and semaphorins, were all switched on in the rAC-VECs as well. Importantly, a group of non-EC genes normally expressed in ACs, such as smooth muscle actin, musclin, and calponin-1, were silenced in rAC-VECs.

Figure 4C:
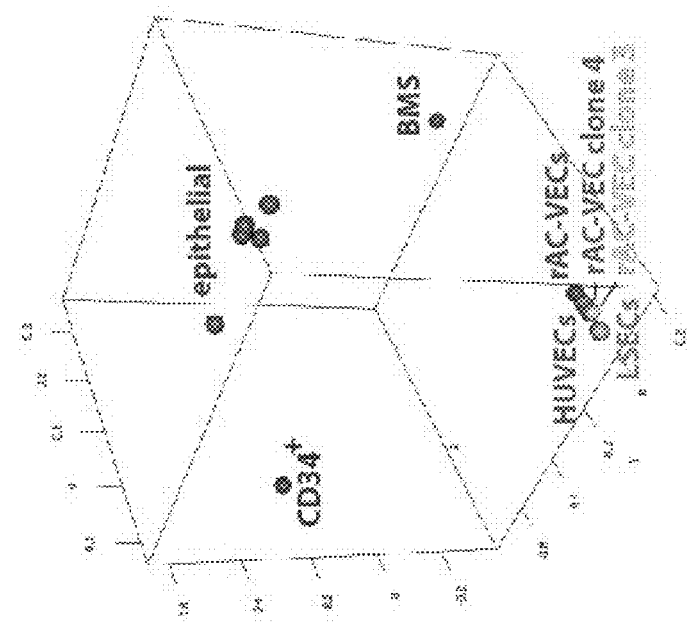
Figure 4C:
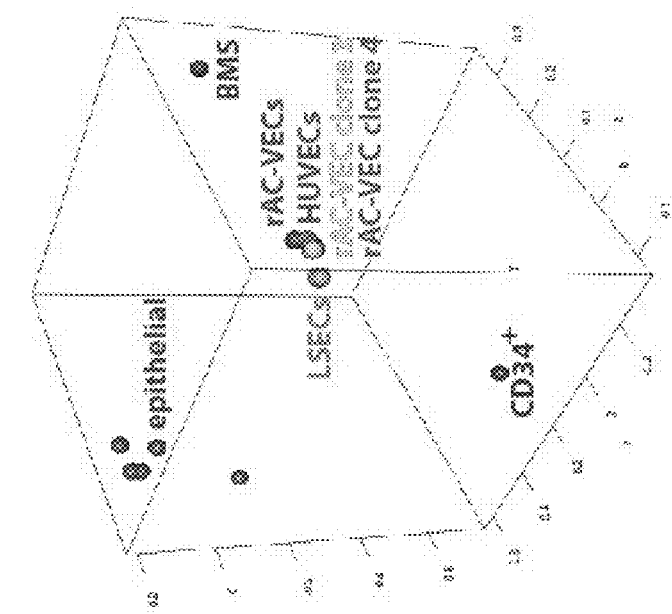

The inventors then compared rAC-VEC and adult EC transcriptomes obtained from RNA-sequencing by performing 3D multi-dimensional scaling (3D-MDS) (FIG. 4c) and hierarchical clustering analyses. These analyses show a tight association of clonal and non-clonal derived rAC-VECs with HUVECs and LSECs, while BMS, epithelial cells, and CD34$^+$ hematopoietic cells show no similarities to rAC-VECs (FIG. 4c). Notably, rAC-VECs did not express hematopoietic markers, including CD45 and CD15, ruling out the possibility that FLIT and ERG1 may have induced hematopoietic identity. Therefore, genome-wide analyses demonstrate that appropriate stoichiometric levels of ETV2, FLI1 and ERG1 expression with TGFβ inhibition reprogrammed ACs exclusively into a population of mature rAC-VECs, which resembled authentic mature ECs.

EXAMPLE 9

TGFβ Inhibition Sustains Functional VEGFR2 Signaling in rAC-VECs

Figure 5C:
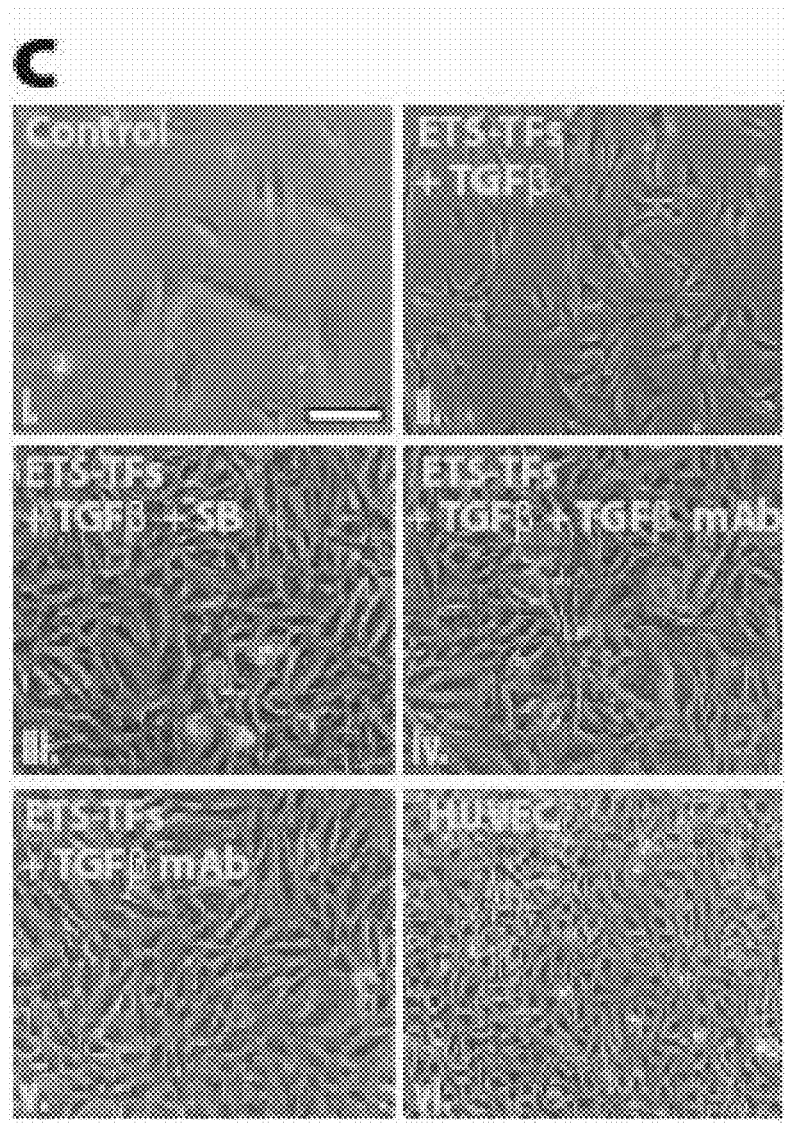
FIG. 5: TGFβ inhibition upregulates and confers functionality to VEGFR2 in ETV2/FLI1/ERG1 transduced ACs. a) Western blot analysis of ACs transduced with or without ETV2/FLI1/ERG1 for 21 days that were treated with or without TGFβ ligand neutralizing monoclonal antibody (TGFβ ligand mAb, directed against β1, β2, and β3), or TGFβ small molecule inhibition (SB431542). This experiment was performed in the presence and absence of recombinant TGFβ ligands (TGFβ1 and TGFβ3) to delineate the extent of TGFβ receptor activity. After transduction with ETV2/FLI1/ERG1, ACs were incubated with and without TGF ligands (10 ng/ml) every two days ('constant') in the presence and absence of TGFβ ligand mAb (10 µg/ml) or TGFβ small molecule inhibitor. In addition, on day 21 ETV2/FLI1/ERG1 transduced ACs were serum-starved for 4 hours, and then treated with or without one dose of TGFβ ligands (10 ng/ml) for 45 min ('pulse') in the presence and absence of TGFβ ligand mAb or TGFβ small molecule inhibitor. Following day 21 treatment, all cells were assayed for phosphorylated SMAD2 (P-SMAD2), total SMAD2, and GAPDH. b) Western blot analysis of ACs transduced with or without ETV2/FLI1/ERG1 for 21 days, in both the presence and absence of 'constant' TGFβ ligands, TGFβ ligand mAb, and/or TGFβ small molecule inhibitor, as described above. Additionally, on day 21 ETV2/FL1/ERG1 transduced ACs were serum-starved for 4 hours, and then treated with or without VEGF-A ligand (50 ng/ml) for 5 minutes. Following this day 21 treatment, cells were assayed for phosphorylated VEGFR2 (P-VEGFR2), total VEGFR2, and GAPDH. c)

ETS-TF transduced ACs produced both TGFβ and its receptors (FIG. 4b), raising the possibility that an autocrine/juxtacrine loop might regulate TGFβ dependent cell fate transitions by favoring Endo-MT and preventing rAC-VEC generation (MEDICI et al., Nat Med 16: 1400-1406 (2011); ZEISBERG et al., Nat Med, 13: 952-961 (2007)). Thus, ETV2/FLI1/ERG1 transduced ACs were cultured in the presence and absence of neutralizing mAb to TGFβ ligands, or TGFβ small molecule inhibitor (SB431542) for 21 days. It was observed that even in the absence of exogenous TGFβ ligand, basal levels of phosphorylated SMAD2 (P-SMAD2) as a readout for TGFβ signaling was still active in both control and ETV2/FLI1/ERG1 transduced ACs (FIG. 5a—lanes 1,2). This correlated with absence of total and phosphorylated VEGFR2 protein in these TGFβ activated control and ETV2/FLI1ERG1 transduced ACs (FIG. 5b—lanes 1,2,3,4). However, addition of mAb to TGFβ ligands abrogated P-SMAD2 expression in rAC-VECs (FIG. 5a—lane 7,8) upregulating VEGFR2 protein (FIG. 5b—lane 11,12) Importantly, rAC-VECs treated with mAb to TGFβ ligands were responsive to VEGF-A stimulation, as shown by the phosphorylation of VEGFR2 (FIG. 5b—lane 12). Even with supplementation of TGFβ ligand (FIG. 5a—lane 3-6) or pulsed TGFβ ligand stimulation (FIG. 5a—lane 11-16), the presence of TGFβ inhibitors prevented SMAD-2 phosphorylation allowing for upregulation of VEGFR2 protein (FIG. 5b—lane 7,8,9,10) and VEGF-A dependent phosphorylation (FIG. 5b—lane 8,10). Notably, TGFβ activated rAC-VECs failed to attain EC morphology (FIG. 5c—box ii. versus box vi.), while, inhibition of TGFβ signaling (FIG. 5c—box iii., iv., v.) endowed rAC-VECs with typical cobblestone morphology of EC monolayers (FIG. 5c—box vi.). Thus, suppression of TGFβ signaling functionalized VEGFR2 sustaining the vascular identity of rAC-VECs.

EXAMPLE 10

Transient TGFβ Inhibition for 3 Weeks Sustains Long-Term VEGFR2 Signaling and rAC-VEC Identity To generate functional VEGFR2 protein in rAC-VECs, it was essential to inhibit TGFβ signaling from the onset of ETS-TF transduction of ACs (FIG. 5d). To determine whether continuous suppression of TGFβ signaling was necessary to sustain long-term rAC-VEC stability, the inventors sequentially removed TGFβ inhibition at several time points following ETS-TF transduction (FIG. 5e—left panel). Upon removal of TGFβ inhibition at day 14 after transduction with ETV2/FLI1/ERG1, a drop in VEGFR2$^+$ cells was observed during the ensuing 7 days of cell growth (FIG. 5e—left panel, white bar). However, when TGFβ inhibition was removed at day 21 after transduction with ETV2/FLI1/ERG1, the percentage of VEGFR2$^+$ cells was sustained (FIG. 5e—left panel, gray bar). Notably, manipulation of the TGFβ pathway had no effect on VE-cadherin expression in rAC-VECs (FIG. 5e—right graph). Thus, abrogation of TGFβ signaling for 3 weeks was sufficient to functionalize VEGFR2 signaling, maintaining long-term vascular identity of stable and proliferating rAC-VECs.

EXAMPLE 11

AC-Derived rAC-VECs are Engraftable and Form Functional Perfused Vessels

Next, the inventors employed in vitro and in vivo models to assess whether rAC-VECs have acquired full angiogenic potential. A tube formation assay, using Matrigel as a substrate, was performed on day 21 rAC-VECs that were treated with TGFβ inhibitors (FIG. 6a). rAC-VECs, but not naïve ACs, were capable of forming tubes in vitro comparable to HUVEC tubulogenesis. A second in vitro assay was performed on rAC-VECs to demonstrate another EC attribute—Acetylated-LDL (Ac-LDL) uptake (FIG. 6b). Incubation of day 21 rAC-VECs with Ac-LDL showed significant accumulation of this lipoprotein similar to Ac-LDL uptake seen in HUVECs.

Figure 6C:
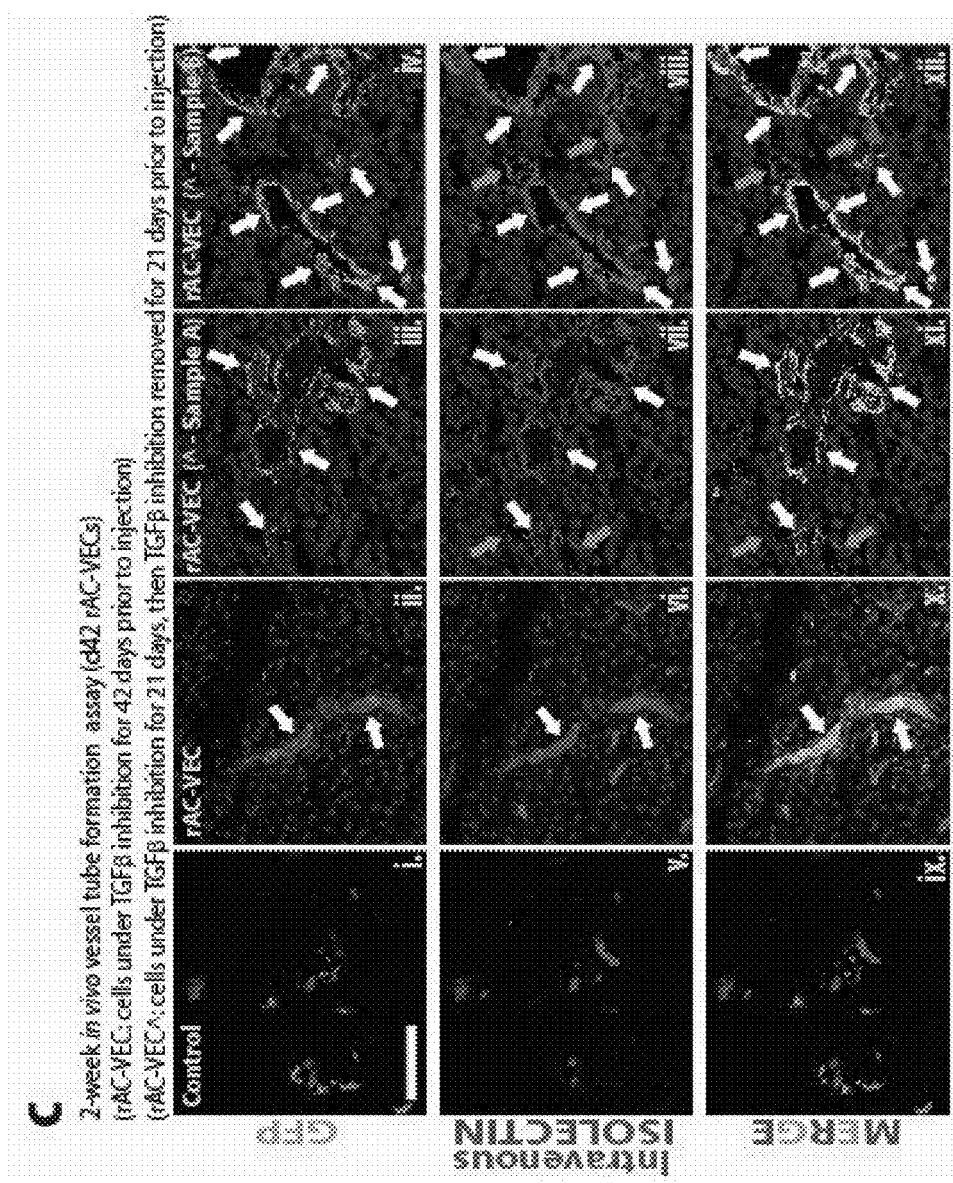

The inventors then tested for the ability of rAC-VECs to establish functional vasculature in two in vivo models. In one model, GFP-labeled day 42 rAC-VECs (and control cells) were loaded into Matrigel plugs supplemented with VEGF-A and FGF-2, and injected into immunocompromised NOD-SCIDIL2Rγ$^{-/-}$ (NSG) mice for a duration of 2 weeks (FIG. 6c). Following intravital labeling of the vasculature by intravenous (IV) injection of Alexa568-Isolectin-B4 (10 minutes prior to sacrificing the mice) to identify patent vessels, Matrigel plugs were then removed for analysis. Although naïve ACs failed to form any capillaries (FIG. 6c—box ix.), rAC-VECs formed numerous functional vessels of varying caliber that anastomosed to the host vasculature. This was verified by co-localization of GFP signal with isolectin marker, as seen in the 'merge' image (FIG. 6c—box x.).

To determine whether rAC-VECs that were treated with short-term suppression of TGFβ signaling maintained their vascular identity, rAC-VECs were generated via reprogramming for 21 days, and then subsequently cultured in EC media without TGFβ inhibition for another 21 days. These rAC-VECs were then loaded into Matrigel plugs and injected into mice (FIG. 6c—box xi., xii.). Upon retrieval 2 weeks later, analysis of these plugs shows an abundance of perfused vessels of varying caliber and size that have anastomosed to the host vessels, underscoring their functionality in vivo.

Intrasplenic transplantation of ECs results in the engraftment of these cells into the liver sinusoidal vessels of NSG mice that have undergone 70% partial hepatectomy (BENTEN et al., Hepatology, 42: 140-148 (2005); DING et al., Nature, 468: 310-315 (2010)). This in vivo model was used to interrogate the potential of rAC-VECs to incorporate long-term into the NSG mouse vasculature. 3 months following intrasplenic transplantation of $5 \times 10^5$ GFP-labeled day 21 rAC-VECs, the mice were injected IV with Alexa568-Isolectin-B4 to identify functional vessels. The number of perfused vessels engrafted with human $GFP^+$ rAC-VECs was determined by staining with mAbs specific to human CD31 (hCD31). Notably, the inventors detected the presence of $GFP^+Isolectin^+hCD31^+$ ECs within 5-10% of the regenerated vessels (FIGS. 6d and 6e). Thus, rAC-VECs included mature durable ECs that can engraft and form long-lasting patent sinusoidal vessels in regenerating liver and establish functional perfused vessels in Matrigel plugs.

EXAMPLE 12

Vascular Identity of rAC-VECs Remains Intact Following Suppression of ETV2

Figure 7A:
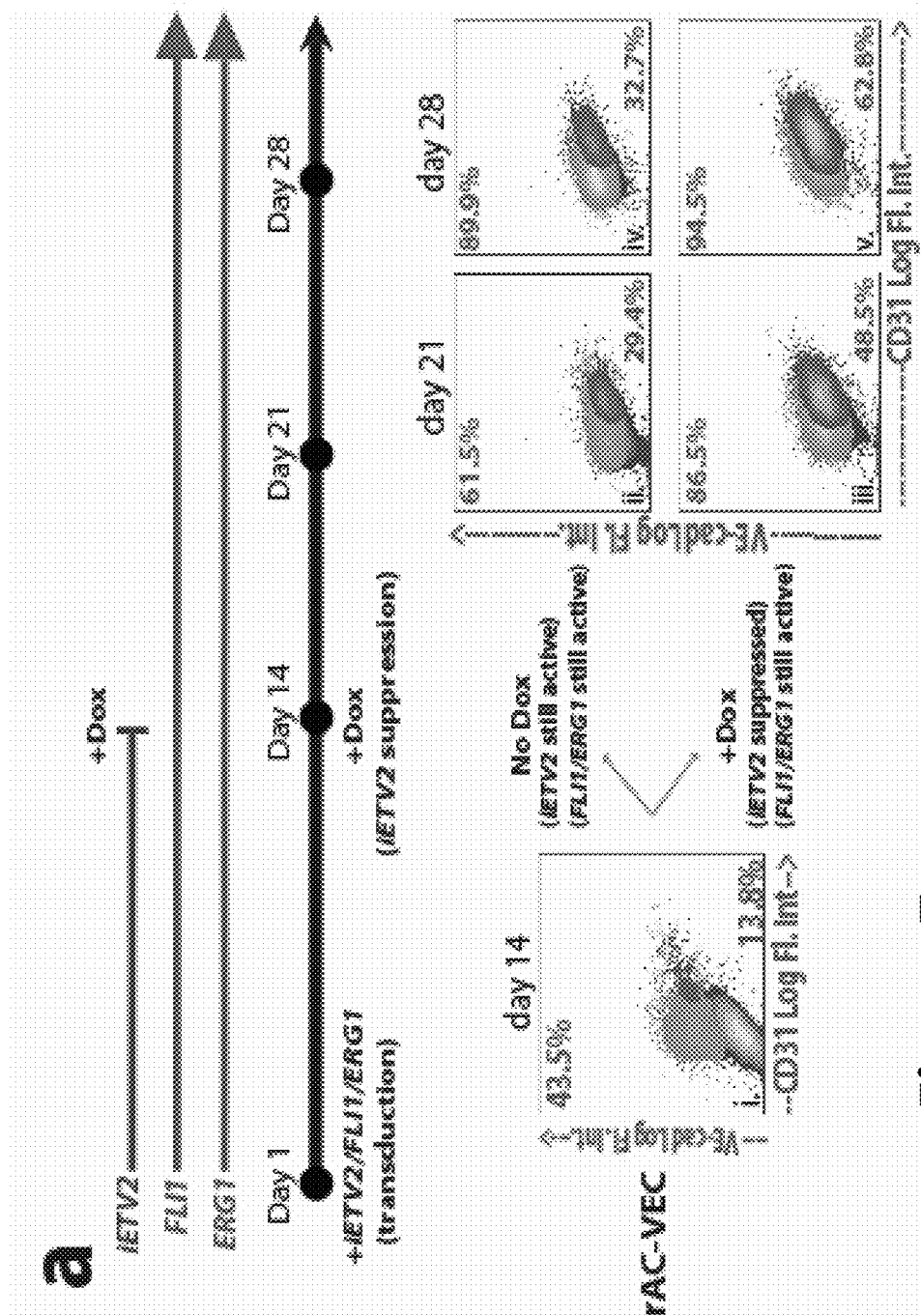

ETV2 is transiently expressed in the early phases of vascular development and its expression is presumably shut off in adult ECs (KATAOKA et al., Blood, 118: 6975-6986 (2011)). This is consistent with the observation herein that rAC-VEC clones with low ETV2 levels and appropriate ERG1 and FLI1 levels could represent populations of rAC-VECs that have achieved a mature vascular fate. Thus, transient expression of ETV2, in conjunction with sustained expression of FLI1 and ERG1, might be sufficient to initiate reprogramming of ACs and then lock in optimal rAC-VEC identity. Using a Doxycycline-dependent inducible ("Tet-off") expression system to control ETV2 production (inducible ETV2: "iETV2"), iETV2/FLI1/ERG1 were transduced in ACs and cultured with TGFβ inhibition for 14 days to allow for transition towards an EC-identity (FIG. 7a). Next, cells were treated with Doxycycline to suppress iETV2 expression, without interfering with the expression of FLI1 and ERG1. ACs transduced with iETV2/FLI1/ERG1 revealed the presence of VE-cadherin and CD31 in both Doxy-treated (iETV2 suppressed) and untreated cells beyond 4 weeks. Notably, 7 and 14 days after treatment with Doxycycline in which expression of iETV2 was silenced, there were a higher percentage of VE-cadherin$^+$CD31$^+$ rAC-VECs compared to untreated rAC-VECs (FIG. 7b). Western blot analysis verified iETV2 had indeed been silenced (FIG. 7c) in Doxy-treated cells, indicating that ETV2 was no longer required for maintaining VE-cadherin expression in rAC-VECs.

EXAMPLE 13

Figure 7D:
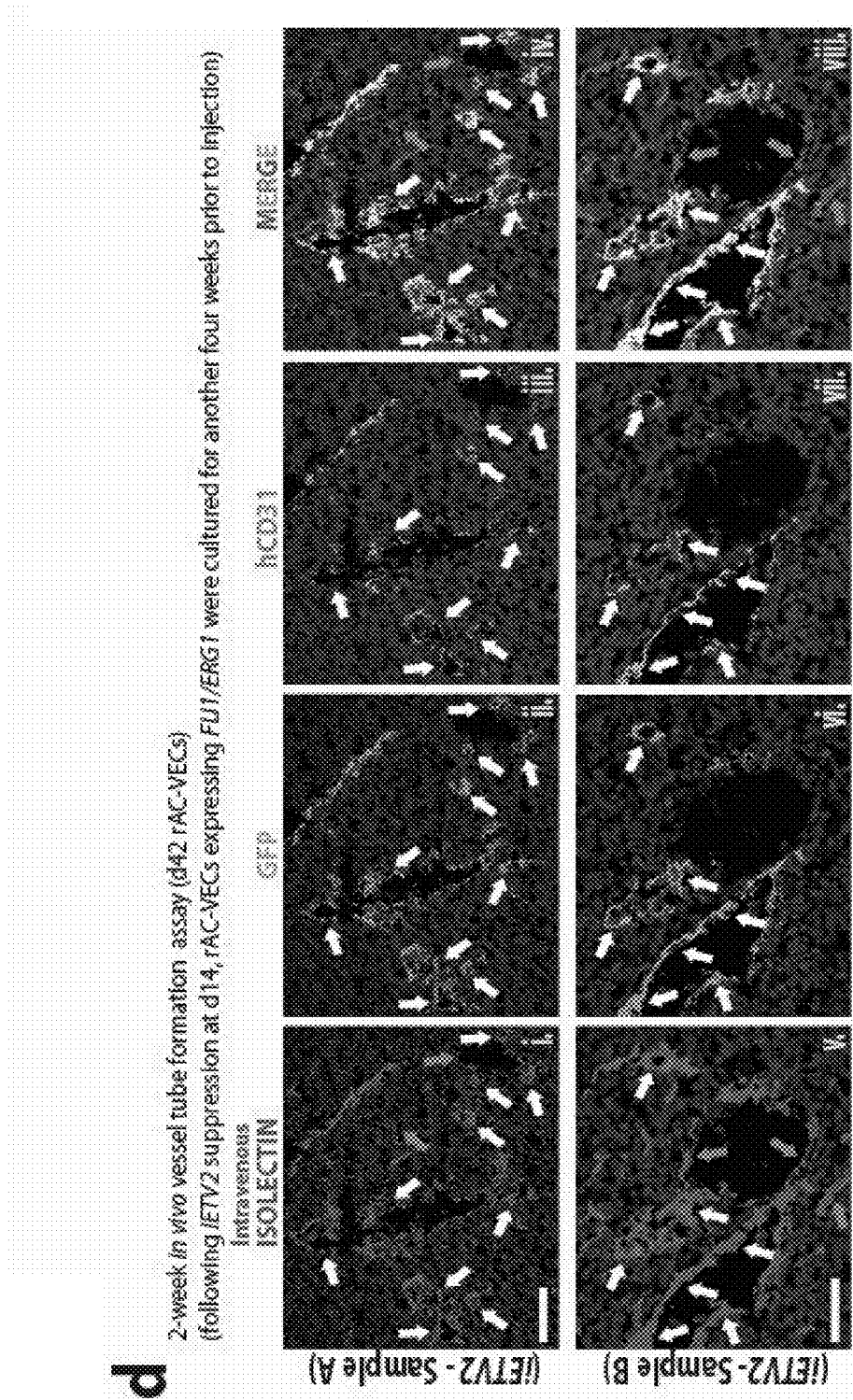

Suppression of ETV2 and constitutive FLI/ERG1 expression generate long-lasting stable mature rAC-VECs ERG1 was seen to synergize with FLI1 to enhance and sustain CD31 expression as well as other vascular-specific genes in maturing rAC-VECs (FIG. 3c and FIG. 7b). Thus, its importance in reprogramming was assayed by transducing TGFβ inhibited ACs with iETV2/FLI1 in the absence of ERG1. These cells were then split into two fractions at day 14, one of which was treated with Doxycycline to suppress iETV2 expression without perturbing FLI1 expression. A significant increase was observed in VE-cadherin$^+$CD31$^+$ rAC-VECs generated from ACs transduced with iETV2/FLI1/ERG1 compared to ACs lacking ERG1 transduction. Immunocytostaining of 28-day old iETV2/FLI1/ERG1 transduced ACs, in which iETV2 expression had been suppressed for two weeks showed co-localization of VE-cadherin and CD31 at the cell membrane, while qPCR analysis of these cells revealed expression of numerous markers indicative of a mature EC phenotype. Functionality of these cells was demonstrated via in vivo tubulogenesis assay. GFP-labeled iETV2/FLI1/ERG1 transduced ACs were cultured for 14 days, at which time iETV2 expression was suppressed. Subsequently, these cells were grown for another 28 days (d42 rAC-VECs) and then loaded into Matrigel plugs. Plugs were injected into NSG mice for 2 weeks. Following intravital labeling of the vasculature by IV injection of Alexa568-Isolectin-B4, Matrigel plugs were then removed for analysis (FIG. 7d). Immunofluorescent studies show that GFP, human CD31 (hCD31), and isolectin-marked cells were co-localized, verifying that rAC-VECs which no longer expressing iETV2 were still capable of anastomosing to the host vasculature. Therefore, upon acquiring EC identity, the vascular phenotype of rAC-VECs is permanently established through sustained expression of FLI1 and ERG1 concomitant with suppression of ETV2, a regulatory mechanism that mimics its physiological expression pattern during fetal development.

EXAMPLE 14

Discussion of the Results Described in Examples 1-13

Figure 7E:
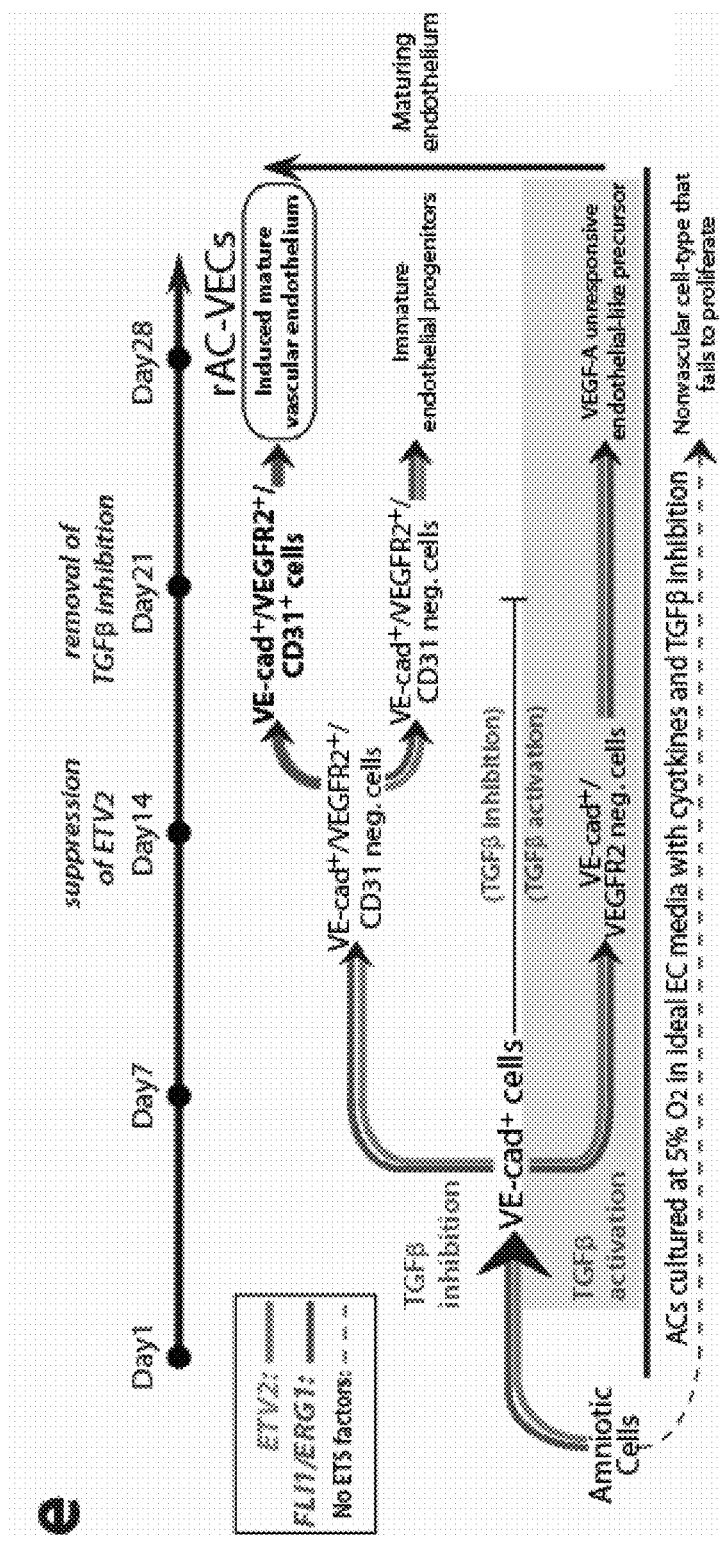

A novel ETS-TF driven platform reprograms ACs into durable and highly expandable rAC-VECs Dysfunction of the vasculature can result in a myriad of pathological abnormalities, including congestive heart failure, atherosclerosis, stroke, ischemic limbs and diabetes. Thus, the derivation and expansion of abundant engraftable human ECs could benefit patients with ischemic diseases and injured organs. However, purification and expansion of adult ECs is technically cumbersome. Moreover, current strategies to derive ECs from hESC even after transduction with ETS-TFs results in generation of ECs that are epigenetically unstable and have limited expansion potential (FIG. 1e-1g). The inventors have identified herein a versatile alternative source of human lineage-committed ACs that can be reprogrammed into highly proliferative functional ECs, referred to herein as rAC-VECs. The inventors show that enforced expression of FLI1/ERG1 concomitant with transient expression of ETV2 and TGFβ inhibition reprograms ACs into rAC-VECs, which possess the morphology and long-lasting angiogenic repertoire of mature ECs (FIG. 7e).

Transduction of ACs with ETV2/FLI1/ERG1 not only resulted in complete induction of a vascular signature, it also turned off non-vascular programs in ACs. ETS-TFs switched on the expression of key factors that establish vascular function, including adhesion molecules, ECMs (Extracellular matrices), and angiocrine factors. rAC-VECs are highly proliferative and stable, capable of undergoing $6 \times 10^4$-fold expansion in 50 days, while maintaining their full angiogenic repertoire. With an increasing number of amniocentesis being performed world-wide, genetically matched ACs will be available to generate allogeneic compatible rAC-VECs. Thus, ACs, which could be HLA-typed, cryopreserved and publically banked, are an ideal source of non-vascular cells that can be reprogrammed into durable, proliferative and engraftable ECs.

Lineage-Committed Epithelioid and Mesenchymal ACs are Amenable to Reprogramming into rAC-VECs The cellular heterogeneity of ACs has been primarily studied by staining with specific cell markers (JEZIERSKI et al., *Stem cell reviews*, 6: 199-214 (2010); ZHANG et al., *Stem cells and development*, 18: 1299-1308 (2009)). It is believed that c-Kit$^+$ cells make up a rare AC subpopulation (1% to 2%) that is multipotent (DE COPPI et al., *Nature biotechnology*, 25: 100-106 (2007)). The analyses herein of the complete AC pool support the finding of a rare c-Kit+ subpopulation (<0.5%), but the majority of ACs (i.e. c-Kit cells) express a variety of markers denoting both lineage-committed and non-committed cell types (FIG. 2c). Furthermore, the inventors did not observe any functional expression of pluripotency genes OCT4, NANOG, and SOX2.

It is unlikely that enforced ETV2/FLI1/ERG1 expression in ACs generate rAC-VECs solely from c-Kit$^+$ multipotent cells because of their scarcity in the AC population, and because the inventors' attempts to generate rAC-VECs without ETS-TF transduction were unsuccessful. Regardless, the reprogramming strategy described herein is effective in generating rAC-VECs from mature c-Kit$^-$ ACs. Within 4 days of ETS-TF transduction of c-Kit-depleted ACs, nearly 20% of the transitioning ACs expressed VE-cadherin, all of which ultimately shift into rAC-VECs. The inventors also showed that both lineage-committed EpCAM$^+$Tra1-81$^-$c-Kit$^-$ epithelioid ACs and EpCAM$^-$Tra1-81$^-$c-Kit$^-$ mesenchymal/fibroblastic ACs could be transcriptionally reprogrammed into rAC-VECs, supporting the conclusion that rAC-VECs are primarily derived from these lineage-committed mature AC populations.

Without intending to be bound by any particular theory, it is plausible that ETV2, FLI1, and ERG1 require interaction with other TFs to switch on vascular specific genes, while silencing non-vascular genes. For example, the mechanism by which ETS-TFs switch on EC-specific genes in embryonic tissues is mediated through interaction with forkhead transcription factors (DE VAL et al., *Cell*, 135: 1053-1064 (2008)). Binding of ETV2 and FoxC2 to the specific enhancer FOX:ETS regions increases the expression of EC specification genes. Notably, FoxC2 is expressed constitutively in ACs and its expression is maintained during ETV2/FLI1/ERG1 mediated reprogramming into rAC-VECs. Hence, the remarkable capacity of ETV2 to switch on numerous EC-specific genes within 4 days of AC transduction may be due to the fact that complimentary transcription factors, such as FoxC2, are expressed in ACs.

ETV2/FLI1/ERG1 TFs Switch on Vascular-Specific Genes, while Silencing the Expression of Non-Vascular Genes It has been shown herein that transduction with ETV2/FL1/ERG1 not only results in expression of a full complement of EC-specific genes, but also that reprogramming silences non-vascular AC-expressed genes. It has been shown herein by 3D-MDS and hierarchical Dendrogram clustering analyses that on a genome-wide scale the transcriptome of rAC-VECs is highly similar to prototypical fetal (HUVEC) and adult (LSEC) mature ECs, and differs drastically from non-vascular cells.

Permanent silencing of non-vascular transcription programs is clinically relevant, since persistent expression of non-vascular genes may result in malfunction of rAC-VECs. For example, sustained expression of AC-expressed genes such as Calponin-1 or Keratin-7 in rAC-VECs may predispose in vivo engrafted rAC-VECs to vascular deformity and thrombus formation. In this regard, it has been shown herein that engraftment of rAC-VECs into Matrigel plugs or regenerating mouse liver sinusoidal vessels for three months results in the generation of patent vessels without an apparent thrombosis. Thus, engraftable rAC-VECs have silenced pro-coagulation and inflammatory mediators to allow for the generation of durable vessels.

ETS-TF-Mediated Reprogramming of ACs Requires TGFβ Inhibition to Functionalize VEGFR2

Transduction of ETV2/FLI1/ERG1 into ACs without TGFβ inhibition failed to generate functional proliferative rAC-VECs. Similar to specific types of organ-specific adult ECs, such as LSECs, rAC-VECs not only express TGFβ1, β2, β3 and LTBPs, but also TGFβRII and TGFβRI resulting in constitutive SMAD2 phosphorylation. Activation of TGFβ-receptor signaling pathways could antagonize rAC-VEC generation. TGFβ-receptor signaling triggers Endo-MT (MEDICI et al., *Nat Med* 16: 1400-1406 (2011); ZEISBERG et al., *Nat Med*, 13: 952-961 (2007)), thereby hindering the formation of rAC-VECs. TGFβ also modulates acetylation of FLI1 protein, leading to a decrease in FLI1 stability and its capacity to bind DNA (ASANO et al., *Mol Cell Biol* 29: 1882-1894 (2009)). Notably, TGFβ signaling abrogates VEGFR2 expression in adult ECs (MANDRIOTA et al., *J Biol Chem*, 271: 11500-11505 (1996)), impairing proliferative and vasculogenic functions. Thus, the generation of rAC-VECs initially requires TGFβ inhibition to functionalize VEGFR2 and possibly FM as well as other unknown EC-specific targets (FIG. 5).

Transient Expression of ETV2 and Inhibition of TGFβ Pathways are Sufficient to Sustain Long-Term Vasculogenic Reprogramming of ACs into rAC-VECs Most adult ECs do not express ETV2 but constitutively express FLI1, ERG1 (DE VAL et al., *Dev Cell*, 16: 180-195 (2009)). Similarly, transient ETV2 expression in ACs for 2 weeks was sufficient to switch on all of these downstream EC-specific ETS transcription factors except FLI1 and ERG1. Therefore, ETV2 is the master regulator of EC specification resulting in full induction of vasculogenic genes. The irreversible epigenetic mechanism by which transient expression of ETV2 for 14 days results in permanent specification of EC-specific genes in ACs is intriguing and has not been reported by other reprogramming approaches of adult fibroblasts. It is plausible that upon silencing of ETV2, enforced co-expression of FLI1/ERG1, and constitutive expression of other EC-specific ETS transcription factors maintain the long-term expression of EC-specific genes.

In ACs transduced with ETV2/Fil1/ERG1, suppression of TGFβ signaling for 21 days is sufficient to sustain the expression and activation of VEGFR2 thereafter. Thus, ACs are not only amenable to reprogramming, but also adopt a stable epigenetic status after conversion into rAC-VECs.

After ETV2 Suppression, FLI1 and ERG1 Sustain Long-Term Vascular Maturity and quiescence of rAC-VECs The genes turned on by ETV2 were factors that are essential for specification of ACs into functional ECs, including VEGFR2, VE-cadherin, TIE1, TIE2, EDG-1, VEGFR1 and Notch signaling pathway genes. However, ETV2 alone was insufficient to switch on all EC genes. FLI1 and ERG1, meanwhile, turned on EC genes associated with maturity, such as CD31, ECMs, and angiocrine factors. Hence, ETV2 specifies ACs into immature endothelial progenitor cells, while FLI1 synergizes with ERG1 to induce genes that render these progenitors into mature functional ECs (FIG. 7e).

Upon silencing of ETV2 in rAC-VECs, FLI1 and ERG1 preserve EC identity. Indeed, deletion of FLI1 gene in adult ECs results in down-regulation of vascular-specific genes that modulate EC identity (Asano et al., Am J Pathol 176: 1983-1998, 2010). Thus, as demonstrated herein, constitutive expression of FLI1 plays a seminal role in stabilizing RAC-VECs. Similarly, ERG may also maintain the quiescence of ECs by repressing the activity of NF-kB (DRYDEN et al., J Biol Chem, 287: 12331-12342 (2012); YUAN et al., Circ Res, 104: 1049-1057 (2009)) and safeguarding vascular permeability by enforcing expression of Claudin5 (YUAN et al., J Biol Chem, 287: 6582-6591 (2012)) and VE-cadherin ((BIRDSEY et al., Blood, 111: 3498-3506 (2008)).

FLI1 and ERG have been implicated in the specification of hematopoietic cells (De Val and Black, Dev Cell 16: 180-195, 2009; Lee et al., Cell stem cell 2: 497-507, 2008). However, as shown herein, combinatorial transduction of ETV2concomitant with FLI1/ERG1 (along with TGFβ inhibition) did not induce hematopoietic specific genes (i.e. CD45, Thrombopoietin receptor) in rAC-VECs. Notably, SCL/TAL1, VAV3, and LMO2 genes that are co-expressed in both ECs and hematopoietic cells were induced by ETV2/FLI1/ERG1. Furthermore, derivation of true hematopoietic cells may require introduction of other TFs (i.e. RUNX1, PU.1), which are not expressed in ACs. Thus, transient expression of ETV2 may alter FM/ERG1 predilection for hematopoietic specification directing nascent rAC-VECs transition towards a vascular fate.

The inventors have found that in mature ECs, ERG is expressed in at least two isoforms (ERG1 and ERG2) with ERG1 being expressed up to 5 times more than ERG2 transcript. Moreover, as initial screening demonstrated that ERG1 accelerates the expression of CD31 compared to ERG2, the inventors focused on ERG1 to drive ACs into mature rAC-VECs. Whether coexpression of ERG2 in addition to ERG1 plays a physiological role in enhancing vascular identity to rAC-VECs is unknown.

Constitutive Expression of FLI1 and ERG1 is not Associated with Malignant Transformation Aberrant expression of FM can induce leukemia (CUI et al., Leukemia, 23: 1311-1319 (2009)) and Ewing Sarcoma (ZHANG et al., Oncogene, 8: 1621-1630 (1993)). ERG overexpression and fusion proteins have also been associated with various malignancies, including leukemias (MARTENS et al., Int J Biochem Cell Biol, 43: 1413-1416 (2012)). However, as shown herein, in vivo transplantation of rAC-VECs expressing FLI1 and ERG1 in Matrigel plugs for 14 days or in regenerating liver for 3 months have not been associated with emergence of malignancies. Employing CGH, we have also shown that expansion of rAC-VECs beyond 28 days is not associated with any chromosomal abnormalities. Long-term expansion of rAC-VECs beyond 80 days did not show any evidence of emergence of malignant transformation, hemangiomas, or hemangiosarcomas.

Therefore, rAC-VECs represent a stable and expandable cell population that provide for a safe source of vascular cells for therapeutic interventions.

Optimizing Ratios of ETS-TFs within ACs Augments the Yield of Proliferative Mature rAC-VEC Clones Singular transduction with FLI1 and/or ERG1 not only failed to confer EC-identity upon ACs, but also was ineffective in supporting proliferation of these cells. Based on the clonal analyses (FIGS. 3c-3e), it was found that proper stoichiometric ratios of ETV2 relative to FLI1 and ERG1 were key to the generation of mature and proliferative rAC-VECs, endowed with the capacity to proliferate for 80 days in culture.

By day 21, a time point in which rAC-VECs have achieved their maximal maturity, the clonal efficiency of ideal rAC-VECs, such as Clone-3 is around 20%. This efficiency could be improved as the technology used for transduction of ACs with various ETS-TFs is further optimized. Genome wide 3D-MDS analyses demonstrated that the transcriptomes of Clone-3 and other similar clones (i.e. Clone-4) match those of HUVECs and LSECs. The remarkable proliferative capacity of specific rAC-VEC clones suggest that optimal combinatorial ratios of these ETS-TF within ACs are important determinant of generating plentiful mature and stable rAC-VECs.

Potential Use of rAC-VECs for Therapeutic Vascularization

Organ-specific ECs are endowed with a unique molecular and phenotypic signature. Although microenvironmental cues may play a major role to confer organ-specificity to ECs, TFs may also play a part in this process. Reprogrammed rAC-VECs generated from ACs have the molecular profile of mature adult ECs. The genetic repertoire of reprogrammed rAC-VECs approximates that of generic in vitro cultured ECs, such as HUVECs and LSECs. Indeed, in vitro propagation of any organ-specific ECs in static culture conditions results in partial erasure of the endogenous organ-specific vascular phenotype. As such. similar to other adult ECs, the reprogrammed rAC-VECs may undergo further tissue specific specialization once reintroduced into the microenvironment of a given organ. Ultimately, identification of the specific transcription factors that endows ECs with tissue-specific signature will enable generation of rAC-VECs that will adapt to the physiological needs of that particular organ. The inventors have identified a readily available source of human lineage-committed proliferative cells with the potential for HLA-typing and allogeneic compatibility that are amenable to reprogramming into abundant functional rAC-VECs. The generation of rAC-VECs opens the door for vascularization of ischemic tissues. With thousands of amniocenteses being performed in the United States alone each year, this ensures that sufficient genetically matched ACs will be available for reprogramming into rAC-VECs that may benefit a broad cross-section of the ethnically diverse population. Given the potential of public banking of HLA-matched ACs, these cells could establish a cellular inventory for generating abundant vascular cells for treatment of genetically diverse populations of patients with vascular disorders.

TABLE 1

Primer sequences for qPCR

| | |
|---|---|
| ETV2 | f, 5'-ccgacggcgatacctactg-3' (SEQ ID NO: 1) |
| | r, 5'-gttcggagcaaacggtgag-3 (SEQ ID NO: 2) |

TABLE 1 -continued

| Primer sequences for qPCR | | |
|---|---|---|
| ERG1 | f, | 5'-tgctcaaccatctccttcca-3' (SEQ ID NO: 3) |
|  | r, | 5'-tgggtttgctcttccgctct-3' (SEQ ID NO: 4) |
| FLI1 | f, | 5'-gaggagcttggggcaataac-3' (SEQ ID NO: 5) |
|  | r, | 5'-agagcagctccaggaggaat-3' (SEQ ID NO: 6) |
| CD31 | f, | 5'-tctatgacctcgccctccacaaa-3' (SEQ ID NO: 7) |
|  | r, | 5' gaacggtgtcttcaggttggtatttca-3' (SEQ ID NO: 8) |
| VE-cadherin | f, | 5'-tggagaagtggcatcagtcaacag-3' (SEQ ID NO: 9) |
|  | r, | 5'-tctacaatcccttgcagtgtgag-3' (SEQ ID NO: 10) |
| VEGFR1 | f, | 5'-tttgcctgaaatggtgagtaagg-3' (SEQ ID NO: 11) |
|  | r, | 5'-tggtttgcttgagctgtgttc-3' (SEQ ID NO: 12) |
| VEGFR2 | f, | 5'-actttggaagacagaaccaaattatctc-3' (SEQ ID NO: 13) |
|  | r, | 5'-tgggcaccattccacca-3' (SEQ ID NO: 14) |
| VEGFR3 | f, | 5'-tgcacgaggtacatgccaac-3' (SEQ ID NO: 15) |
|  | r, | 5'-gctgctcaaagtctctcacgaa-3' (SEQ ID NO: 16) |
| RASIP (Ras Interacting protein 1) | f, | 5'-tctggtgaacggaaggagg-3' (SEQ ID NO: 17) |
|  | r, | 5'-cgaagaagacttgacagaggc-3' (SEQ ID NO: 18) |
| Tie1 | f, | 5'-ttcctgacttgcgtgtctgg-3' (SEQ ID NO: 19) |
|  | r, | 5'-cacgatacggtcgtccttct-3' (SEQ ID NO: 20) |
| EC-Scavenger Receptor | f, | 5'-cctgccagaaagacgaggtg-3' (SEQ ID NO: 21) |
|  | r, | 5'-ccaggcttgcatcgacagag-3' (SEQ ID NO: 22) |
| EC-Specific Chemotaxis Receptor | f, | 5'-cccagacctctagctctcagg-3' (SEQ ID NO: 23) |
|  | r, | 5'-ggtcagacttagaccgccaag-3' (SEQ ID NO: 24) |
| ESAM (EC-Selective Adhesion Molecule) | f, | 5'-ccctttgtgatgtggttcttca-3' (SEQ ID NO: 25) |
|  | r, | 5'-tgtaggacaacacctgatcctc-3' (SEQ ID NO: 26) |
| Endothelin | f, | 5'-agagtgtgtctacttctgcca-3' (SEQ ID NO: 27) |
|  | r, | 5'-cttccaagtccatacggaacaa-3' (SEQ ID NO: 28) |
| OCT3/4 | f, | 5'-aacctggagtttgtgccagggttt-3' (SEQ ID NO: 29) |
|  | r, | 5'-tgaacttcaccttccctccaacca-3' (SEQ ID NO: 30) |
| SOX2 | f, | 5'-cacatgaaggagcacccggattat-3' (SEQ ID NO: 31) |
|  | r, | 5'-gttcatgtgcgcgtaactgtccat-3' (SEQ ID NO: 32) |
| β-Actin | f, | 5'-cgtgcgtgacatcaaagagaa-3' (SEQ ID NO: 33) |
|  | r, | 5'-ggccatctcctgctcgaa-3' (SEQ ID NO: 34) |

What is claimed is:

1. A method of generating endothelial cells, comprising obtaining amniotic cells; and culturing the amniotic cells for at least 21 days under conditions where transcription factors ETV2, FLI1 and ERG are expressed in the amniotic cells in the presence of a TGFβ signaling inhibitor, wherein said amniotic cells express ETV2 for the first 13-15 days, said TGFβ signaling inhibitor is present for the first 20-21 days, and FLI1 and ERG are constitutively expressed, thereby obtaining endothelial cells.

2. The method of claim 1, wherein the amniotic cells are transduced with vectors comprising nucleic acids encoding transcription factors ETV2, FLI1 and ERG to achieve expression of the transcription factors.

3. The method of claim 1, wherein mRNAs encoding the transcription factors are delivered into amniotic cells to achieve expression of the transcription factors.

4. The method of claim 1, wherein the transcription factors are delivered to amniotic cells in polypeptide forms.

5. The method of claim 1, wherein the TGFβ signaling inhibitor is an inhibitor specific for the type I TGFβ receptors.

6. The method of claim 5, wherein said inhibitor is a polypeptide comprising a soluble form of a type I TGFβ receptor, an antibody directed to a type I TGFβ receptor or ligand, or a small molecule compound.

7. The method of claim 6, wherein said inhibitor is a small molecule compound selected from SB-431542, A 83-01, D 4476, LY 364947, SB 525334, SD 208, and SJN 2511.

8. The method of claim 7, wherein said inhibitor is SB-431542.

9. The method of claim 1, wherein the cells are cultured for a total duration of at least 28 days.

10. The method of claim 1, wherein the cells are cultured for a total duration of at least 42 days.

11. The method of claim 1, wherein ERG is ERG1.

12. The method of claim 1, wherein cells characterized by expression of surface markers, VE-cadherin, CD31 and VEGFR2, are isolated.

* * * * *

UNITED STATES PATENT AND TRADEMARK OFFICE
CERTIFICATE OF CORRECTION

| | | |
|---|---|---|
| PATENT NO. | : 9,637,723 B2 | Page 1 of 1 |
| APPLICATION NO. | : 14/404739 | |
| DATED | : May 2, 2017 | |
| INVENTOR(S) | : Shahin Rafii et al. | |

It is certified that error appears in the above-identified patent and that said Letters Patent is hereby corrected as shown below:

In the Specification

Column 1, Line 15 should read:

STATEMENT REGARDING FEDERALLY SPONSORED RESEARCH OR DEVELOPMENT
This invention was made with Government Support under grant number HL097797 awarded by the National Institutes of Health. The Government has certain rights in the invention.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,637,723 B2  
APPLICATION NO. : 14/404739  
DATED : May 2, 2017  
INVENTOR(S) : Shahin Rafii et al.

Page 1 of 1

It is certified that error appears in the above-identified patent and that said Letters Patent is hereby corrected as shown below:

On the Title Page

Item [73] Should Read:  
Assignee: CORNELL UNIVERSITY, Ithaca, NY (US)

Signed and Sealed this  
First Day of January, 2019

Andrei Iancu  
*Director of the United States Patent and Trademark Office*

SEQUENCE LISTING

<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 1
ccgacggcga tacctactg                                                    19

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

```
<400> SEQUENCE: 2
gttcggagca aacggtgag                                          19

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
tgctcaacca tctccttcca                                         20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
tgggtttgct cttccgctct                                         20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
gaggagcttg gggcaataac                                         20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
agagcagctc caggaggaat                                         20

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
tctatgacct cgccctccac aaa                                     23

<210> SEQ ID NO 8
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 8
gaacggtgtc ttcaggttgg tatttca                                 27

<210> SEQ ID NO 9
<211> LENGTH: 24
```

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
tggagaagtg gcatcagtca acag                                    24

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
tctacaatcc cttgcagtgt gag                                     23

<210> SEQ ID NO 11
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 11
tttgcctgaa atggtgagta agg                                     23

<210> SEQ ID NO 12
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 12
tggtttgctt gagctgtgtt c                                       21

<210> SEQ ID NO 13
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 13
actttggaag acagaaccaa attatctc                                28

<210> SEQ ID NO 14
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 14
tgggcaccat tccacca                                            17

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15

```
tgcacgaggt acatgccaac                                              20
```

<210> SEQ ID NO 16
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 16

```
gctgctcaaa gtctctcacg aa                                           22
```

<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 17

```
tctggtgaac ggaaggagg                                               19
```

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 18

```
cgaagaagac ttgacagagg c                                            21
```

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19

```
ttcctgactt gcgtgtctgg                                              20
```

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20

```
cacgatacgg tcgtccttct                                              20
```

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21

```
cctgccagaa agacgaggtg                                              20
```

<210> SEQ ID NO 22
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 22
ccaggcttgc atcgacagag                                                     20

<210> SEQ ID NO 23
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 23
cccagacctc tagctctcag g                                                   21

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
ggtcagactt agaccgccaa g                                                   21

<210> SEQ ID NO 25
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 25
ccctttgtga tgtggttctt ca                                                  22

<210> SEQ ID NO 26
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 26
tgtaggacaa cacctgatcc tc                                                  22

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
agagtgtgtc tacttctgcc a                                                   21

<210> SEQ ID NO 28
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 28
cttccaagtc catacggaac aa                                                  22
```

```
<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 29
aacctggagt ttgtgccagg gttt                                              24

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
tgaacttcac cttccctcca acca                                              24

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
cacatgaagg agcacccgga ttat                                              24

<210> SEQ ID NO 32
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 32
gttcatgtgc gcgtaactgt ccat                                              24

<210> SEQ ID NO 33
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 33
cgtgcgtgac atcaaagaga a                                                 21

<210> SEQ ID NO 34
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 34
ggccatctcc tgctcgaa                                                     18
```